US012600722B2

(12) United States Patent
Hummel et al.

(10) Patent No.: US 12,600,722 B2
(45) Date of Patent: Apr. 14, 2026

(54) TETRACYCLIC COMPOUNDS AS DGK INHIBITORS

(71) Applicant: Incyte Corporation, Wilmington, DE (US)

(72) Inventors: Joshua Hummel, Hockessin, DE (US); Shicheng Shi, Princeton, NJ (US); Xiaozhao Wang, Moorestown, NJ (US)

(73) Assignee: Incyte Corporation, Wilmington, DE (US)

( * ) Notice: Subject to any disclaimer, the term of this patent is extended or adjusted under 35 U.S.C. 154(b) by 433 days.

(21) Appl. No.: 18/222,662

(22) Filed: Jul. 17, 2023

(65) Prior Publication Data

US 2024/0025900 A1 Jan. 25, 2024

Related U.S. Application Data

(60) Provisional application No. 63/390,142, filed on Jul. 18, 2022.

(51) Int. Cl.
*C07D 471/22* (2006.01)
*A61P 35/00* (2006.01)
*C07D 498/22* (2006.01)

(52) U.S. Cl.
CPC ............ *C07D 471/22* (2013.01); *A61P 35/00* (2018.01); *C07D 498/22* (2013.01)

(58) Field of Classification Search
CPC ...... C07D 471/22; C07D 498/22; A61P 35/00
See application file for complete search history.

(56) References Cited

U.S. PATENT DOCUMENTS

| | | | |
|---|---|---|---|
| 6,833,454 | B1 | 12/2004 | Koppes et al. |
| 7,381,401 | B2 | 6/2008 | Gajewski et al. |
| 7,488,802 | B2 | 2/2009 | Collins et al. |
| 7,943,743 | B2 | 5/2011 | Korman et al. |
| 8,008,449 | B2 | 8/2011 | Korman et al. |
| 8,168,757 | B2 | 5/2012 | Finnefrock et al. |
| 8,217,149 | B2 | 7/2012 | Irving et al. |
| 8,618,288 | B2 | 12/2013 | Dvorak et al. |
| 10,087,180 | B2 | 10/2018 | Ford et al. |
| 10,308,644 | B2 | 6/2019 | Wu et al. |
| 2007/0161072 | A1 | 7/2007 | Prescott et al. |
| 2017/0145025 | A1 | 5/2017 | Li et al. |
| 2017/0174671 | A1 | 6/2017 | Wu et al. |
| 2017/0174679 | A1 | 6/2017 | Lajkiewicz et al. |
| 2017/0320875 | A1 | 11/2017 | Li et al. |
| 2017/0342060 | A1 | 11/2017 | Lu et al. |
| 2017/0362253 | A1 | 12/2017 | Xiao et al. |
| 2018/0016260 | A1 | 1/2018 | Yu et al. |
| 2018/0028501 | A1 | 2/2018 | Lindsley et al. |
| 2018/0057486 | A1 | 3/2018 | Wu et al. |
| 2018/0177784 | A1 | 6/2018 | Wu et al. |
| 2018/0177870 | A1 | 6/2018 | Liu et al. |
| 2018/0179179 | A1 | 6/2018 | Wu et al. |
| 2018/0179197 | A1 | 6/2018 | Wu et al. |
| 2018/0179201 | A1 | 6/2018 | Wu et al. |
| 2018/0179202 | A1 | 6/2018 | Wu et al. |
| 2018/0273519 | A1 | 9/2018 | Wu et al. |
| 2019/0040082 | A1 | 2/2019 | Xiao et al. |
| 2019/0062345 | A1 | 2/2019 | Xiao et al. |
| 2019/0071439 | A1 | 3/2019 | Li et al. |
| 2019/0127467 | A1 | 5/2019 | Shah et al. |
| 2019/0144439 | A1 | 5/2019 | Wu et al. |
| 2019/0202824 | A1 | 7/2019 | Wu et al. |
| 2019/0225601 | A1 | 7/2019 | Wu et al. |
| 2019/0300524 | A1 | 10/2019 | Wu et al. |
| 2019/0345170 | A1 | 11/2019 | Wu et al. |
| 2023/0399342 | A1 | 12/2023 | Hummel et al. |
| 2024/0034734 | A1 | 2/2024 | Hummel et al. |
| 2024/0083898 | A1 | 3/2024 | Hummel et al. |
| 2024/0217989 | A1 | 7/2024 | Xiang et al. |
| 2024/0270739 | A1 | 8/2024 | Xiang et al. |
| 2025/0066363 | A1 | 2/2025 | Hummel et al. |
| 2025/0179083 | A1 | 6/2025 | Hummel et al. |
| 2025/0186450 | A1 | 6/2025 | Ren et al. |

FOREIGN PATENT DOCUMENTS

| | | | |
|---|---|---|---|
| CN | 105315293 A | 2/2016 |
| CN | 109180686 A | 1/2019 |
| CN | 110643705 | 1/2020 |
| CN | 111097048 | 5/2020 |
| CN | 112300194 A | 2/2021 |
| CN | 113061132 A | 7/2021 |
| CN | 115463214 | 12/2022 |
| CN | 116969943 A | 10/2023 |
| EP | 4083038 A1 | 11/2022 |
| WO | WO 2001/002398 A1 | 1/2001 |
| WO | WO 2002/000196 A2 | 1/2002 |
| WO | WO 2002/077177 A2 | 10/2002 |
| WO | WO 2003/042402 A2 | 5/2003 |
| WO | WO 2004/021984 A2 | 3/2004 |
| WO | WO 2005/121138 A2 | 12/2005 |
| WO | WO 2007/019083 A1 | 2/2007 |
| WO | WO 2007/109251 A2 | 9/2007 |
| WO | WO 2008/017161 A1 | 2/2008 |
| WO | WO 2008/148926 A2 | 12/2008 |
| WO | WO 2008/156712 A1 | 12/2008 |
| WO | WO 2009/017863 A2 | 2/2009 |
| WO | WO 2007/114239 A1 | 8/2009 |
| WO | WO 2010/036959 A2 | 4/2010 |

(Continued)

OTHER PUBLICATIONS

Arranz-Nicolás et al., "Diacylglycerol kinase a inactivation is an integral component of the costimulatory pathway that amplifies TCR signals," Cancer Immunology Immunotherapy, Jun. 2018, 67(6):965-980.

(Continued)

*Primary Examiner* — Kamal A Saeed
*Assistant Examiner* — Quincy Mckoy
(74) *Attorney, Agent, or Firm* — Fish & Richardson P.C.

(57) ABSTRACT

The present application provides tetracyclic compounds that modulate the activity of diacylglycerol kinase (DGK), which are useful in the treatment of various diseases, including cancer.

63 Claims, No Drawings

(56) References Cited

FOREIGN PATENT DOCUMENTS

| | | | | |
|---|---|---|---|---|
| WO | WO 2010/089411 A2 | | 8/2010 | |
| WO | WO 2011/066342 A2 | | 6/2011 | |
| WO | WO 2011/082400 A2 | | 7/2011 | |
| WO | WO 2011/143423 A2 | | 11/2011 | |
| WO | WO 2011/159877 A2 | | 12/2011 | |
| WO | WO 2011/161699 A2 | | 12/2011 | |
| WO | WO 2012/080727 A2 | | 6/2012 | |
| WO | WO 2012/080729 A2 | | 6/2012 | |
| WO | WO 2012/130780 A1 | | 10/2012 | |
| WO | WO 2014/096423 A1 | | 6/2014 | |
| WO | WO 2015/054572 A1 | | 4/2015 | |
| WO | WO 2015/095492 A1 | | 6/2015 | |
| WO | WO 2015/193167 A1 | | 12/2015 | |
| WO | WO 2016/044772 A1 | | 3/2016 | |
| WO | WO 2018/062954 A1 | | 4/2018 | |
| WO | WO 2019/005883 A1 | | 1/2019 | |
| WO | WO 2019/046795 A1 | | 3/2019 | |
| WO | WO 2020/006016 A1 | | 1/2020 | |
| WO | WO 2020/006018 A1 | | 1/2020 | |
| WO | WO 2020/110127 A1 | | 6/2020 | |
| WO | WO 2020/239123 A1 | | 12/2020 | |
| WO | WO 2021/013561 A1 | | 1/2021 | |
| WO | WO 2021/041588 A1 | | 3/2021 | |
| WO | WO 2021/052499 A1 | | 3/2021 | |
| WO | WO-2021083167 A1 | * | 5/2021 | ........... C07D 498/22 |
| WO | WO 2021/105115 A1 | | 6/2021 | |
| WO | WO 2021/105116 A1 | | 6/2021 | |
| WO | WO 2021/105117 A1 | | 6/2021 | |
| WO | WO 2021/127554 A1 | | 6/2021 | |
| WO | WO 2021/130638 A1 | | 7/2021 | |
| WO | WO 2021/132422 A1 | | 7/2021 | |
| WO | WO 2021/133748 A1 | | 7/2021 | |
| WO | WO 2021/133749 A1 | | 7/2021 | |
| WO | WO 2021/133750 A1 | | 7/2021 | |
| WO | WO 2021/133751 A1 | | 7/2021 | |
| WO | WO 2021/133752 A1 | | 7/2021 | |
| WO | WO 2021/219513 A1 | | 11/2021 | |
| WO | WO 2021/234607 A1 | | 11/2021 | |
| WO | WO 2021/243421 A1 | | 12/2021 | |
| WO | WO 2021/258010 A1 | | 12/2021 | |
| WO | WO 2022/037630 A1 | | 2/2022 | |
| WO | WO 2022/076446 A1 | | 4/2022 | |
| WO | WO 2022/108980 A1 | | 5/2022 | |
| WO | WO 2022/114164 A1 | | 6/2022 | |
| WO | WO 2022/114812 A1 | | 6/2022 | |
| WO | WO 2022/133083 A1 | | 6/2022 | |
| WO | WO 2022/171745 A1 | | 8/2022 | |
| WO | WO 2022/187406 A1 | | 9/2022 | |
| WO | WO 2022/271650 A1 | | 12/2022 | |
| WO | WO 2022/271659 A1 | | 12/2022 | |
| WO | WO 2022/271677 A1 | | 12/2022 | |
| WO | WO 2022/271684 A1 | | 12/2022 | |
| WO | WO 2023/011456 A1 | | 2/2023 | |
| WO | WO 2023/125681 A1 | | 7/2023 | |
| WO | WO 2023/150186 A1 | | 8/2023 | |
| WO | WO 2023/165525 A1 | | 9/2023 | |
| WO | WO 2023/184327 A1 | | 10/2023 | |
| WO | WO 2024/160277 A1 | | 8/2024 | |

OTHER PUBLICATIONS

Atzrodt et al., "The renaissance of H/D exchange," Angewandte Chemie International Edition English, Oct. 2007, 46(41):7744-7765.

Bennett et al., "Proposals for the classification of the myelodysplastic syndromes," British Journal of Haematology, Jun. 1982, 51(2):189-199.

Blom et al., "Optimizing preparative LC/MS configurations and methods for parallel synthesis purification," Journal of Combinatorial Chemistry, Sep. 2003, 5(5):670-683.

Blom et al., "Preparative LC-MS Purification: Improved Compound-Specific Method Optimization," Journal of Combinatorial Chemistry, Nov. 2004, 6(6):874-883.

Blom, "Two-Pump at-col. Dilution Configuration for Preparative Liquid Chromatography—Mass Spectrometry," Journal of Combinatorial Chemistry, Jul. 2002, 4(4):295-301.

Cai et al., "Increased diacylglycerol kinase ξ expression in human metastatic colon cancer cells augments Rho GTPase activity and contributes to enhanced invasion," BMC cancer, Mar. 19, 2014, 14:208.

Chen et al., "Diacylglycerol Kinases in T Cell Tolerance and Effector Function," Frontiers in Cell and Development Biology, Nov. 10, 2016, 4:130.

Chen et al., "The diacylglycerol kinase α (DGKα)/Akt/NF-κB feedforward loop promotes esophageal squamous cell carcinoma (ESCC) progression via FAK-dependent and FAK-independent manner," Oncogene, Apr. 2019, 38(14):2533-2550.

Chinchilla et al., "Recent advances in Sonogashira reactions," Chemical Society Reviews, Oct. 2011, 40(10):5084-5121.

Cooke et al., "Overarching roles of diacylglycerol signaling in cancer development and antitumor immunity," Science Signaling, Apr. 2022, 15(729):eabo0264, pp. 1-26.

Cordovilla et al., "The Stille reaction, 38 years later," ACS Catalysis, May 2015, 5(5):3040-3053.

Fu et al., "DGKA interacts with SRC/FAK to promote the metastasis of non-small cell lung cancer," Cancer Letters, Apr. 2022, 532:215585.

Gonzalez et al., "Roles of the immune system in cancer: from tumor initiation to metastatic progression," Genes & Development, Oct. 2018, 32(19-20):1267-1284.

Gu et al., "DGKξ exerts greater control than DGKα over CD8+ T cell activity and tumor inhibition," Oncoimmunology, Jan. 2021, 10(1):1941566.

Haas et al., "Recent developments in Negishi cross-coupling reactions," ACS Catalysis, Mar. 2016, 6(3):1540-1552.

Harabuchi et al. "Manipulation of diacylglycerol and ERK-mediated signaling differentially controls CD8+ T cell responses during chronic viral infection," Frontiers in Immunology, Nov. 2022, 13:1032113.

Harris et al., "World Health Organization classification of neoplastic diseases of the hematopoietic and lymphoid tissues: report of the Clinical Advisory Committee meeting—Airlie House, Virginia, Nov. 1997," Journal of Clinical Oncology, Dec. 1999, 17(12):3835-3849.

Joshi et al.,"Diacylglycerol kinases: regulated controllers of T cell activation, function, and development," International Journal of Molecular Sciences, Mar. 2013, 14(4):6649-6673.

Jung et al., "CRISPR/Cas9-mediated knockout of DGK improves antitumor activities of human T cells," Cancer Research, Aug. 2018, 78(16):4692-4703.

Kerekes et al., "Aurora kinase inhibitors based on the imidazo [1, 2-a] pyrazine core: fluorine and deuterium incorporation improve oral absorption and exposure," Journal of Medicinal Chemistry, Jan. 2011, 54(1):201-210.

Kotha et al., "Recent applications of the Suzuki-Miyaura cross-coupling reaction in organic synthesis," Tetrahedron, Nov. 2002, 58(48):9633-9695.

Krishna et al., "Regulation of lipid signaling by diacylglycerol kinases during T cell development and function," Frontiers in Immunology, Jul. 2013, 4:178.

Mérida et al., "Diacylglycerol kinases in cancer," Advances in Biological Regulation, Jan. 2017, 63:22-31.

Prinz et al., "High DGK-α and disabled MAPK pathways cause dysfunction of human tumor-infiltrating CD8+ T cells that is reversible by pharmacologic intervention," The Journal of Immunology, Jun. 15, 2012, 188(12):5990-6000.

Rainero et al., "The diacylglycerol kinase α/atypical PKC/β1 integrin pathway in SDF-1α mammary carcinoma invasiveness," PloS One, Jun. 2014, 9(6):e97144.

Remington's Pharmaceutical Sciences, 17th ed., 1985, p. 1418.

Riese et al, "Diacylglycerol kinases (DGKs): novel targets for improving T cell activity in cancer," Frontiers in Cell and Developmental Biology, Oct. 2016, 4:108.

Riese et al., "Enhanced effector responses in activated CD8+ T cells deficient in diacylglycerol kinases," Cancer Research, Jun. 2013, 73(12):3566-3577.

(56) References Cited

OTHER PUBLICATIONS

Ruffo et al., "Inhibition of diacylglycerol kinase α restores restimulation-induced cell death and reduces immunopathology in XLP-1," Science Translational Medicine, Jan. 2016, 8(321):321ra7.
Sakane et al., "New era of diacylglycerol kinase, phosphatidic acid and phosphatidic acid-binding protein," International Journal of Molecular Sciences, Sep. 2020, 21(18):6794-6829.
Sharma et al., "Primary, adaptive, and acquired resistance to cancer immunotherapy," Cell, Feb. 2017, 168(4):707-723.
Sharma et al., "The next decade of immune checkpoint therapy," Cancer Discovery, Apr. 2021, 11(4):838-857.
Sitaram et al., "Beyond the cell surface: targeting intracellular negative regulators to enhance T cell anti-tumor activity," International Journal of Molecular Sciences, Nov. 2019, 20(23):5821-5848.
Speiser et al., "Regulatory circuits of T cell function in cancer," Nature Reviews Immunology, Oct. 2016, 16(10):599-611.
Surry et al., "Dialkylbiaryl Phosphines in Pd-Catalyzed Amination: A User's Guide," Royal Society of Chemistry, 2011, 2(1):27-50.
Swerdlow et al., WHO Classification of Tumours of Haematopoietic and Lymphoid Tissues, $4^{th}$ ed., 2008, pp. 88-103.
Takeishi et al., "Diacylglycerol kinase alpha enhances hepatocellular carcinoma progression by activation of Ras-Raf-MEK-ERK pathway," Journal of Hepatology, Jul. 2012, 57(1):77-83.
Torres-Ayuso et al., "Diacylglycerol kinase α promotes 3D cancer cell growth and limits drug sensitivity through functional interaction with Src," Oncotarget, Oct. 2014, 5(20):9710-9726.
Vardiman et al., "The 2008 revision of the World Health Organization (WHO) classification of myeloid neoplasms and acute leukemia: rationale and important changes," Blood, Jul. 2009, 114(5):937-951.
Vardiman et al., "The World Health Organization (WHO) classification of the myeloid neoplasms," Blood, Oct. 2002, 100(7):2292-2302.
Velnati et al., "Identification of a novel DGKα inhibitor for XLP-1 therapy by virtual screening," European Journal of Medicinal Chemistry, Feb. 2019, 164:378-390.
Wesley et al., "Diacylglycerol Kinase ξ (DGKξ) and Casitas b-Lineage Proto-Oncogene b-deficient mice have similar functional outcomes in T Cells but DGKξ-deficient mice have increased T cell activation and tumor clearance," Immunohorizons, Apr. 2018, 2(4):107-118.
Xu et al., "Design, synthesis and biological evaluation of deuterated nintedanib for improving pharmacokinetic properties," Journal of Labelled Compounds and Radiopharmaceuticals, Jun. 2015, 58(7):308-312.
Yu et al., "DGKZ acts as a potential oncogene in osteosarcoma proliferation through its possible interaction with ERK1/2 and MYC pathway," Frontiers in Oncology, Jan. 4, 2019, 8:655.
Noessner, "DGK-α: A Checkpoint in Cancer-Mediated Immuno-Inhibition and Target for Immunotherapy," Frontiers in Cell and Developmental Biology, Mar. 3, 2017, 5(Article 16):7 pages.
Sadreddini et al., "Immune checkpoint blockade opens a new way to cancer immunotherapy," Cellular Physiology, Jun. 2019, 234:8541-8549.

* cited by examiner

TETRACYCLIC COMPOUNDS AS DGK INHIBITORS

TECHNICAL FIELD

The present invention provides tetracyclic compounds that modulate the activity of diacylglycerol kinase (DGK) and are useful in the treatment of diseases related to diacylglycerol kinase, including cancer.

BACKGROUND

Diacylglycerol kinases (DGKs) are a family of enzymes that regulate many biological processes, including cellular proliferation, migration, immunity and pathogenesis of diseases such as cancer. In mammalian systems, there are ten DGK family members classified into five subtypes based on shared common domains (Sakane F. et al., *Int. J. Mol. Sci.,* 2020. 21: p 6794-6829). The diverse and specific cellular function of individual DGK isoforms is regulated through their tissue restricted expression, localization within cells and interactions with regulatory proteins (Joshi, R. P. and Koretzky, G. A., *Int. J. Mol. Sci.,* 2013. 14: p 6649-6673).

In T lymphocytes, DGKα and ζ are the dominant DGK isoforms expressed (Krishna, S. and Zhong, X.-P., *Front Immunol.,* 2013. 4:178). Specifically, in response to T cell receptor (TCR) activation, phospholipase Cγ1 (PLCγ1) hydrolyzes membrane phospholipid PIP2 to produce diacylglycerol (DAG) (Krishna, S. and Zhong, X.-P., *Front Immunol.,* 2013. 4:178; Riese, M. J. et al., *Front Cell Dev Biol.,* 2016. 4:108). In turn, DAG functions as a second messenger to recruit RasGRP1 and PKCθ to the cell membrane and thereby initiates multiple downstream signaling events resulting in T cell activation. To prevent hyperactivation of T cells, DGKα and ζ tightly regulate the levels of intracellular DAG by phosphorylating DAG to produce phosphatidic acid (PA). Both mouse and human cell line genetic studies support the important regulatory role of DGKα and ζ in T cell activation. Knockout or depletion of DGKα and ζ has been reported to enhance T cell activation, cytokine production and proliferation. Furthermore, knockout of both DGKα and ζ show even greater T-cell activation over individual knockouts, indicating a non-redundant role of these two isoforms (Riese, M. J. et al., *Cancer Res.,* 2013. 73:p 3566-3577; Jung, I.-Y. et al., *Cancer Res.,* 2018. 78: p 4692-4703). Thus, DGKα and ζ by regulating cellular DAG levels link lipid metabolism and intracellular signaling cascades and function as key regulators of T cell activation.

Cytotoxic T lymphocytes (CTLs) are a major component of the adaptive immune system that recognize and kill cells with bacterial or viral infections, or cells displaying abnormal proteins, such as tumor antigens. However, cancer cells can evolve to utilize multiple mechanisms that mimic peripheral immune tolerance to avoid immune surveillance and killing by CTLs. Such mechanisms include downregulation of antigen presentation, suppression of T cell function through increased expression of inhibitory molecules, as well as increased production of immunosuppressive proteins in the tumor microenvironment (Speiser, D. E. et al., *Nat. Rev. Immunol.,* 2016. 16: p. 599-611, Gonzalez H. et al., *Genes & Dev.,* 2018. 32:p 1267-1284). Immune checkpoint therapy (ICT) by blocking inhibitory molecules such as PD(L)-1 and CTLA4, can restore T cell activity and have been clinically useful in treating many different types of cancers. However, only subsets of patients respond to ICT due to primary or acquired resistance (Sharma, P. et al., *Cell.* 2017. 168: p 707-723). Thus, despite the significant recent clinical successes of immunotherapies to treat cancer, resistance remains a challenge (Sharma, P., et al., *Cancer Discov.,* 2021. 11: p 838-857).

Overexpression of DGKα and ζ has been observed in tumor infiltrating lymphocytes (TILs) from human tumors and proposed to suppress T cell function. Importantly, significant immune-mediated antitumor activity has been shown in DGKα and DGKζ deficient mouse models (Merida, I. et al., *Adv. Biol. Regul.,* 2017. 63:p 22-31, Prinz, P. U. et al., *J. Immunol.,* 2012. 188:p 5990-6000). Furthermore, DGKα and DGKζ deficient T cells are resistant to several immunosuppressive factors within the tumor microenvironment such as TGFβ, PGE2 and adenosine, and to other T cell inhibitory pathways such as PD(L)-1 mediated immune suppression (Riese, M. J. et al., *Cancer Res.,* 2013. 73:p 3566-77; Jung, I.-Y. et al. (2018) *Cancer Res.,* 2018. 78:p 4692-4703; Arranz-Nicolas, J. et al., *Cancer Immunol. Immunother.,* 2018. 67:p 965-980; Riese, M. J. et al., *Front. Cell Dev. Biol.,* 2016. 4:108). Thus DGKα and DGKζ are attractive targets as immunotherapies alone or in combination with current ICT therapies such as PD(L)-1 and CTLA4. By targeting T cell lipid metabolism, DGKα and DGKζ inhibition can potentially restore antitumor immunity in subsets of patient who have primary or acquired immune resistance and are consequently refractory to current ICTs. In addition to its function in T lymphocytes, DGKα and DGKζ, by regulating DAG level in cancer cells, have also been reported to directly contribute to cancer proliferation, migration, invasion and survival. Thus, DGK inhibition may have direct antitumor effect by interfering with tumor intrinsic oncogenic survival pathways (Cooke, M. and Kaznietz, M. G., *Sci. Signal.,* 2022. 15:eabo0264).

Compounds in this application may have selective activities towards one or both DGKα and DGKζ. These DGK inhibitors alone or in combination with other therapeutic agent(s) can be used in treatment of cancer.

SUMMARY

The present invention relates to, inter alia, compounds of Formula I:

I

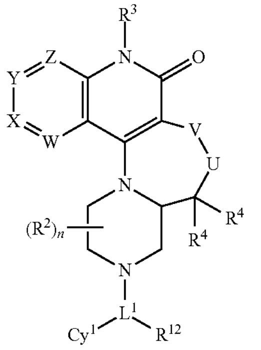

or pharmaceutically acceptable salts thereof, wherein constituent members are defined herein.

The present invention further provides pharmaceutical compositions comprising a compound of Formula I, or a pharmaceutically acceptable salt thereof, and a pharmaceutically acceptable carrier.

The present invention further provides methods of inhibiting an activity of diacylglycerol kinase (DGK), comprising contacting the kinase with a compound of Formula I, or a pharmaceutically acceptable salt thereof.

The present invention further provides methods of treating a disease or a disorder associated with expression or activity of a diacylglycerol kinase (DGK) in a patient by administering to a patient a therapeutically effective amount of a compound of Formula I, or a pharmaceutically acceptable salt thereof.

The present invention further provides a compound of Formula I, or a pharmaceutically acceptable salt thereof, for use in any of the methods described herein.

The present invention further provides use of a compound of Formula I, or a pharmaceutically acceptable salt thereof, for the preparation of a medicament for use in any of the methods described herein.

DETAILED DESCRIPTION

The present application provides a compound of Formula I:

I

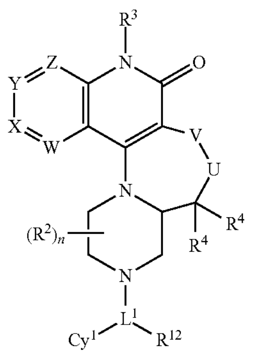

or a pharmaceutically acceptable salt thereof, wherein:

- ═══ is a single or double bond;
- U is C(O) and V is $NR^6$; or
- U is $NR^5$ or O and V is C(O);
- W is $CR^7$, C(O), N, or $NR^7$;
- X is $CR^8$, C(O), N, or $NR^8$;
- Y is $CR^9$ or N;
- Z is $CR^{10}$ or N;
- wherein:
  - (i) when W is C(O) then X is $NR^8$;
  - (ii) when X is C(O) then W is $NR^7$; and
  - (iii) no more than 2 of W, X, Y, and Z can be N or a substituted N;
- n is 0, 1, or 2;
- each $R^2$ is independently selected from halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, CN, $NO_2$, $OR^{a2}$, $NHOR^{a2}$, $C(O)R^{b2}$, $C(O)NR^{c2}R^{d2}$, $C(O)NR^{c2}(OR^{a2})$, $C(O)OR^{a2}$, $OC(O)R^{b2}$, $OC(O)NR^{c2}R^{d2}$, $NR^{c2}R^{d2}$, $NR^{c2}NR^{c2}R^{d2}$, $NR^{c2}C(O)R^{b2}$, $NR^{c2}C(O)OR^{a2}$, $NR^{c2}C(O)NR^{c2}R^{d2}$, $C({=}NR^{e2})R^{b2}$, $C({=}NR^{e2})NR^{c2}R^{d2}$, $NR^{c2}C({=}NR^{e2})NR^{c2}R^{d2}$, $NR^{c2}C({=}NR^{e2})R^{b2}$, $NR^{c2}S(O)R^{b2}$, $NR^{c2}S(O)N^{c2}R^{d2}$, $NR^{c2}S(O)_2R^{b2}$, $NR^{c2}S(O)({=}NR^{e2})R^{b2}$, $NR^{c2}S(O)_2NR^{c2}R^{d2}$, $S(O)R^{b2}$, $S(O)NR^{c2}R^{d2}$, $S(O)_2R^{b2}$, $S(O)_2NR^{c2}R^{d2}$, $OS(O)({=}NR^{e2})R^{b2}$, and $OS(O)_2R^{b2}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, and 4-7 membered heterocycloalkyl of $R^2$ are each optionally substituted with 1, 2, 3, or 4 independently selected $R^M$ substituents;
- each $R^{a2}$, $R^{c2}$, and $R^{d2}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;
- or, any $R^{c2}$ and $R^{d2}$ attached to the same N atom, together with the N atom to which they are attached, form a 5-6 membered heteroaryl or a 4-7 membered heterocycloalkyl group;
- each $R^{b2}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;
- each $R^{e2}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;
- $R^3$ is selected from H, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, and 4-7 membered heterocycloalkyl, wherein the $C_{1-6}$ alkyl, $C_{2-6}$ alkenyl, $C_{2-6}$ alkynyl, phenyl, $C_{3-7}$ cycloalkyl, 5-6 membered heteroaryl, and 4-7 membered heterocycloalkyl of $R^3$ are each optionally substituted with 1, 2, 3, or 4 independently selected $R^M$ substituents;
- each $R^4$ is independently selected from H, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, wherein the $C_{1-6}$ alkyl, $C_{2-6}$ alkenyl, $C_{2-6}$ alkynyl, phenyl, $C_{3-7}$ cycloalkyl, 5-6 membered heteroaryl, and 4-7 membered heterocycloalkyl of $R^4$ are each optionally substituted with 1, 2, 3, or 4 independently selected $R^M$ substituents;
- or, two $R^4$ groups attached to the same carbon atom, together with the carbon atom to which they are attached, form a $C_{3-6}$ cycloalkyl, which is optionally substituted with 1, 2, 3, or 4 independently selected $R^M$ substituents;
- $R^5$ is selected from H, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, wherein the $C_{1-6}$ alkyl, $C_{2-6}$ alkenyl, $C_{2-6}$ alkynyl, phenyl, $C_{3-7}$ cycloalkyl, 5-6 membered heteroaryl, and 4-7 membered heterocycloalkyl of $R^5$ are each optionally substituted with 1, 2, 3, or 4 independently selected $R^M$ substituents;
- $R^6$ is selected from H, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, wherein the $C_{1-6}$ alkyl, $C_{2-6}$ alkenyl, $C_{2-6}$ alkynyl, phenyl, $C_{3-7}$ cycloalkyl, 5-6 membered heteroaryl, and 4-7 membered heterocycloalkyl of $R^6$ are each optionally substituted with 1, 2, 3, or 4 independently selected $R^M$ substituents;
- $R^7$ is selected from H, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a7}$, $SR^{a7}$, $NHOR^{a7}$, $C(O)R^{b7}$, $C(O)NR^{c7}R^{d7}$, $C(O)NR^{c7}(OR^{a7})$, $C(O)OR^{a7}$, $OC(O)R^{b7}$, $OC(O)NR^{c7}R^{d7}$, $NR^{c7}R^{d7}$, $NR^{c7}NR^{c7}R^{d7}$, $NR^{c7}C(O)R^{b7}$, $NR^{c7}C(O)OR^{a7}$, $NR^{c7}C(O)NR^{c7}R^{d7}$, $C(=NR^{e7})R^{b7}$, $C(=NR^{e7})NR^{c7}R^{d7}$, $C(=NOR^{a7})R^{b7}$, $C(=NOR^{a7})OR^{a7}$, $NR^{c7}C(=NR^{e7})NR^{c7}R^{d7}$, $NR^{c7}(=NR^{e7})R^{b7}$, $NR^{c7}S(O)R^{b7}$, $NR^{c7}S(O)NR^{c7}R^{d7}$, $NR^{c7}S(O)_2R^{b7}$, $NR^{c7}S(O)(=NR^{e7})R^{b7}$, $NR^{c7}S(O)_2NR^{c7}R^{d7}$, $S(O)R^{b7}$, $S(O)NR^{c7}R^{d7}$, $S(O)_2R^{b7}$, $S(O)_2NR^{c7}R^{d7}$, $OS(O)(=NR^{e7})R^{b7}$, and $OS(O)_2R^{b7}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^7$ are each optionally substituted with 1, 2, 3, 4, 5, 6, 7, or 8 independently selected $R^{7A}$ substituents;

each $R^{a7}$, $R^{c7}$, and $R^{d7}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a7}$, $R^{c7}$ and $R^{d7}$ are each optionally substituted with 1, 2, 3, 4, 5, 6, 7, or 8 independently selected $R^{7A}$ substituents;

or, any $R^{c7}$ and $R^{d7}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, 4, 5, 6, 7, or 8 independently selected $R^{7A}$ substituents;

each $R^{b7}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b7}$ are each optionally substituted with 1, 2, 3, 4, 5, 6, 7, or 8 independently selected $R^{7A}$ substituents;

each $R^{e7}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{7A}$ is independently selected from halo, oxo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a71}$, $SR^{a71}$, $NHOR^{a71}$, $C(O)R^{b71}$, $C(O)NR^{c71}R^{d71}$, $C(O)NR^{c71}(OR^{a71})$, $C(O)OR^{a71}$, $OC(O)R^{b71}$, $OC(O)NR^{c71}R^{d71}$, $NR^{c71}R^{d71}$, $NR^{c71}NR^{c71}R^{d71}$, $NR^{c71}C(O)R^{b71}$, $NR^{c71}C(O)OR^{a71}$, $NR^{c71}C(O)NR^{c71}R^{d71}$, $(=NR^{e71})R^{b71}$, $(=NR^{e71})NR^{c71}R^{d71}$, $C(=NOR^{a71})R^{b71}$, $C(=NOR^{a71})OR^{a71}$, $NR^{c71}C(=NR^{e71})NR^{c71}R^{d71}$, $NR^{c71}C(=NR^{e71})R^{b71}$, $NR^{c71}S(O)R^{b71}$, $NR^{c71}S(O)NR^{c71}R^{d71}$, $NR^{c71}S(O)_2R^{b71}$, $NR^{c71}S(O)(=NR^{e71})R^{b71}$, $NR^{c71}S(O)_2NR^{c71}R^{d71}$, $S(O)R^{b71}$, $S(O)NR^{c71}R^{d71}$, $S(O)_2R^{b71}$, $S(O)_2NR^{c71}R^{d71}$, $OS(O)(=NR^{e71})R^{b71}$, and $OS(O)_2R^{b71}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{7A}$ are each optionally substituted with 1, 2, 3, or 4 independently selected $R^M$ substituents;

each $R^{a71}$, $R^{c71}$, and $R^{d71}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a71}$, $R^{c71}$ and $R^{d71}$ are each optionally substituted with 1, 2, 3, 4, 5, 6, 7, or 8 independently selected $R^M$ substituents;

or, any $R^{c71}$ and $R^{d71}$ attached to the same N atom, together with the N atom to which they are attached, form a 5-6 membered heteroaryl or a 4-7 membered heterocycloalkyl group, wherein the 5-6 membered heteroaryl or 4-7 membered heterocycloalkyl group is optionally substituted with 1, 2, 3, or 4 independently selected $R^M$ substituents;

each $R^{b71}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{b71}$ are each optionally substituted with 1, 2, 3, 4, 5, 6, 7, or 8 independently selected R M substituents;

each $R^{e71}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

$R^8$ is selected from H, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a8}$, $SR^{a8}$, $NHOR^{a8}$, $C(O)R^{b8}$, $C(O)NR^{c8}R^{d8}$, C(O)

$NR^{c8}(OR^{a8})$, $C(O)OR^{a8}$, $OC(O)R^{b8}$, $OC(O)NR^{c8}R^{d8}$, $NR^{c8}R^{d8}$, $NR^{c8}NR^{c8}R^{d8}$, $NR^{c8}C(O)R^{b8}$, $NR^{c8}C(O)OR^{a8}$, $NR^{c8}C(O)NR^{c8}R^{d8}$, $C(=NR^{e8})R^{b8}$, $C(=NR^{e8})NR^{c8}R^{d8}$, $C(=NOR^{a8})R^{b8}$, $C(=NOR^{a8})OR^{a8}$, $NR^{c8}C(=NR^{e8})NR^{c8}R^{d8}$, $NR^{c8}C(=NR^{e8})R^{b8}$, $NR^{c8}S(O)R^{b8}$, $NR^{c8}S(O)NR^{c8}R^{d8}$, $NR^{c8}S(O)_2R^{b8}$, $NR^{c8}S(O)(=NR^{e8})R^{b8}$, $NR^{c8}S(O)_2NR^{c8}R^{d8}$, $S(O)R^{b8}$, $S(O)NR^{c8}R^{d8}$, $S(O)_2R^{b8}$, $S(O)_2NR^{c8}R^{d8}$, $OS(O)(=NR^{e8})R^{b8}$, and $OS(O)_2R^{b8}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^8$ are each optionally substituted with 1, 2, 3, 4, 5, 6, 7, or 8 independently selected $R^{8A}$ substituents;

each $R^{a8}$, $R^{c8}$, and $R^{d8}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a8}$, $R^{c8}$ and $R^{d8}$ are each optionally substituted with 1, 2, 3, 4, 5, 6, 7, or 8 independently selected $R^{8A}$ substituents;

or, any $R^{c8}$ and $R^{d8}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, 4, 5, 6, 7, or 8 independently selected $R^{8A}$ substituents;

each $R^{b8}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b8}$ are each optionally substituted with 1, 2, 3, 4, 5, 6, 7, or 8 independently selected $R^{8A}$ substituents;

each $R^{e8}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{8A}$ is independently selected from halo, oxo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a81}$, $SR^{a81}$, $NHOR^{a81}$, $C(O)R^{b81}$, $C(O)NR^{c81}R^{d81}$, $C(O)NR^{c81}(OR^{a81})$, $C(O)OR^{a81}$, $OC(O)R^{b81}$, $OC(O)NR^{c81}R^{d81}$, $NR^{c81}R^{d81}$, $NR^{c81}R^{c81}R^{d81}$, $NR^{c81}C(O)R^{b81}$, $NR^{c81}C(O)OR^{a81}$, $NR^{c81}C(O)NR^{c81}R^{d81}$, $C(=NR^{e81})R^{b81}$, $C(=NR^{e81})NR^{c81}R^{d81}$, $C(=NOR^{a81})R^{b81}$, $C(=NOR^{a81})OR^{a81}$, $NR^{c81}C(=NR^{e81})NR^{c81}R^{d81}$, $NR^{c81}C(=NR^{e81})R^{b81}$, $NR^{c81}S(O)R^{b81}$, $NR^{c81}S(O)NR^{c81}R^{d81}$, $NR^{c81}S(O)_2R^{b81}$, $NR^{c81}S(O)(=NR^{e81})R^{b81}$, $NR^{c81}S(O)^2NR^{c81}R^{d81}$, $S(O)R^{b81}$, $S(O)NR^{c81}R^{d81}$, $S(O)_2R^{b81}$, $S(O)_2NR^{c81}R^{d81}$, $OS(O)(=NR^{e81})R^{b81}$, and $OS(O)_2R^{b81}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{8A}$ are each optionally substituted with 1, 2, 3, or 4 independently selected $R^M$ substituents;

each $R^{a81}$, $R^{c81}$, and $R^{d81}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a81}$, $R^{c81}$ and $R^{d81}$ are each optionally substituted with 1, 2, 3, or 4 independently selected $R^M$ substituents;

or, any $R^{c81}$ and $R^{d81}$ attached to the same N atom, together with the N atom to which they are attached, form a 5-6 membered heteroaryl or a 4-7 membered heterocycloalkyl group, wherein the 5-6 membered heteroaryl or 4-7 membered heterocycloalkyl group is optionally substituted with 1, 2, 3, or 4 independently selected $R^M$ substituents;

each $R^{b81}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{b81}$ are each optionally substituted with 1, 2, 3, or 4 independently selected R M substituents;

each $R^{e81}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

$R^9$ is selected from H, halo, $C_{1-6}$ alkyl, $C_{1-6}$ haloalkyl, $C_{2-6}$ alkenyl, $C_{2-6}$ alkynyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a9}$, $SR^{a9}$, $NHOR^{a9}$, $C(O)R^{b9}$, $C(O)NR^{c9}R^{d9}$, $C(O)NR^{c9}(OR^{a9})$, $C(O)OR^{a9}$, $OC(O)R^{b9}$, $OC(O)NR^{c9}R^{d9}$, $NR^{c99}R^{d99}$, $NR^{c9}NR^{c9}R^{d9}$, $NR^{c9}C(=O)R^{b9}$, $NR^{c9}C(O)OR^{a9}$, $NR^{c9}C(O)NR^{c9}R^{d9}$, $C(=NR^{e9})R^{b9}$, $C(=NR^{e9})NR^{c9}R^{d9}$, $C(=NOR^{a9})R^{b9}$, $C(=NOR^{a9})OR^{a9}$, $NR^{c9}C(=NR^{e9})NR^{c9}R^{d9}$, $NR^{c9}C(=NR^{e9})R^{b9}$, $NR^{c9}S(O)R^{b9}$, $NR^{c9}S(O)NR^{c9}R^{d9}$, $NR^{c9}S(O)_2R^{b9}$, $NR^{c9}S(O)(=NR^{e9})R^{b9}$, $NR^{c9}S(O)_2NR^{c9}R^{d9}$, $S(O)R^{b9}$, $S(O)NR^{c9}R^{d9}$, $S(O)_2R^{b9}$, $S(O)_2NR^{c9}R^{d9}$, $OS(O)(=NR^{e9})R^{b9}$, and $OS(O)_2R^{b9}$, wherein the $C_{1-6}$ alkyl, $C_{2-6}$ alkenyl, $C_{2-6}$ alkynyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^9$ are each optionally substituted with 1, 2, 3, 4, 5, 6, 7, or 8 independently selected $R^{9A}$ substituents;

each $R^{a9}$, $R^{c9}$, and $R^{d9}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a9}$, $R^{c9}$ and $R^{d9}$ are each optionally substituted with 1, 2, 3, 4, 5, 6, 7, or 8 independently selected $R^{9A}$ substituents;

or, any $R^{c9}$ and $R^{d9}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, 4, 5, 6, 7, or 8 independently selected $R^{9A}$ substituents;

each $R^{c99}$ and $R^{d99}$ is independently selected from H, $C_{1-6}$ alkyl, $C_{1-6}$ haloalkyl, $C_{2-6}$ alkenyl, $C_{2-6}$ alkynyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a9}$, $R^{c9}$ and $R^{d9}$ are each optionally substituted with 1, 2, 3, 4, 5, 6, 7, or 8 independently selected $R^{9A}$ substituents;

each $R^{b9}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b9}$ are each optionally substituted with 1, 2, 3, 4, 5, 6, 7, or 8 independently selected $R^{9A}$ substituents;

each $R^{e9}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{9A}$ is independently selected from halo, oxo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a91}$, $SR^{a91}$, $NHOR^{a91}$, $C(O)R^{b91}$, $C(O)NR^{c91}R^{d91}$, $C(O)NR^{c91}(OR^{a91})$, $C(O)OR^{a91}$, $OC(O)R^{b91}$, $OC(O)NR^{c91}R^{d91}$, $NR^{c91}R^{d91}$, $NR^{c91}NR^{c91}R^{d91}$, $NR^{c91}C(O)R^{b91}$, $NR^{c91}C(O)OR^{a91}$, $NR^{c91}C(O)NR^{c91}R^{d91}$, $C(=NR^{e91})R^{b91}$, $C(=NR^{e91})NR^{c91}R^{d91}$, $C(=NOR^{a91})R^{b91}$, $C(=NOR^{a91})OR^{a91}$, $NR^{c91}C(=NR^{e91})NR^{c91}R^{d91}$, $NR^{c91}C(=NR^{e91})R^{b91}$, $NR^{c91}S(O)R^{b91}$, $NR^{c91}S(O)NR^{c91}R^{d91}$, $NR^{c91}S(O)_2R^{b91}$, $NR^{c91}S(O)(=NR^{e91})R^{b91}$, $NR^{c91}S(O)_2NR^{c91}R^{d91}$, $S(O)R^{b91}$, $S(O)NR^{c91}R^{d91}$, $S(O)_2R^{b91}$, $S(O)_2NR^{c91}R^{d91}$, $OS(O)(=NR^{e91})R^{b91}$, and $OS(O)_2R^{b91}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{9A}$ are each optionally substituted with 1, 2, 3, or 4 independently selected $R^M$ substituents;

each $R^{a91}$, $R^{c91}$, and $R^{d91}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a91}$, $R^{c91}$ and $R^{d91}$ are each optionally substituted with 1, 2, 3, or 4 independently selected $R^M$ substituents;

or, any $R^{c91}$ and $R^{d91}$ attached to the same N atom, together with the N atom to which they are attached, form a 5-6 membered heteroaryl or a 4-7 membered heterocycloalkyl group, wherein the 5-6 membered heteroaryl or 4-7 membered heterocycloalkyl group is optionally substituted with 1, 2, 3, or 4 independently selected $R^M$ substituents;

each $R^{b91}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{b91}$ are each optionally substituted with 1, 2, 3, or 4 independently selected R M substituents;

each $R^{e91}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

$R^{10}$ is selected from H, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a10}$, $SR^{a10}$, $NHOR^{a10}$, $C(O)R^{b10}$, $C(O)NR^{c10}R^{d10}$, $C(O)NR^{c10}(OR^{a10})$, $C(O)OR^{a10}$, $OC(O)R^{b10}$, $OC(O)NR^{c10}R^{d10}$, $NR^{c10}R^{d10}$, $NR^{c10}NR^{c10}R^{d10}$, $NR^{c10}C(O)R^{b10}$, $NR^{c10}C(O)OR^{a10}$, $NR^{c10}C(O)NR^{c10}R^{d10}$, $C(=NR^{e10})R^{b10}$, $C(=NR^{e10})NR^{c10}R^{d10}$, $C(=NOR^{a10})R^{b10}$, $C(=NOR^{a10})OR^{a10}$, $NR^{c10}C(=NR^{e10})NR^{c10}R^{d10}$, $NR^{c10}C(=NR^{e10})R^{b10}$, $NR^{c10}S(O)R^{b10}$, $NR^{c10}S(O)NR^{c10}R^{d10}$, $NR^{c10}S(O)_2R^{b10}$, $NR^{c10}S(O)(=NR^{e10})R^{b10}$, $NR^{c10}S(O)_2NR^{c10}R^{d10}$, $S(O)R^{b10}$, $S(O)NR^{c10}R^{d10}$, $S(O)_2R^{b10}$, $S(O)_2NR^{c10}R^{d10}$, $OS(O)(=NR^{e10})R^{b10}$, and $OS(O)_2R^{b10}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{10}$ are each optionally substituted with 1, 2, 3, 4, 5, 6, 7, or 8 independently selected $R^{10A}$ substituents;

each $R^{a10}$, $R^{c10}$, and $R^{d10}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a10}$, $R^{c10}$ and $R^{d10}$ are each optionally substituted with 1, 2, 3, 4, 5, 6, 7, or 8 independently selected $R^{10A}$ substituents;

or, any $R^{c10}$ and $R^{d10}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, 4, 5, 6, 7, or 8 independently selected $R^{10A}$ substituents;

each $R^{b10}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b10}$ are each optionally substituted with 1, 2, 3, 4, 5, 6, 7, or 8 independently selected $R^{10A}$ substituents;

each $R^{e10}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{10A}$ is independently selected from halo, oxo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a101}$, $SR^{a101}$, $NHOR^{a101}$, $C(O)R^{b101}$, $C(O)NR^{c101}R^{d101}$, $C(O)NR^{c101}(OR^{a101})$, $C(O)OR^{a101}$, $OC(O)R^{b101}$, $OC(O)NR^{c101}R^{d101}$, $NR^{c101}R^{d101}$, $NR^{c101}NR^{c101}R^{d101}$, $NR^{c101}C(O)R^{b101}$, $NR^{c101}C(O)OR^{a101}$, $NR^{c101}C(O)NR^{c101}R^{d101}$, $C(=NR^{e101})R^{b101}$, $C(=NR^{e101})NR^{c101}R^{d101}$, $C(=NOR^{a101})R^{b101}$, $C(=NOR^{a101})OR^{a101}$, $NR^{c101}C(=NR^{e101})NR^{c101}R^{d101}$, $NR^{c101}C(=NR^{e101})R^{b101}$, $NR^{c101}S(O)R^{b101}$, $NR^{c101}S(O)NR^{c101}R^{d101}$, $NR^{c101}S(O)_2R^{b101}$, $NR^{c101}S(O)(=NR^{e101})R^{b101}$, $NR^{c101}S(O)_2NR^{c101}R^{d101}$, $S(O)R^{b101}$, $S(O)NR^{c101}R^{d101}$, $S(O)_2R^{b101}$, $S(O)_2NR^{c101}R^{d101}$, $OS(O)(=NR^{e101})R^{b101}$, and $OS(O)_2R^{b101}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{10A}$ are each optionally substituted with 1, 2, 3, or 4 independently selected R M substituents;

each $R^{a101}$, $R^{c101}$, and $R^{d101}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a101}$, $R^{c101}$ and $R^{d101}$ are each optionally substituted with 1, 2, 3, or 4 independently selected $R^M$ substituents;

or, any $R^{c101}$ and $R^{d101}$ attached to the same N atom, together with the N atom to which they are attached, form a 5-6 membered heteroaryl or a 4-7 membered heterocycloalkyl group, wherein the 5-6 membered heteroaryl or 4-7 membered heterocycloalkyl group is optionally substituted with 1, 2, 3, or 4 independently selected $R^M$ substituents;

each $R^{b101}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{b101}$ are each optionally substituted with 1, 2, 3, or 4 independently selected $R^M$ substituents;

each $R^{e101}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

$L^1$ is $C_{1-3}$ alkyl, $C_{2-3}$ alkenyl, $C_{2-3}$ alkynyl, $C_{3-6}$ cycloalkyl, or 4-6 membered heterocycloalkyl;

$Cy^1$ is a $C_{6-10}$ aryl or 5-10 membered heteroaryl, wherein the $C_{6-10}$ aryl and 5-10 membered heteroaryl are each optionally substituted with 1, 2, 3, 4, 5, 6, 7, or 8 independently selected $R^{11}$ substituents;

each $R^{11}$ is independently selected from halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a11}$, $SR^{a11}$, $NHOR^{a11}$, $C(O)R^{b11}$, $C(O)NR^{c11}R^{d11}$, $C(O)NR^{c11}(OR^{a11})$, $C(O)OR^{a11}$, $OC(O)R^{b11}$, $OC(O)NR^{c11}R^{d11}$, $NR^{c11}R^{d11}$, $NR^{c11}NR^{c11}R^{d11}$, $NR^{c11}C(O)R^{b11}$, $NR^{c11}C(O)OR^{a11}$, $NR^{c11}C(O)NR^{c11}R^{d11}$, $C(=NR^{e11})R^{b11}$, $C(=NR^{e11})NR^{c11}R^{d11}$, $NR^{c11}C(=NR^{e11})NR^{c11}R^{d11}$, $NR^{c11}C(=NR^{e11})R^{b11}$, $NR^{c11}S(O)R^{b11}$, $NR^{c11}S(O)NR^{c11}R^{d11}$, $NR^{c11}S(O)_2R^{b11}$, $NR^{c11}S(O)_2NR^{c11}R^{d11}$, $S(O)R^{b11}$, $S(O)NR^{c11}R^{d11}$, $S(O)_2R^{b11}$, $S(O)_2NR^{c11}R^{d11}$, $OS(O)(=NR^{e11})R^{b11}$, and $OS(O)_2R^{b11}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{11}$ are each optionally substituted with 1, 2, 3, 4, 5, 6, 7, or 8 independently selected $R^{11A}$ substituents;

each $R^{a11}$, $R^{c11}$, and $R^{d11}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a11}$, $R^{c11}$ and $R^{d11}$ are each optionally substituted with 1, 2, 3, 4, 5, 6, 7, or 8 independently selected $R^{11A}$ substituents;

or, any $R^{c11}$ and $R^{d11}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, 4, 5, 6, 7, or 8 independently selected $R^{11A}$ substituents;

each $R^{b11}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b11}$ are each optionally substituted with 1, 2, 3, 4, 5, 6, 7, or 8 independently selected $R^{11A}$ substituents;

each $R^{e11}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{11A}$ is independently selected from halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, CN, $NO_2$, $OR^{a111}$, $C(O)NR^{c111}R^{d111}$, $C(O)OR^{a111}$, $NR^{c111}R^{d111}$, $S(O)NR^{c111}R^{d111}$, $S(O)_2R^{b111}$, $S(O)_2NR^{c111}R^{d111}$, and $OS(O)_2R^{b111}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, and 4-7 membered heterocycloalkyl of $R^{11A}$ are each optionally substituted with 1, 2, 3, or 4 independently selected $R^M$ substituents;

each $R^{a111}$, $R^{c111}$, and $R^{d111}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a111}$, $R^{c111}$ and $R^{d111}$ are each optionally substituted with 1, 2, 3, or 4 independently selected $R^M$ substituents;

or, any $R^{c111}$ and $R^{d111}$ attached to the same N atom, together with the N atom to which they are attached, form a 5-6 membered heteroaryl or a 4-7 membered heterocycloalkyl group, wherein the 5-6 membered heteroaryl or 4-7 membered heterocycloalkyl group is optionally substituted with 1, 2, 3, or 4 independently selected $R^M$ substituents;

each $R^{b111}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{b111}$ are each optionally substituted with 1, 2, 3, or 4 independently selected R M substituents;

$R^{12}$ is selected from H, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a12}$, $SR^{a12}$, $NHOR^{a12}$, $C(O)R^{b12}$, $C(O)NR^{c12}R^{d12}$, $C(O)NR^{c12}(OR^{a12})$, $C(O)OR^{a12}$, $OC(O)R^{b12}$, $OC(O)NR^{c12}R^{d12}$, $NR^{c12}R^{d12}$, $NR^{c12}NR^{c12}R^{d12}$, $NR^{c12}C(O)R^{b12}$, $NR^{c12}C(O)OR^{a12}$, $NR^{c12}C(O)NR^{c12}R_{d12}$, $C(=NR^{e12})R^{b12}$, $C(=NR^{e12})NR^{c12}R^{d12}$, $NR^{c12}C(=NR^{e12})NR^{c12}R^{d12}$, $NR^{c12}C(=NR^{e12})R^{b12}$, $NR^{c12}S(O)R^{b12}$, $NR^{c12}S(O)NR^{c12}R^{d12}$, $NR^{c12}S(O)_2R^{b12}$, $NR^{c12}S(O)(=NR^{e12})R^{b12}$, $NR^{c12}S(O)_2NR^{c12}R^{d12}$, $S(O)R^{b12}$, $S(O)NR^{c12}R^{d12}$, $S(O)_2R^{b12}$, $S(O)_2NR^{c12}R^{d12}$, $OS(O)(=NR^{e12})R^{b12}$, and $OS(O)_2R^{b12}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{12}$ are each optionally substituted with 1, 2, 3, 4, 5, 6, 7, or 8 independently selected $R^{12A}$ substituents;

each $R^{a12}$, $R^{c12}$, and $R^{d12}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a12}$, $R^{c12}$ and $R^{d12}$ are each optionally substituted with 1, 2, 3, 4, 5, 6, 7, or 8 independently selected $R^{12A}$ substituents;

or, any $R^{c12}$ and $R^{d12}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, 4, 5, 6, 7, or 8 independently selected $R^{12A}$ substituents;

each $R^{b12}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b12}$ are each optionally substituted with 1, 2, 3, 4, 5, 6, 7, or 8 independently selected $R^{12A}$ substituents;

each $R^{e12}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{12A}$ is independently selected from halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a121}$, $SR^{a121}$, $NHOR^{a121}$, $C(O)R^{b121}$, $C(O)NR^{c121}R^{d121}$, $C(O)NR^{c121}(OR^{a121})$, $C(O)OR^{a121}$, $OC(O)R^{b121}$, $OC(O)NR^{c121}R^{d121}$, $NR^{c121}R^{d121}$, $NR^{c121}NR^{c121}R^{d121}$, $NR^{c121}C(O)R^{b121}$, $NR^{c121}C(O)OR^{a121}$, $NR^{c121}C(O)NR^{c121}R^{d121}$, $C(=NR^{e121})R^{b121}$, $C(=NR^{e121})NR^{c121}R^{d121}$, $NR^{c121}C(=NR^{e121})NR^{c121}R^{d121}$, $NR^{c121}C(=NR^{e121})R^{b121}$, $NR^{c121}S(O)R^{b121}$, $NR^{c121}S(O)NR^{c121}R^{d121}$ $NR^{c121}S(O)_2R^{b121}$, $NR^{c121}S(O)(=NR^{e121})R^{b121}$, $NR^{c121}S(O)_2NR^{c121}R^{d121}$, $S(O)R^{b121}$, $S(O)NR^{c121}R^{d121}$, $S(O)_2R^{b121}$, $S(O)_2NR^{c121}R^{d121}$, $OS(O)(=NR^{e121})R^{b121}$, and $OS(O)_2R^{b121}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{12A}$ are each optionally substituted with 1, 2, 3, 4, 5, 6, 7, or 8 independently selected $R^{12B}$ substituents;

each $R^{a121}$, $R^{c121}$, and $R^{d121}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a121}$, $R^{c121}$ and $R^{d121}$ are each optionally substituted with 1, 2, 3, 4, 5, 6, 7, or 8 independently selected $R^{12B}$ substituents;

or, any $R^{c121}$ and $R^{d121}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, 4, 5, 6, 7, or 8 independently selected $R^{12B}$ substituents;

each $R^{b121}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b121}$ are each optionally substituted with 1, 2, 3, 4, 5, 6, 7, or 8 independently selected $R^{12B}$ substituents;

each $R^{e121}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{12B}$ is independently selected from halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, CN, $NO_2$, $OR^{a122}$, $C(O)NR^{c122}R^{d122}$, $C(O)OR^{a122}$, $NR^{c122}R^{d122}$, $S(O)NR^{c122}R^{d122}$, $S(O)_2R^{b122}$, $S(O)_2NR^{c122}R^{d122}$, and $OS(O)_2R^{b122}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, and 4-7 membered heterocycloalkyl of $R^{12B}$ are each optionally substituted with 1, 2, 3, or 4 independently selected $R^M$ substituents;

each $R^{a122}$, $R^{c122}$, and $R^{d122}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl- $C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a122}$, $R^{c122}$ and $R^{d122}$ are each optionally substituted with 1, 2, 3, or 4 independently selected $R^M$ substituents;

or, any $R^{c122}$ and $R^{d122}$ attached to the same N atom, together with the N atom to which they are attached, form a 5-6 membered heteroaryl or a 4-7 membered heterocycloalkyl group, wherein the 5-6 membered heteroaryl or 4-7 membered heterocycloalkyl group is optionally substituted with 1, 2, 3, or 4 independently selected $R^M$ substituents;

each $R^{b122}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{b122}$ are each optionally substituted with 1, 2, 3, or 4 independently selected R M substituents; and each $R^M$ is independently selected from H, OH, halo, oxo, CN, C(O)OH, $NH_2$, $NO_2$, $SF_5$, $C_{1-6}$ alkyl, $C_{1-6}$ alkoxy, $C_{1-6}$ haloalkoxy, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-.

In some embodiments, U is C(O) and V is $NR^6$.

In some embodiments, $R^6$ is selected from H, halo, $C_{1-6}$ alkyl, $C_{1-6}$ haloalkyl, $C_{2-6}$ alkenyl, and $C_{2-6}$ alkynyl.

In some embodiments, $R^6$ is H or $C_{1-6}$ alkyl.

In some embodiments, $R^6$ is H or $C_{1-3}$ alkyl.

In some embodiments, $R^6$ is $C_{1-6}$ alkyl.

In some embodiments, $R^6$ is $C_{1-3}$ alkyl.

In some embodiments, $R^6$ is methyl.

In some embodiments, U is O and V is C(O).

In some embodiments, W is $CR^7$ or N.

In some embodiments, $R^7$ is selected from H, halo, $C_{1-6}$ alkyl, $C_{1-6}$ haloalkyl, $C_{2-6}$ alkenyl, and $C_{2-6}$ alkynyl.

In some embodiments, $R^7$ is selected from H or $C_{1-6}$ alkyl.

In some embodiments, $R^7$ is H.

In some embodiments, W is CH or N.

In some embodiments, X is $CR^8$.

In some embodiments, $R^8$ is selected from H, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, CN, and $OR^{a8}$, wherein $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, and 4-7 membered heterocycloalkyl of $R^8$ are each optionally substituted with 1, 2, 3, or 4 independently selected $R^{8A}$ substituents.

In some embodiments, $R^8$ is selected from H, halo, $C_{1-6}$ alkyl, $C_{1-6}$ haloalkyl, $C_{2-6}$ alkenyl, $C_{2-6}$ alkynyl, and CN, wherein $C_{1-6}$ alkyl, $C_{2-6}$ alkenyl, and $C_{2-6}$ alkynyl of $R^8$ are each optionally substituted with 1, 2, 3, or 4 independently selected $R^{8A}$ substituents.

In some embodiments, each $R^{8A}$ is independently selected from halo, $C_{1-6}$ alkyl, $C_{1-6}$ haloalkyl, $C_{2-6}$ alkenyl, $C_{2-6}$ alkynyl, and CN.

In some embodiments, $R^8$ is selected from H, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, CN, and $OR^{a8}$, wherein $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, and 4-7 membered heterocycloalkyl of $R^8$ are each optionally substituted with 1, 2, 3, or 4 independently selected $R^{8A}$ substituents; and each $R^{8A}$ is independently selected from halo, $C_{1-6}$ alkyl, $C_{1-6}$ haloalkyl, $C_{2-6}$ alkenyl, $C_{2-6}$ alkynyl, and CN.

In some embodiments, $R^8$ is selected from H, halo, $C_{1-6}$ alkyl, $C_{1-6}$ haloalkyl, $C_{2-6}$ alkenyl, $C_{2-6}$ alkynyl, and CN, wherein $C_{1-6}$ alkyl, $C_{2-6}$ alkenyl, and $C_{2-6}$ alkynyl of $R^8$ are each optionally substituted with 1, 2, 3, or 4 independently selected $R^{8A}$ substituents; and each $R^{8A}$ is independently selected from halo, $C_{1-6}$ alkyl, $C_{1-6}$ haloalkyl, $C_{2-6}$ alkenyl, $C_{2-6}$ alkynyl, and CN.

In some embodiments, each $R^{8A}$ is CN.

In some embodiments, $R^8$ is selected from H, cyanomethyl, and cyano.

In some embodiments, Y is $CR^9$.

In some embodiments, $R^9$ is selected from H, halo, $C_{1-6}$ alkyl, $C_{1-6}$ haloalkyl, $C_{2-6}$ alkenyl, $C_{2-6}$ alkynyl, and CN, wherein $C_{1-6}$ alkyl, $C_{2-6}$ alkenyl, and $C_{2-6}$ alkynyl of $R^9$ are each optionally substituted with 1, 2, 3, or 4 independently selected $R^{9A}$ substituents.

In some embodiments, $R^9$ is selected from H, halo, $C_{1-6}$ alkyl, $C_{1-6}$ haloalkyl, $C_{2-6}$ alkenyl, $C_{2-6}$ alkynyl, and CN, wherein $C_{1-6}$ alkyl, $C_{2-6}$ alkenyl, and $C_{2-6}$ alkynyl of $R^9$ are each optionally substituted with 1 or 2 independently selected $R^{9A}$ substituents.

In some embodiments, each $R^{9A}$ is independently selected from halo, $C_{1-6}$ alkyl, $C_{1-6}$ haloalkyl, $C_{2-6}$ alkenyl, $C_{2-6}$ alkynyl, and CN.

In some embodiments, $R^9$ is selected from H, halo, $C_{1-6}$ alkyl, $C_{1-6}$ haloalkyl, $C_{2-6}$ alkenyl, $C_{2-6}$ alkynyl, and CN, wherein $C_{1-6}$ alkyl, $C_{2-6}$ alkenyl, and $C_{2-6}$ alkynyl of $R^9$ are each optionally substituted with 1, 2, 3, or 4 independently selected $R^{9A}$ substituents; and each $R^{9A}$ is independently selected from halo, $C_{1-6}$ alkyl, $C_{1-6}$ haloalkyl, $C_{2-6}$ alkenyl, $C_{2-6}$ alkynyl, and CN.

In some embodiments, $R^9$ is selected from H, halo, $C_{1-6}$ alkyl, $C_{1-6}$ haloalkyl, $C_{2-6}$ alkenyl, $C_{2-6}$ alkynyl, and CN, wherein $C_{1-6}$ alkyl, $C_{2-6}$ alkenyl, and $C_{2-6}$ alkynyl of $R^9$ are each optionally substituted with 1 or 2 independently selected $R^{9A}$ substituents; and each $R^{9A}$ is independently selected from halo, $C_{1-6}$ alkyl, $C_{1-6}$ haloalkyl, $C_{2-6}$ alkenyl, $C_{2-6}$ alkynyl, and CN.

In some embodiments, each $R^{9A}$ is CN.

In some embodiments, $R^9$ is selected from H, cyanomethyl, and cyano.

In some embodiments, Z is $CR^{10}$.

In some embodiments, $R^{10}$ is selected from H, halo, $C_{1-6}$ alkyl, $C_{1-6}$ haloalkyl, $C_{2-6}$ alkenyl, and $C_{2-6}$ alkynyl.

In some embodiments, $R^{10}$ is selected from H and $C_{1-6}$ alkyl.

In some embodiments, Z is CH.

In some embodiments, Z is N.

In some embodiments, n is 0 or 1.

In some embodiments, n is 0.

In some embodiments, n is 1.

In some embodiments, each $R^2$ is independently selected from halo, $C_{1-6}$ alkyl, $C_{1-6}$ haloalkyl, $C_{2-6}$ alkenyl, and $C_{2-6}$ alkynyl.

In some embodiments, each $R^2$ is independently selected from $C_{1-6}$ alkyl.

In some embodiments, each $R^2$ is independently selected from $C_{1-3}$ alkyl.

In some embodiments, each $R^2$ is methyl.

In some embodiments, $R^3$ is selected from H, halo, $C_{1-6}$ alkyl, $C_{1-6}$ haloalkyl, $C_{2-6}$ alkenyl, and $C_{2-6}$ alkynyl.

In some embodiments, $R^3$ is selected from H and $C_{1-6}$ alkyl.

In some embodiments, $R^3$ is selected from H and $C_{1-3}$ alkyl.

In some embodiments, $R^3$ is methyl.

In some embodiments, each $R^4$ is independently selected from H, halo, $C_{1-6}$ alkyl, $C_{1-6}$ haloalkyl, $C_{2-6}$ alkenyl, and $C_{2-6}$ alkynyl.

In some embodiments, each $R^4$ is independently selected from H and $C_{1-6}$ alkyl.

In some embodiments, each $R^4$ is H.

In some embodiments, $L^1$ is $C_{1-3}$ alkyl.

In some embodiments, $L^1$ is CH.

In some embodiments, $Cy^1$ is phenyl or 5-6 membered heteroaryl, wherein the phenyl and 5-6 membered heteroaryl of $Cy^1$ are each optionally substituted with 1, 2, 3, or 4 independently selected $R^{11}$ substituents.

In some embodiments, $Cy^1$ is phenyl, which is optionally substituted with 1, 2, 3, or 4 independently selected $R^{11}$ substituents.

In some embodiments, each $R^{11}$ is independently selected from halo, $C_{1-6}$ alkyl, $C_{1-6}$ haloalkyl, $C_{2-6}$ alkenyl, and $C_{2-6}$ alkynyl.

In some embodiments, each $R^{11}$ is independently selected from halo.

In some embodiments, each $R^{11}$ is fluoro.

In some embodiments, $Cy^1$ is fluorophenyl.

In some embodiments, $Cy^1$ is 4-fluorophenyl.

In some embodiments, $R^{12}$ is phenyl or 5-6 membered heteroaryl, wherein the phenyl and 5-6 membered heteroaryl of $R^{12}$ are each optionally substituted with 1, 2, 3, or 4 independently selected $R^{12A}$ substituents.

In some embodiments, $R^{12}$ is phenyl, which is optionally substituted with 1, 2, 3, or 4 independently selected $R^{12A}$ substituents.

In some embodiments, each $R^{12A}$ is independently selected from halo, $C_{1-6}$ alkyl, $C_{1-6}$ haloalkyl, $C_{2-6}$ alkenyl, and $C_{2-6}$ alkynyl.

In some embodiments, each $R^{12A}$ is independently selected from halo.

In some embodiments, each $R^{12A}$ is fluoro.

In some embodiments, $R^{12}$ is fluorophenyl.

In some embodiments, $R^{12}$ is 4-fluorophenyl.

In some embodiments, $Cy^1$ and $R^{12}$ are each 4-fluorophenyl.

In some embodiments:

$\overset{\text{---}}{=\!=}$ is a single or double bond;

U is O and V is C(O); or

U is C(O) and V is $NR^6$;

W is $CR^7$ or N;

X is $CR^8$;

Y is $CR^9$;

Z is $CR^{10}$ or N;

each $R^2$ is independently selected from halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, CN, $NO_2$, $OR^{a2}$, $NHOR^{a2}$, $C(O)R^{b2}$, $C(O)NR^{c2}R^{d2}$, $C(O)NR^{c2}(OR^{a2})$, $C(O)OR^{a2}$, $OC(O)R^{b2}$, $OC(O)NR^{c2}R^{d2}$, $NR^{c2}R^{d2}$, $NR^{c2}NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NR^{e2})NR^{c2}R^{d2}$, $NR^{c2}C(=NR^{e2})NR^{c2}R^{d2}$, $NR^{c2}C(=NR^{e2})R^{b2}$, $NR^{c2}S(O)R^{b2}$, $N^{c2}S(O)NR^{c2}R^{d2}$, $NR^{c2}S(O)_2R^{b2}$, $NR^{c2}S(O)(=NR^{e2})R^{b2}$, $NR^{c2}S(O)_2NR^{c2}R^{d2}$, $S(O)R^{b2}$, $S(O)NR^{c2}R^{d2}$, $S(O)_2R^{b2}$, $S(O)_2NR^{c2}R^{d2}$, $OS(O)(=NR^{e2})R^{b2}$, and $OS(O)_2R^{b2}$;

each $R^{a2}$, $R^{c2}$, and $R^{d2}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

or, any $R^{c2}$ and $R^{d2}$ attached to the same N atom, together with the N atom to which they are attached, form a 5-6 membered heteroaryl or a 4-7 membered heterocycloalkyl group;

each $R^{b2}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

each $R^{e2}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

$R^3$ is selected from H, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, and 4-7 membered heterocycloalkyl, wherein the $C_{1-6}$ alkyl, $C_{2-6}$ alkenyl, $C_{2-6}$ alkynyl, phenyl, $C_{3-7}$ cycloalkyl, 5-6 membered heteroaryl, and 4-7 membered heterocycloalkyl of $R^3$ are each optionally substituted with 1, 2, 3, or 4 independently selected $R^M$ substituents;

each $R^4$ is independently selected from H, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, wherein the $C_{1-6}$ alkyl, $C_{2-6}$ alkenyl, $C_{2-6}$ alkynyl, phenyl, $C_{3-7}$ cycloalkyl, 5-6 membered heteroaryl, and 4-7 membered heterocycloalkyl of $R^4$ are each optionally substituted with 1, 2, 3, or 4 independently selected $R^M$ substituents;

or, two $R^4$ groups attached to the same carbon atom, together with the carbon atom to which they are attached, form a $C_{3-6}$ cycloalkyl, which is optionally substituted with 1, 2, 3, or 4 independently selected $R^M$ substituents;

$R^6$ is selected from H, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, wherein the $C_{1-6}$ alkyl, $C_{2-6}$ alkenyl, $C_{2-6}$ alkynyl, phenyl, $C_{3-7}$ cycloalkyl, 5-6 membered heteroaryl, and 4-7 membered heterocycloalkyl of $R^6$ are each optionally substituted with 1, 2, 3, or 4 independently selected $R^M$ substituents;

$R^7$ is selected from H, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a7}$, $SR^{a7}$, $NHOR^{a7}$, $C(O)R^{b7}$, $C(O)NR^{c7}R^{d7}$, $C(O)NR^{c7}(OR^{a7})$, $C(O)OR^{a7}$, $OC(O)R^{b7}$, $OC(O)NR^{c7}R^{d7}$, $NR^{c7}R^{d7}$, $NR^{c7}NR^{c7}R^{d7}$, $NR^{c7}C(O)R^{b7}$, $NR^{c7}C(O)OR^{a7}$, $NR^{c7}C(O)NR^{c7}R^{d7}$, $C(=NR^{e7})R^{b7}$, $C(=NR^{e7})NR^{c7}R^{d7}$, $C(=NOR^{a7})R^{b7}$, $C(=NOR^{a7})OR^{a7}$, $NR^{c7}C$ $(=NR^{e7})NR^{c7}R^{d7}$, $NR^{c7}C(=NR^{e7})R^{b7}$, $NR^{c7}S(O)R^{b7}$, $NR^{c7}S(O)NR^{c7}R^{d7}$, $NR^{c7}S(O)_2R^{b7}$, $NR^{c7}S(O)(=NR^{e7})R^{b7}$, $NR^{c7}S(O)_2NR^{c7}R^{d7}$, $S(O)R^{b7}$, $S(O)NR^{c7}R^{d7}$, $S(O)_2R^{b7}$, $S(O)_2NR^{c7}R^{d7}$, $OS(O)(=NR^{e7})R^{b7}$, and $OS(O)_2R^{b7}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^7$ are each optionally substituted with 1, 2, 3, or 4 independently selected $R^{7A}$ substituents;

each $R^{a7}$, $R^{c7}$, and $R^{d7}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a7}$, $R^{c7}$ and $R^{d7}$ are each optionally substituted with 1, 2, 3, or 4 independently selected $R^{7A}$ substituents;

or, any $R^{c7}$ and $R^{d7}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{7A}$ substituents;

each $R^{b7}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b7}$ are each optionally substituted with 1, 2, 3, or 4 independently selected $R^{7A}$ substituents;

each $R^{e7}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{7A}$ is independently selected from halo, oxo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a71}$, $SR^{a71}$, $NHOR^{a71}$, $C(O)R^{b71}$, $C(O)NR^{c71}R^{d71}$, $C(O)NR^{c71}(OR^{a71})$, $C(O)OR^{a71}$, $OC(O)R^{b71}$, $OC(O)NR^{c71}R^{d71}$, $NR^{c71}R^{d71}$, $NR^{c71}NR^{c71}R^{d71}$, $NR^{c71}C(O)R^{b71}$, $NR^{c71}C(O)OR^{a71}$, $NR^{c71}C(O)NR^{c71}R^{d71}$, $(=NR^{e71})R^{b71}$, $(=NR^{e71})NR^{c71}R^{d71}$, $C(=NOR^{a71})R^{b71}$, $C(=NOR^{a71})OR^{a71}$, $NR^{c71}c(=NR^{e71})NR^{c71}R^{d71}$, $NR^{c71}c(=NR^{e71})R^{b71}$, $NR^{c71}S(O)R^{b71}$, $NR^{c71}S(O)NR^{c71}R^{d71}$, $NR^{c71}S(O)_2R^{b71}$, $NR^{c71}S(O)(=NR^{e71})R^{b71}$, $NR^{c71}S(O)_2NR^{c71}R^{d71}$, $S(O)R^{b71}$, $S(O)NR^{c71}R^{d71}$, $S(O)_2R^{b71}$, $S(O)_2NR^{c71}R^{d71}$, $OS(O)(=NR^{e71})R^{b71}$, and $OS(O)_2R^{b71}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{7A}$ are each optionally substituted with 1, 2, 3, or 4 independently selected $R^M$ substituents;

each $R^{a71}$, $R^{c71}$, and $R^{d71}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a71}$, $R^{c71}$ and $R^{d71}$ are each optionally substituted with 1, 2, 3, or 4 independently selected $R^M$ substituents;

or, any $R^{c71}$ and $R^{d71}$ attached to the same N atom, together with the N atom to which they are attached, form a 5-6 membered heteroaryl or a 4-7 membered heterocycloalkyl group, wherein the 5-6 membered heteroaryl or 4-7 membered heterocycloalkyl group is optionally substituted with 1, 2, 3, or 4 independently selected $R^M$ substituents;

each $R^{b71}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{b71}$ are each optionally substituted with 1, 2, 3, or 4 independently selected R M substituents;

each $R^{e71}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

$R^8$ is selected from H, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a1}$, $SR^{a8}$, $NHOR^{a8}$, $C(O)R^{b8}$, $C(O)NR^{c8}R^{d8}$, $C(O)NR^{c8}(OR^{a8})$, $C(O)OR^{a8}$, $OC(O)R^{b8}$, $OC(O)NR^{c8}R^{d8}$, $NR^{c8}R^{d8}$, $NR^{c8}NR^{c8}R^{d8}$, $NR^{c8}C(O)R^{b8}$, $NR^{c8}C(O)OR^{a8}$, $NR^{c8}C(O)NR^{c8}R^{d8}$, $C(=NR^{e8})R^{b8}$, $C(=NR^{e8})NR^{c8}R^{d8}$, $C(=NOR^{a8})R^{b8}$, $C(=NOR^{a8})OR^{a8}$, $NR^{c8}C(=NR$ es$)NR^{c8}R^{d8}$, $NR^{c8}C(=NR^{e8})R^{b8}$ $NR^{c8}S(O)R^{b8}$, $NR^{c8}S(O)NR^{c8}R^{d8}$, $NR^{c8}S(O)_2R^{b8}$, $NR^{c8}S(O)(=NR^{e8})R^{b8}$, $NR^{c8}S(O)_2NR^{c8}R^{d8}$, $S(O)R^{b8}$, $S(O)NR^{c8}R^{d8}$, $S(O)_2R^{b8}$, $S(O)_2NR^{c8}R^{d8}$, $OS(O)(=NR^{e8})$ $R^{b8}$, and $OS(O)_2R^{b8}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^8$ are each optionally substituted with 1, 2, 3, or 4 independently selected $R^{8A}$ substituents;

each $R^{a8}$, $R^{c8}$, and $R^{d8}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a8}$, $R^{c8}$ and $R^{d8}$ are each optionally substituted with 1, 2, 3, or 4 independently selected $R^{8A}$ substituents;

or, any $R^{c8}$ and $R^{d8}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{8A}$ substituents;

each $R^{b8}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b8}$ are each optionally substituted with 1, 2, 3, or 4 independently selected $R^{8A}$ substituents;

each $R^{e8}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{8A}$ is independently selected from halo, oxo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a81}$, $SR^{a81}$, $NHOR^{a81}$, $C(O)R^{b81}$, $C(O)NR^{c81}R^{d81}$, $C(O)NR^{c81}(OR^{a81})$, $C(O)OR^{a81}$, $OC(O)R^{b81}$, $OC(O)NR^{c81}R^{d81}$, $NR^{c81}R^{d81}$, $NR^{c81}NR^{c81}R^{d81}$, $NR^{c81}C(O)R^{b81}$, $NR^{c81}C(O)OR^{a81}$, $NR^{c81}C(O)NR^{c81}R^{d81}$, $C(=NR^{e81})R^{b81}$, $C(=NR^{e81})NR^{c81}R^{d81}$, $C(=NOR^{a81})R^{b81}$, $C(=NOR^{a81})OR^{a81}$, $NR^{c81}C(=NR^{e81})NR^{c81}R^{d81}$, $NR^{c81}C(=NR^{e81})R^{b81}$, $NR^{c81}S(O)R^{b81}$, $NR^{c81}S(O)NR^{c81}R^{d81}$, $NR^{c81}S(O)_2R^{b81}$, $NR^{c81}S(O)(=NR^{e81})R_{b81}$, $NR^{c81}S(O)_2NR^{c81}R^{d81}$, $S(O)R^{b81}$, $S(O)NR^{c81}R^{d81}$, $S(O)_2R^{b81}$, $S(O)_2NR^{c81}R^{d81}$, $OS(O)(=NR^{e81})R^{b81}$, and $OS(O)_2R^{b81}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{8A}$ are each optionally substituted with 1, 2, 3, or 4 independently selected $R^M$ substituents;

each $R^{a81}$, $R^{c81}$ and $R^{d81}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a81}$, $R^{c81}$ and $R^{d81}$ are each optionally substituted with 1, 2, 3, or 4 independently selected $R^M$ substituents;

or, any $R^{c81}$ and $R^{d81}$ attached to the same N atom, together with the N atom to which they are attached, form a 5-6 membered heteroaryl or a 4-7 membered heterocycloalkyl group, wherein the 5-6 membered heteroaryl or 4-7 membered heterocycloalkyl group is optionally substituted with 1, 2, 3, or 4 independently selected $R^M$ substituents;

each $R^{b81}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{b81}$ are each optionally substituted with 1, 2, 3, or 4 independently selected R M substituents;

each $R^{e81}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

$R^9$ is selected from H, halo, $C_{1-6}$ alkyl, $C_{1-6}$ haloalkyl, $C_{2-6}$ alkenyl, $C_{2-6}$ alkynyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a9}$, $SR^{a9}$, $NHOR^{a9}$, $C(O)R^{b9}$, $C(O)NR^{c9}R^{d9}$, $C(O)NR^{c9}(OR^{a9})$, $C(O)OR^{a9}$, $OC(O)R^{b9}$, $OC(O)NR^{c9}R^{d9}$, $NR^{c99}R^{d99}$, $NR^{c9}NR^{c9}R^{d9}$, $NR^{c9}C(O)OR^{b9}$, $NR^{c9}C(O)OR^{a9}$, $NR^{c9}C(O)NR^{c9}R^{d9}$, $C(=NR^{e9})R^{b9}$, $C(=NR^{e9})NR^{c9}R^{d9}$, $C(=NOR^{a9})R^{b9}$, $C(=NOR^{a9})OR^{a9}$, $NR^{c9}C(=NR^{e9})NR^{c9}R^{d9}$, $NR^{c9}C(=NR^{e9})R^{b9}$, $NR^{c9}S(O)R^{b9}$, $NR^{c9}S(O)NR^{c9}R^{d9}$, $NR^{c9}S(O)_2R^{b9}$, $NR^{c9}S(O)(=NR^{e9})R^{b9}$, $NR^{c9}S(O)_2NR^{c9}R^{d9}$, $S(O)R^{b9}$, $S(O)NR^{c9}R^{d9}$, $S(O)_2R^{b9}$, $S(O)_2NR^{c9}R^{d9}$, $OS(O)(=NR^{e9})R^{b9}$, and $OS(O)_2R^{b9}$, wherein the $C_{1-6}$ alkyl, $C_{2-6}$ alkenyl, $C_{2-6}$ alkynyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^9$ are each optionally substituted with 1, 2, 3, or 4 independently selected $R^{9A}$ substituents;

each $R^{a9}$, $R^{c9}$, and $R^{d9}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a9}$, $R^{c9}$ and $R^{d9}$ are each optionally substituted with 1, 2, 3, or 4 independently selected $R^{9A}$ substituents;

or, any $R^{c9}$ and $R^{d9}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{9A}$ substituents;

each $R^{c99}$ and $R^{d99}$ is independently selected from H, $C_{1-6}$ alkyl, $C_{1-6}$ haloalkyl, $C_{2-6}$ alkenyl, $C_{2-6}$ alkynyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a9}$, $R^{c9}$ and $R^{d9}$ are each optionally substituted with 1, 2, 3, 4, 5, 6, 7, or 8 independently selected $R^{9A}$ substituents;

each $R^{b9}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b9}$ are each optionally substituted with 1, 2, 3, or 4 independently selected $R^{9A}$ substituents;

each $R^{e9}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{9A}$ is independently selected from halo, $C_{1-6}$ alkyl, $C_{1-6}$ haloalkyl, $C_{2-6}$ alkenyl, $C_{2-6}$ alkynyl, and CN;

$R^{10}$ is selected from H, halo, $C_{1-6}$ alkyl, $C_{1-6}$ haloalkyl, $C_{2-6}$ alkenyl, and $C_{2-6}$ alkynyl;

$L^1$ is $C_{1-3}$ alkyl;

$Cy^1$ is phenyl or 5-6 membered heteroaryl, wherein the phenyl or 5-6 membered heteroaryl are each optionally substituted with 1, 2, 3, or 4 independently selected $R^{11}$ substituents;

each $R^{11}$ is independently selected from halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a11}$, $SR^{a11}$, $NHOR^{a11}$, $C(O)NR^{c11}R^{d11}$, $C(O)NR^{c11}(OR^{a11})$, $C(O)OR^{a11}$, $OC(O)NR^{c11}R^{d11}$, $NR^{c11}R^{d11}$, $NR^{c11}NR^{c11}R^{d11}$, $NR^{c11}C(O)R^{b11}$, $NR^{c11}C(O)OR^{a11}$, $NR^{c11}C(O)NR^{c11}R^{d11}$, $C(=NR^{e11})R^{b11}$, $C(=NR^{e11})NR^{c11}R^{d11}$, $NR^{c11}C(=NR^{e11})NR^{c11}R^{d11}$, $NR^{c11}C(=NR^{e11})R^{b11}$, $NR^{c11}S(O)R^{b11}$, $NR^{c11}S(O)NR^{c11}R^{d11}$, $NR^{c11}S(O)_2R^{b11}$, $NR^{c11}S(O)_2NR^{c11}R^{d11}$, $S(O)R^{b11}$, $S(O)NR^{c11}R^{d11}$, $S(O)_2R^{b11}$, $S(O)_2NR^{c11}R^{d11}$, $OS(O)(=NR^{e11})R^{b11}$, and $OS(O)_2R^{b11}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{11}$ are each optionally substituted with 1, 2, 3, or 4 independently selected $R^{11A}$ substituents;

each $R^{a11}$, $R^{c11}$, and $R^{d11}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a11}$, $R^{c11}$ and $R^{d11}$ are each optionally substituted with 1, 2, 3, or 4 independently selected $R^{11A}$ substituents;

or, any $R^{c11}$ and $R^{d11}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{11A}$ substituents;

each $R^{b11}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b11}$ are each optionally substituted with 1, 2, 3, or 4 independently selected $R^{11A}$ substituents;

each $R^{e11}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{11A}$ is independently selected from halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, CN, $NO_2$, $OR^{a111}$, $C(O)NR^{c111}R^{d111}$, C(O)OR$^{a111}$, NR$^{c111}$R$^{d111}$, S(O)NR$^{c111}$R$^{d111}$, S(O)$_2$R$^{b111}$, S(O)$_2$NR$^{c111}$R$^{d111}$, and OS(O)$_2$R$^{b111}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, and 4-7 membered heterocycloalkyl of R$^{11A}$ are each optionally substituted with 1, 2, 3, or 4 independently selected R$^M$ substituents;

each R$^{a111}$, R$^{c111}$, and R$^{d111}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of R$^{a111}$, R$^{c111}$ and R$^{d111}$ are each optionally substituted with 1, 2, 3, or 4 independently selected R$^M$ substituents;

or, any R$^{c111}$ and R$^{d111}$ attached to the same N atom, together with the N atom to which they are attached, form a 5-6 membered heteroaryl or a 4-7 membered heterocycloalkyl group, wherein the 5-6 membered heteroaryl or 4-7 membered heterocycloalkyl group is optionally substituted with 1, 2, 3, or 4 independently selected R$^M$ substituents;

each R$^{b111}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of R$^{b111}$ are each optionally substituted with 1, 2, 3, or 4 independently selected R M substituents;

R$^{12}$ is selected from H, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, NO$_2$, OR$^{a12}$, SR$^{a12}$, NHOR$^{a12}$, C(O)R$^{b12}$, C(O)NR$^{c12}$R$^{d12}$, C(O)NR$^{c12}$(OR$^{a12}$), C(O)OR$^{a12}$, OC(O)R$^{b12}$, OC(O)NR$^{c12}$R$^{d12}$, NR$^{c12}$R$^{d12}$, NR$^{c12}$NR$^{c12}$R$^{d12}$, NR$^{c12}$C(O)R$^{b12}$NR$^{c12}$, C(O)OR$^{a12}$, NR$^{c12}$C(O)NR$^{c12}$R$^{d12}$, C(=NR$^{e12}$)R$^{b12}$, C(=NR$^{e12}$)NR$^{c12}$R$^{d12}$, NR$^{c12}$C(=NR$^{e12}$)NR$^{c12}$R$^{d2}$, NR$^{c12}$C(=NR$^{e12}$)R$^{b12}$, NR$^{c12}$S(O)R$^{b12}$, NR$^{c12}$S(O)NR$^{c12}$R$^{d12}$, NR$^{c12}$S(O)$_2$R$^{b12}$, NR$^{c12}$S(O)(=NR$^{e12}$)R$^{b12}$, NR$^{c12}$S(O)$_2$NR$^{c12}$R$^{d12}$, S(O) R$^{b12}$, S(O)NR$^{c12}$R$^{d12}$, S(O)$_2$R$^{b12}$, S(O)$_2$NR$^{c12}$R$^{d12}$, OS(O)(=NR$^{e12}$)R$^{b12}$, and OS(O)$_2$R$^{b12}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of R$^{12}$ are each optionally substituted with 1, 2, 3, or 4 independently selected R$^{12A}$ substituents;

each R$^{a12}$, R$^{c12}$, and R$^{d12}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of R$^{a12}$, R$^{c12}$ and R$^{d12}$ are each optionally substituted with 1, 2, 3, or 4 independently selected R$^{12A}$ substituents;

or, any R$^{c12}$ and R$^{d12}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected R$^{12A}$ substituents;

each R$^{b12}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of R$^{b12}$ are each optionally substituted with 1, 2, 3, or 4 independently selected R$^{12A}$ substituents;

each R$_{e12}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each R$^{12A}$ is independently selected from halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, NO$_2$, OR$^{a121}$, SR$^{a121}$, NHOR$^{a121}$, C(O)R$^{b121}$, C(O)NR$^{c121}$R$^{d121}$, C(O)NR$^{c121}$(OR$^{a121}$), C(O)OR$^{a121}$, OC(O)R$^{b121}$, OC(O)NR$^{c121}$R$^{d121}$, NR$^{c121}$R$^{d121}$, NR$^{c121}$NR$^{c121}$R$^{d121}$, NR$^{c121}$C(O)R$^{b121}$, NR$^{c121}$C(O)R$^{a121}$, NR$^{c121}$C(O)NR$^{c121}$R$^{d121}$, C(=NR$^{e121}$)R$^{b121}$, C(=NR$^{e121}$)NR$^{c121}$R$^{d121}$, NR$^{c121}$C(=NR$^{e121}$)NR$^{c121}$R$^{d121}$, NR$^{c121}$C(=NR$^{e121}$)R$^{b121}$, NR$^{c121}$S(O)R$^{b121}$, NR$^{c121}$S(O)NR$^{c121}$R$^{d121}$, NR$^{c121}$S(O)$_2$R$^{b121}$, NR$^{c121}$S(O)(=NR$^{e121}$)R$^{b121}$, NR$^{c121}$S(O)$_2$NR$^{c121}$R$^{d121}$, S(O)R$^{b121}$, S(O)NR$^{c121}$R$^{d121}$, S(O)$_2$R$^{b121}$, S(O)$_2$NR$^{c121}$R$^{d121}$, OS(O)(=NR$^{e121}$)R$^{b121}$, and OS(O)$_2$R$^{b121}$;

each R$^{a121}$, R$^{c121}$, and R$^{d121}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

or, any $R^{c121}$ and $R^{d121}$ attached to the same N atom, together with the N atom to which they are attached, form a 5-10 membered heteroaryl or a 4-10 membered heterocycloalkyl group;

each $R^{b121}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{e121}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-; and each $R^{M}$ is independently selected from H, OH, halo, oxo, CN, C(O)OH, $NH_2$, $NO_2$, $SF_5$, $C_{1-6}$ alkyl, $C_{1-6}$ alkoxy, $C_{1-6}$ haloalkoxy, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-.

In some embodiments:

$\overline{\overline{---}}$ is a single or double bond;

U is O and V is C(O); or

U is C(O) and V is $NR^6$;

W is CH or N;

X is $CR^8$;

Y is $CR^9$ or N;

Z is CH or N;

n is 0 or 1;

each $R^2$ is independently selected from halo, $C_{1-6}$ alkyl, $C_{1-6}$ haloalkyl, $C_{2-6}$ alkenyl, and $C_{2-6}$ alkynyl;

$R^3$ is selected from H, halo, $C_{1-6}$ alkyl, $C_{1-6}$ haloalkyl, $C_{2-6}$ alkenyl, and $C_{2-6}$ alkynyl;

each $R^4$ is independently selected from H, halo, $C_{1-6}$ alkyl, $C_{1-6}$ haloalkyl, $C_{2-6}$ alkenyl, and $C_{2-6}$ alkynyl;

$R^6$ is selected from H, halo, $C_{1-6}$ alkyl, $C_{1-6}$ haloalkyl, $C_{2-6}$ alkenyl, and $C_{2-6}$ alkynyl, wherein the $C_{1-6}$ alkyl, $C_{2-6}$ alkenyl, and $C_{2-6}$ alkynyl of $R^6$ are each optionally substituted with 1, 2, 3, or 4 independently selected $R^{M}$ substituents;

$R^8$ is selected from H, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, CN, and $OR^{a8}$, wherein $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, and 4-7 membered heterocycloalkyl of $R^8$ are each optionally substituted with 1, 2, 3, or 4 independently selected $R^{8A}$ substituents;

each $R^{8A}$ is independently selected from halo, $C_{1-6}$ alkyl, $C_{1-6}$ haloalkyl, $C_{2-6}$ alkenyl, $C_{2-6}$ alkynyl, and CN $R^9$ is selected from H, halo, $C_{1-6}$ alkyl, $C_{1-6}$ haloalkyl, $C_{2-6}$ alkenyl, $C_{2-6}$ alkynyl, and CN, wherein $C_{1-6}$ alkyl, $C_{2-6}$ alkenyl, and $C_{2-6}$ alkynyl of $R^9$ are each optionally substituted with 1, 2, 3, or 4 independently selected $R^{9A}$ substituents;

each $R^{9A}$ is independently selected from halo, $C_{1-6}$ alkyl, $C_{1-6}$ haloalkyl, $C_{2-6}$ alkenyl, $C_{2-6}$ alkynyl, and CN;

$L^1$ is $C_{1-3}$ alkyl;

$Cy^1$ is phenyl or 5-6 membered heteroaryl, wherein the phenyl or 5-6 membered heteroaryl are each optionally substituted with 1, 2, 3, or 4 independently selected $R^{11}$ substituents;

each $R^{11}$ is independently selected from halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $SR^{a11}$, $NHOR^{a11}$, $C(O)NR^{c11}R^{d11}$, $C(O)NR^{c11}(OR^{a11})$, $C(O)OR^{a11}$, $OC(O)R^{b11}$, $OC(O)NR^{c11}R^{d11}$, $NR^{c11}R^{d11}$, $NR^{c11}NR^{c11}R^{d11}$, $NR^{c11}C(O)R^{b11}$, $NR^{c11}C(O)OR^{a11}$, $NR^{c11}C(O)NR^{c11}R^{d11}$, $C(=NR^{e11})R^{b11}$, $C(=NR^{e11})NR^{c11}R^{d11}$, $NR^{c11}C(=NR^{e11})NR^{c11}R^{d11}$, $NR^{c11}C(=NR^{e11})R^{b11}$, $NR^{c11}S(O)R^{b11}$, $NR^{c11}S(O)NR^{c11}R^{d11}$, $NR^{c11}S(O)_2R^{b11}$, $NR^{c11}S(O)_2NR^{c11}R^{d11}$, $S(O)R^{b11}$, $S(O)R^{c11}R^{d11}$, $S(O)_2R^{b11}$, $S(O)_2NR^{c11}R^{d11}$, $OS(O)(=NR^{e11})R^{b11}$, and $OS(O)_2R^{b11}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{11}$ are each optionally substituted with 1, 2, 3, or 4 independently selected $R^{11A}$ substituents;

each $R^{a11}$, $R^{c11}$ and $R^{d11}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a11}$, $R^{c11}$ and $R^{d11}$ are each optionally substituted with 1, 2, 3, or 4 independently selected $R^{11A}$ substituents;

or, any $R^{c11}$ and $R^{d11}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{11A}$ substituents;

each $R^{b11}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b11}$ are each optionally substituted with 1, 2, 3, or 4 independently selected $R^{11A}$ substituents;

each $R^{e11}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{11A}$ is independently selected from halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, CN, $NO_2$, $OR^{a111}$, $C(O)NR^{c111}R^{d111}$, $C(O)OR^{a111}$, $NR^{c111}R^{d111}$, $S(O)NR^{c111}R^{d111}$, $S(O)_2R^{b111}$, $S(O)_2NR^{c111}R^{d111}$, and $OS(O)_2R^{b111}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, and 4-7 membered heterocycloalkyl of $R^{11A}$ are each optionally substituted with 1, 2, 3, or 4 independently selected $R^M$ substituents;

each $R^{a111}$, $R^{c111}$, and $R^{d111}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a111}$, $R^{c111}$ and $R^{d111}$ are each optionally substituted with 1, 2, 3, or 4 independently selected $R^M$ substituents;

or, any $R^{c111}$ and $R^{d111}$ attached to the same N atom, together with the N atom to which they are attached, form a 5-6 membered heteroaryl or a 4-7 membered heterocycloalkyl group, wherein the 5-6 membered heteroaryl or 4-7 membered heterocycloalkyl group is optionally substituted with 1, 2, 3, or 4 independently selected $R^M$ substituents;

each $R^{b111}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{b111}$ are each optionally substituted with 1, 2, 3, or 4 independently selected $R^M$ substituents;

$R^{12}$ is selected from H, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a12}$, $SR^{a12}$, $NHOR^{a12}$, $C(O)R^{b12}$, $C(O)NR^{c12}R^{d12}$, $C(O)NR^{c12}(OR^{a12})$, $C(O)OR^{a12}$, $OC(O)R^{b12}$, $OC(O)NR^{c12}R^{d12}$, $NR^{c12}R^{d12}$, $NR^{c12}NR^{c12}R^{d12}$, $NR^{c12}C(O)R^{b12}NR^{c12}$, $C(O)OR^{a12}$, $NR^{c12}C(O)NR^{c12}R^{d12}$, $C(=NR^{e12})R^{b12}$, $C(=NR^{e12})NR^{c12}R^{d12}$, $NR^{c12}C(=NR^{e12})NR^{c12}R^{d12}$, $NR^{c12}C(=NR^{e12})R^{b12}$, $NR^{c12}S(O)R^{b12}$, $NR^{c12}S(O)NR^{c12}R^{d12}$, $NR^{c12}S(O)_2R^{b12}$, $NR^{c12}S(O)(=NR^{e12})R^{b12}$, $NR^{c12}S(O)_2NR^{c12}R^{d12}$, $S(O)R^{b12}$, $S(O)NR^{c12}R^{d12}$, $S(O)_2R^{b12}$, $S(O)_2NR^{c12}R^{d12}$, $OS(O)(=NR^{e12})R^{b12}$, and $OS(O)_2R^{b12}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{12}$ are each optionally substituted with 1, 2, 3, or 4 independently selected $R^{12A}$ substituents;

each $R^{a12}$, $R^{c12}$, and $R^{d12}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a12}$, $R^{c12}$ and $R^{d12}$ are each optionally substituted with 1, 2, 3, or 4 independently selected $R^{12A}$ substituents;

or, any $R^{c12}$ and $R^{d12}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{12A}$ substituents;

each $R^{b12}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b12}$ are each optionally substituted with 1, 2, 3, or 4 independently selected $R^{12A}$ substituents;

each $R^{e12}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{12A}$ is independently selected from halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a121}$, $SR^{a121}$, $NHOR^{a121}$, $C(O)R^{b121}$, $C(O)NR^{c121}R^{d121}$, $C(O)NR^{c121}(OR^{a121})$, $C(O)OR^{a121}$, $OC(O)R^{b121}$, $OC(O)NR^{c121}R^{d121}$, $NR^{c121}R^{d121}$, $NR^{c121}NR^{c121}R^{d121}$, $NR^{c121}C(O)R^{b121}$, $NR^{c121}C(O)OR^{a121}$, $NR^{c121}C(O)NR^{c121}R^{d121}$, $C(=NR^{e121})R^{b121}$, $C(=NR^{e121})NR^{c121}R^{d121}$, $NR^{c121}C(=NR^{e121})NR^{c121}R^{d121}$, $NR^{c121}C(=NR^{e121})R^{b121}$, $NR^{c121}S(O)R^{b121}$, $NR^{c121}S(O)NR^{c121}R^{d121}$, $NR^{c121}S(O)_2R^{b121}$, $NR^{c121}S(O)(=NR^{e121})R^{b121}$, $NR^{c121}S(O)_2NR^{c121}R^{d121}$, $S(O)R^{b121}$, $S(O)NR^{c121}R^{d121}$, $S(O)_2R^{b121}$, $S(O)_2NR^{c121}R^{d121}$, $OS(O)(=NR^{e121})R^{b121}$, and $OS(O)_2R^{b121}$;

each $R^{a121}$, $R^{c121}$, and $R^{d121}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

or, any $R^{c121}$ and $R^{d121}$ attached to the same N atom, together with the N atom to which they are attached, form a 5-10 membered heteroaryl or a 4-10 membered heterocycloalkyl group;

each $R^{b121}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{e121}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-; and each $R^M$ is independently selected from H, OH, halo, oxo, CN, C(O)OH, $NH_2$, $NO_2$, $SF_5$, $C_{1-6}$ alkyl, $C_{1-6}$ alkoxy, $C_{1-6}$ haloalkoxy, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-.

In some embodiments, the compound of Formula I is a compound of Formula II:

II

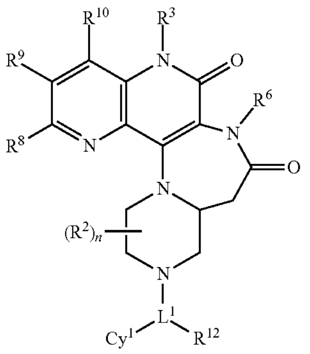

or a pharmaceutically acceptable salt thereof.

In some embodiments, the compound of Formula I is a compound of Formula III:

III

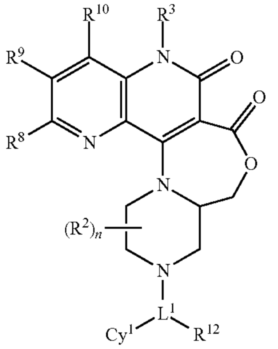

or a pharmaceutically acceptable salt thereof.

In some embodiments, the compound of Formula I is a compound of Formula IV:

IV

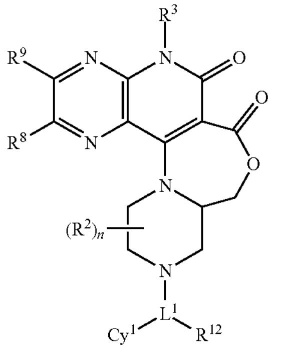

or a pharmaceutically acceptable salt thereof.

In some embodiments, the compound of Formula I is a compound of Formula V:

V

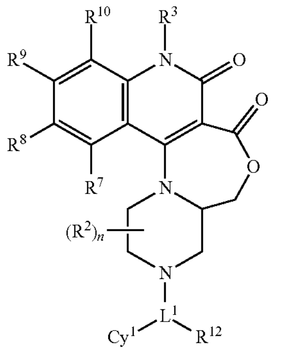

or a pharmaceutically acceptable salt thereof.

In some embodiments, the compound of Formula I is a compound of Formula VI:

VI

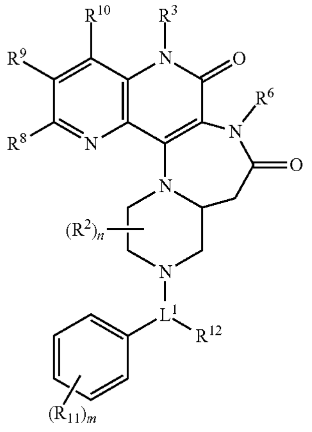

or a pharmaceutically acceptable salt thereof, wherein m is 0, 1, 2, 3, or 4.

In some embodiments, the compound of Formula I is a compound of Formula VII:

VII

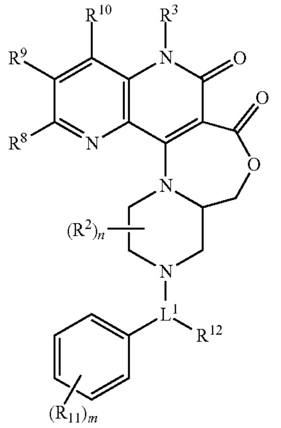

or a pharmaceutically acceptable salt thereof, wherein m is 0, 1, 2, 3, or 4.

In some embodiments, the compound of Formula I is a compound of Formula VIII:

VIII

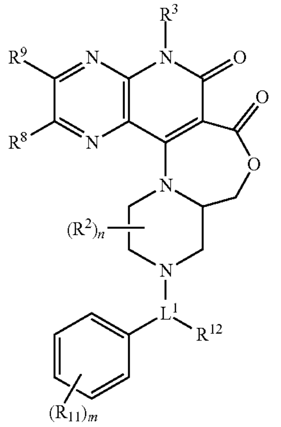

or a pharmaceutically acceptable salt thereof, wherein m is 0, 1, 2, 3, or 4.

In some embodiments, the compound of Formula I is a compound of Formula IX:

IX

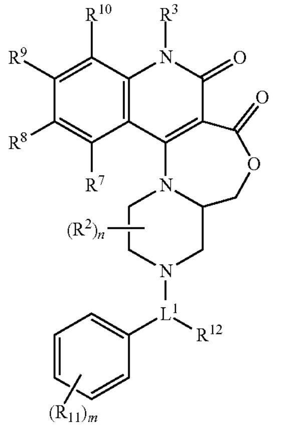

or a pharmaceutically acceptable salt thereof, wherein m is 0, 1, 2, 3, or 4.

In some embodiments, the compound provided herein is selected from:

11-(bis(4-fluorophenyl)methyl)-5,7-dimethyl-6,8-dioxo-5,6,7,8,9,9a,10,11,12,13-decahydropyrazino[1',2':4,5][1,4]diazepino[2,3-c][1,5]naphthyridine-2-carbonitrile;

(R)-11-(bis(4-fluorophenyl)methyl)-5-methyl-6,7-dioxo-5,7,9,9a,10,11,12,13-octahydro-6H-pyrazino[2',1':3,4][1,4]oxazepino[6,5-c][1,5]naphthyridine-2-carbonitrile;

(R)-2-(11-(bis(4-fluorophenyl)methyl)-5-methyl-6,7-dioxo-5,7,9,9a,10,11,12,13-octahydro-6H-pyrazino[2',1':3,4][1,4]oxazepino[6,5-c][1,5]naphthyridin-2-yl)acetonitrile;

(R)-2-(11-(bis(4-fluorophenyl)methyl)-5-methyl-6,7-dioxo-5,7,9,9a,10,11,12,13-octahydro-6H-pyrazino[2,1-c]pyrazino[2',3':5,6]pyrido[4,3-e][1,4]oxazepin-2-yl)acetonitrile;

(S)-11-(bis(4-fluorophenyl)methyl)-5-methyl-6,7-dioxo-5,7,9,9a,10,11,12,13-octahydro-6H-pyrazino[2',1':3,4][1,4]oxazepino[6,5-c][1,5]naphthyridine-2-carbonitrile;

(9aR,12R)-11-(bis(4-fluorophenyl)methyl)-5,12-dimethyl-6,7-dioxo-5,7,9,9a,10,11,12,13-octahydro-6H-pyrazino[2',1':3,4][1,4]oxazepino[6,5-c][1,5]naphthyridine-2-carbonitrile;

(R)-2-(3-(bis(4-fluorophenyl)methyl)-9-methyl-7,8-dioxo-1,2,3,4,4a,5,8,9-octahydro-7H-pyrazino[2',1':3,4][1,4]oxazepino[6,5-c]quinolin-12-yl)acetonitrile;

(R)-11-(bis(4-fluorophenyl)methyl)-5-methyl-6,7-dioxo-5,7,9,9a,10,11,12,13-octahydro-6H-pyrazino[2',1':3,4][1,4]oxazepino[6,5-c][1,5]naphthyridine-3-carbonitrile; and (R)-2-(11-(bis(4-fluorophenyl)methyl)-5-methyl-6,7-dioxo-5,7,9,9a,10,11,12,13-octahydro-6H-pyrazino[2',1':3,4][1,4]oxazepino[6,5-c][1,5]naphthyridin-3-yl)acetonitrile;

or a pharmaceutically acceptable salt thereof.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

At various places in the present specification, divalent linking substituents are described. It is specifically intended that each divalent linking substituent include both the forward and backward forms of the linking substituent. For example, $-NR(CR'R")_n$-includes both $-NR(CR'R")_n-$ and $-(CR'R")_nNR-$. Where the structure clearly requires a linking group, the Markush variables listed for that group are understood to be linking groups.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

As used herein, the phrase "optionally substituted" means unsubstituted or substituted. The substituents are independently selected, and substitution may be at any chemically accessible position. As used herein, the term "substituted" means that a hydrogen atom is removed and replaced by a substituent. A single divalent substituent, e.g., oxo, can replace two hydrogen atoms. It is to be understood that substitution at a given atom is limited by valency.

As used herein, the phrase "each 'variable' is independently selected from" means substantially the same as wherein "at each occurrence 'variable' is selected from."

Throughout the definitions, the terms "$C_{n-m}$" and "$C_{m-n}$" indicates a range which includes the endpoints, wherein n and m are integers and indicate the number of carbons. Examples include $C_{1-3}$, $C_{1-4}$, $C_{1-6}$, and the like.

As used herein, the term "$C_{n-m}$ alkyl", employed alone or in combination with other terms, refers to a saturated hydrocarbon group that may be straight-chain or branched, having n to m carbons. Examples of alkyl moieties include, but are not limited to, chemical groups such as methyl (Me), ethyl (Et), n-propyl (n-Pr), isopropyl (iPr), n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, from 2 to 6 carbon atoms, from 2 to 4 carbon atoms, from 2 to 3 carbon atoms, or 1 to 2 carbon atoms.

As used herein, "$C_{n-m}$ alkenyl" refers to an alkyl group having one or more double carbon-carbon bonds and having n to m carbons. Example alkenyl groups include, but are not limited to, ethenyl, n-propenyl, isopropenyl, n-butenyl, sec-butenyl, and the like. In some embodiments, the alkenyl moiety contains 2 to 6, 2 to 4, or 2 to 3 carbon atoms.

As used herein, "$C_{n-m}$ alkynyl" refers to an alkyl group having one or more triple carbon-carbon bonds and having n to m carbons. Example alkynyl groups include, but are not limited to, ethynyl, propyn-1-yl, propyn-2-yl, and the like. In some embodiments, the alkynyl moiety contains 2 to 6, 2 to 4, or 2 to 3 carbon atoms.

As used herein, the term "$C_{n-m}$ alkoxy", employed alone or in combination with other terms, refers to a group of formula —O-alkyl, wherein the alkyl group has n to m carbons. Example alkoxy groups include, but are not limited to, methoxy, ethoxy, propoxy (e.g., n-propoxy and isopropoxy), butoxy (e.g., n-butoxy and tert-butoxy), and the like. In some embodiments, the alkyl group has 1 to 6, 1 to 4, or 1 to 3 carbon atoms.

As used herein, the term "aryl," employed alone or in combination with other terms, refers to an aromatic hydrocarbon group, which may be monocyclic or polycyclic (e.g., having 2, 3 or 4 fused rings). The term "$C_{n-m}$ aryl" refers to an aryl group having from n to m ring carbon atoms. Aryl groups include, e.g., phenyl, naphthyl, anthracenyl, phenanthrenyl, and the like. In some embodiments, aryl groups have from 5 to 10 carbon atoms. In some embodiments, the aryl group is phenyl or naphthyl. In some embodiments, the aryl is phenyl.

As used herein, "halo" refers to F, Cl, Br, or I. In some embodiments, a halo is F, Cl, or Br. In some embodiments, a halo is F or Cl. In some embodiments, a halo is F. In some embodiments, a halo is Cl.

As used herein, "$C_{n-m}$ haloalkoxy" refers to a group of formula —O-haloalkyl having n to m carbon atoms. Example haloalkoxy groups include $OCF_3$ and $OCHF_2$. In some embodiments, the haloalkoxy group is fluorinated only. In some embodiments, the alkyl group has 1 to 6, 1 to 4, or 1 to 3 carbon atoms.

As used herein, the term "$C_{n-m}$ haloalkyl", employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the alkyl group has 1 to 6, 1 to 4, or 1 to 3 carbon atoms. Example haloalkyl groups include $CF_3$, $C_2F_5$, $CHF_2$, $CH_2F$, $CCl_3$, $CHCl_2$, $C_2Cl_5$ and the like.

As used herein, "cycloalkyl" refers to non-aromatic cyclic hydrocarbons including cyclized alkyl and alkenyl groups. Cycloalkyl groups can include mono- or polycyclic (e.g., having 2 fused rings) groups, spirocycles, and bridged rings (e.g., a bridged bicycloalkyl group). Ring-forming carbon atoms of a cycloalkyl group can be optionally substituted by oxo or sulfido (e.g., C(O) or C(S)). Also included in the definition of cycloalkyl are moieties that have one or more aromatic rings fused (i.e., having a bond in common with) to the cycloalkyl ring, for example, benzo or thienyl derivatives of cyclopentane, cyclohexane, and the like. A cycloalkyl group containing a fused aromatic ring can be attached through any ring-forming atom including a ring-forming atom of the fused aromatic ring. Cycloalkyl groups can have 3, 4, 5, 6, 7, 8, 9, or 10 ring-forming carbons (i.e., $C_{3-10}$). In some embodiments, the cycloalkyl is a $C_{3-10}$ monocyclic or bicyclic cycloalkyl. In some embodiments, the cycloalkyl is a $C_{3-7}$ monocyclic cycloalkyl. In some embodiments, the cycloalkyl is a $C_{4-7}$ monocyclic cycloalkyl. In some embodiments, the cycloalkyl is a $C_{4-10}$ spirocycle or bridged cycloalkyl (e.g., a bridged bicycloalkyl group). Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcaranyl, cubane, adamantane, bicyclo[1.1.1]pentyl, bicyclo[2.1.1]hexyl, bicyclo[2.2.1]heptanyl, bicyclo[3.1.1]heptanyl, bicyclo[2.2.2]octanyl, spiro[3.3]heptanyl, and the like. In some embodiments, cycloalkyl is cyclopropyl, cyclobutyl, cyclopentyl, or cyclohexyl.

As used herein, "heteroaryl" refers to a monocyclic or polycyclic (e.g., having 2 fused rings) aromatic heterocycle having at least one heteroatom ring member selected from N, O, S and B. In some embodiments, the heteroaryl ring has 1, 2, 3, or 4 heteroatom ring members independently selected from N, O, S and B. In some embodiments, any ring-forming N in a heteroaryl moiety can be an N-oxide. In some embodiments, the heteroaryl is a 5-10 membered monocyclic or bicyclic heteroaryl having 1, 2, 3, or 4 heteroatom ring members independently selected from N, O, S, and B. In some embodiments, the heteroaryl is a 5-, 7-, 8-, 9-, or, 10-membered monocyclic or bicyclic heteroaryl having 1, 2, 3, or 4 heteroatom ring members independently selected from N, O, S, and B. In some embodiments, the heteroaryl is a 5-10 membered monocyclic or bicyclic heteroaryl having 1, 2, 3, or 4 heteroatom ring members independently selected from N, O, and S. In some embodiments, the heteroaryl is a 5-, 7-, 8-, 9-, or 10-membered monocyclic or bicyclic heteroaryl having 1, 2, 3, or 4 heteroatom ring members independently selected from N, O, and S. In some embodiments, the heteroaryl is a 5-6 membered monocyclic heteroaryl having 1 or 2 heteroatom ring members independently selected from N, O, S, and B. In some embodiments, the heteroaryl is a 5 membered monocyclic heteroaryl having 1 or 2 heteroatom ring members independently selected from N, O, S, and B. In some embodiments, the heteroaryl is a 5 membered monocyclic heteroaryl having 1 or 2 heteroatom ring members independently selected from N, O, and S. In some embodiments, the heteroaryl group contains 5 to 10, 5 to 7, 3 to 7, or 5 to 6 ring-forming atoms. In some embodiments, the heteroaryl group has 1 to 4 ring-forming heteroatoms, 1 to 3 ring-forming heteroatoms, 1 to 2 ring-forming heteroatoms or 1 ring-forming heteroatom. When the heteroaryl group contains more than one heteroatom ring member, the heteroatoms may be the same or different. Example heteroaryl groups include, but are not limited to, thienyl (or thiophenyl), furyl (or furanyl), pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, 1,3,4-oxadiazolyl, 1,2-dihydro-1,2-azaborine, pyridinyl, pyrimidinyl, pyrazinyl, pyridazinyl, azolyl, triazolyl, thiadiazolyl, quinolinyl, isoquinolinyl, indolyl, benzothiophenyl, benzofuranyl, benzisoxazolyl, imidazo[1,2-b]thiazolyl, purinyl, triazinyl, thieno[3,2-b]pyridinyl, imidazo[1,2-a]pyridinyl, 1,5-naphthyridinyl, 1H-pyrazolo[4,3-b]pyridinyl, triazolo[4,3-a]pyridinyl, 1H-pyrrolo[3,2-b]pyridinyl, 1H-pyrrolo[2,3-b]pyridinyl, pyrazolo[1,5-a]pyridinyl, indazolyl, and the like.

As used herein, "heterocycloalkyl" refers to monocyclic or polycyclic heterocycles having at least one non-aromatic ring (saturated or partially unsaturated ring), wherein one or more of the ring-forming carbon atoms of the heterocycloalkyl is replaced by a heteroatom selected from N, O, S, and B, and wherein the ring-forming carbon atoms and heteroatoms of a heterocycloalkyl group can be optionally substituted by one or more oxo or sulfido (e.g., C(O), S(O), C(S), or $S(O)_2$, etc.). When a ring-forming carbon atom or heteroatom of a heterocycloalkyl group is optionally substituted by one or more oxo or sulfide, the O or S of said group is in addition to the number of ring-forming atoms specified herein (e.g., a 1-methyl-6-oxo-1,6-dihydropyridazin-3-yl is a 6-membered heterocycloalkyl group, wherein a ring-forming carbon atom is substituted with an oxo group, and wherein the 6-membered heterocycloalkyl group is further substituted with a methyl group). Heterocycloalkyl groups include monocyclic and polycyclic (e.g., having 2 fused rings) systems. Included in heterocycloalkyl are monocyclic and polycyclic 3 to 10, 4 to 10, 5 to 10, 4 to 7, 5 to 7, or 5 to 6 membered heterocycloalkyl groups. Heterocycloalkyl groups can also include spirocycles and bridged rings (e.g., a 5 to 10 membered bridged biheterocycloalkyl ring having one or more of the ring-forming carbon atoms replaced by a heteroatom independently selected from N, O, S, and B). The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds.

Also included in the definition of heterocycloalkyl are moieties that have one or more aromatic rings fused (i.e., having a bond in common with) to the non-aromatic heterocyclic ring, for example, benzo or thienyl derivatives of piperidine, morpholine, azepine, etc. A heterocycloalkyl group containing a fused aromatic ring can be attached through any ring-forming atom including a ring-forming atom of the fused aromatic ring.

In some embodiments, the heterocycloalkyl group contains 3 to 10 ring-forming atoms, 4 to 10 ring-forming atoms, 4 to 8 ring-forming atoms, 3 to 7 ring-forming atoms, or 5 to 6 ring-forming atoms. In some embodiments, the heterocycloalkyl group has 1 to 4 heteroatoms, 1 to 3 heteroatoms, 1 to 2 heteroatoms or 1 heteroatom. In some embodiments, the heterocycloalkyl is a monocyclic 4-6 membered heterocycloalkyl having 1 or 2 heteroatoms independently selected from N, O, S and B and having one or more oxidized ring members. In some embodiments, the heterocycloalkyl is a monocyclic or bicyclic 5-10, membered heterocycloalkyl having 1, 2, 3, or 4 heteroatoms independently selected from N, O, S, and B and having one or more oxidized ring members. In some embodiments, the heterocycloalkyl is a monocyclic or bicyclic 5 to 10 membered heterocycloalkyl having 1, 2, 3, or 4 heteroatoms independently selected from N, O, and S and having one or more oxidized ring members. In some embodiments, the heterocycloalkyl is a monocyclic 5 to 6 membered heterocycloalkyl having 1, 2, 3, or 4 heteroatoms independently selected from N, O, and S and having one or more oxidized ring members.

Example heterocycloalkyl groups include pyrrolidin-2-one (or 2-oxopyrrolidinyl), 1,3-isoxazolidin-2-one, pyranyl, tetrahydropyran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, 1,2,3,4-tetrahydroisoquinoline, tetrahydrothiopheneyl, tetrahydrothiopheneyl 1,1-dioxide, benzazapene, azabicyclo[3.1.0]hexanyl, diazabicyclo[3.1.0]hexanyl, oxobicyclo[2.1.1]hexanyl, azabicyclo[2.2.1]heptanyl, diazabicyclo[2.2.1]heptanyl, azabicyclo[3.1.1]heptanyl, diazabicyclo[3.1.1]heptanyl, azabicyclo[3.2.1]octanyl, diazabicyclo[3.2.1]octanyl, oxobicyclo[2.2.2]octanyl, azabicyclo[2.2.2]octanyl, azaadamantanyl, diazaadamantanyl, oxo-adamantanyl, azaspiro[3.3]heptanyl, 2-azaspiro[3.3]heptanyl, diazaspiro[3.3]heptanyl, azaspiro[3.5]nonanyl, 7-azaspiro[3.5]nonanyl, oxo-azaspiro[3.3]heptanyl, azaspiro[3.4]octanyl, diazaspiro[3.4]octanyl, oxo-azaspiro[3.4]octanyl, azaspiro[2.5]octanyl, diazaspiro[2.5]octanyl, azaspiro[4.4]nonanyl, diazaspiro[4.4]nonanyl, oxo-azaspiro[4.4]nonanyl, azaspiro[4.5]decanyl, diazaspiro[4.5]decanyl, diazaspiro[4.4]nonanyl, oxo-diazaspiro[4.4]nonanyl, oxo-dihydropyridazinyl, oxo-2,6-diazaspiro[3.4]octanyl, oxo-pyrrolidinyl, oxo-pyridinyl, and the like.

As used herein, "$C_{o-p}$ cycloalkyl-$C_{n-m}$ alkyl-" refers to a group of formula cycloalkyl-alkylene-, wherein the cycloalkyl has o to p carbon atoms and the alkylene linking group has n to m carbon atoms.

As used herein "$C_{o-p}$ aryl-$C_{n-m}$ alkyl-" refers to a group of formula aryl-alkylene-, wherein the aryl has o to p carbon atoms and the alkylene linking group has n to m carbon atoms.

As used herein, "heteroaryl-$C_{n-m}$ alkyl-" refers to a group of formula heteroaryl-alkylene-, wherein alkylene linking group has n to m carbon atoms.

As used herein "heterocycloalkyl-$C_{n-m}$ alkyl-" refers to a group of formula heterocycloalkyl-alkylene-, wherein alkylene linking group has n to m carbon atoms.

As used herein, an "alkyl linking group" or "alkylene linking group" is a bivalent straight chain or branched alkyl linking group ("alkylene group"). For example, "$C_{o-p}$ cycloalkyl-$C_{n-m}$ alkyl-", "$C_{o-p}$ aryl-$C_{n-m}$ alkyl-", "phenyl-$C_{n-m}$ alkyl-", "heteroaryl-$C_{n-m}$ alkyl-", and "heterocycloalkyl-$C_{n-m}$ alkyl-" contain alkyl linking groups. Examples of "alkyl linking groups" or "alkylene groups" include methylene, ethan-1,1-diyl, ethan-1,2-diyl, propan-1,3-dilyl, propan-1,2-diyl, propan-1,1-diyl and the like.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas a pyridin-3-yl ring is attached at the 3-position.

As used herein, the term "oxo" refers to an oxygen atom (i.e., =O) as a divalent substituent, forming a carbonyl group when attached to a carbon (e.g., C=O or C(O)), or attached to a nitrogen or sulfur heteroatom forming a nitroso, sulfinyl, or sulfonyl group.

As used herein, the term "independently selected from" means that each occurrence of a variable or substituent (e.g., each $R^M$), are independently selected at each occurrence from the applicable list.

The compounds described herein can be asymmetric (e.g., having one or more stereocenters). All stereoisomers, such as enantiomers and diastereomers, are intended unless otherwise indicated. Compounds of the present disclosure that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C═N double bonds, and the like can also be present in the compounds described herein, and all such stable isomers are contemplated in the present invention. Cis and trans geometric isomers of the compounds of the present disclosure are described and may be isolated as a mixture of isomers or as separated isomeric forms. In some embodiments, the compound has the (R)-configuration. In some embodiments, the compound has the (S)-configuration. The Formulas (e.g., Formula I, Formula II, etc.) provided herein include stereoisomers of the compounds.

Resolution of racemic mixtures of compounds can be carried out by any of numerous methods known in the art. An example method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzyl amine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds provided herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, 2-hydroxypyridine and 2-pyridone, and 1H- and 2H-pyrazole. Tautomeric forms can be in equilibrium or sterically locked into one form by appropriate substitution.

All compounds, and pharmaceutically acceptable salts thereof, can be found together with other substances such as water and solvents (e.g. hydrates and solvates) or can be isolated.

In some embodiments, preparation of compounds can involve the addition of acids or bases to affect, for example, catalysis of a desired reaction or formation of salt forms such as acid addition salts.

In some embodiments, the compounds provided herein, or salts thereof, are substantially isolated. By "substantially isolated" is meant that the compound is at least partially or substantially separated from the environment in which it was formed or detected. Partial separation can include, for example, a composition enriched in the compounds provided herein. Substantial separation can include compositions containing at least about 50%, at least about 60%, at least about 70%, at least about 80%, at least about 90%, at least about 95%, at least about 97%, or at least about 99% by weight of the compounds provided herein, or salt thereof.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present application also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN) are preferred. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

Synthesis

As will be appreciated by those skilled in the art, the compounds provided herein, including salts and stereoisomers thereof, can be prepared using known organic synthesis techniques and can be synthesized according to any of numerous possible synthetic routes. The schemes below provide general guidance in connection with preparing the compounds of the invention. One skilled in the art would understand that the preparations shown in the Schemes can be modified or optimized using general knowledge of organic chemistry to prepare various compounds of the invention.

Compounds of Formula 1-7 can be synthesized, for example, using the process shown in Scheme 1. As depicted in Scheme 1, acylation of compounds of Formula 1-1 (e.g., wherein R is an alkyl group, such as methyl or ethyl) under appropriate conditions (i.e., using acetic anhydride or acetyl chloride in a suitable solvent, such as THF) generates compounds of Formula 1-2. Compounds of Formula 1-1 are commercially available, or can be readily synthesized according to methods known by persons skilled in the art. Reaction of compounds of Formula 1-2 with appropriate electrophiles 1-3 (e.g., methyl iodide) under appropriate conditions (e.g., in the presence of a base, such as $Cs_2CO_3$, in an appropriate solvent, such as N,N-dimethylformamide) affords compounds of Formula 1-4. Cyclization of compounds of Formula 1-4 under appropriate conditions (e.g., using a suitable base, such as potassium bis(trimethylsilyl) amide, in a suitable solvent, such as tetrahydrofuran) provides compounds of Formula 1-5. Nitration of compounds of Formula 1-5 under suitable conditions (e.g., using $HNO_3$ in a suitable solvent, such as acetic acid) generates compounds of Formula 1-6. Conversion of the hydroxyl group in compounds of Formula 1-6 into an appropriate leaving group (i.e., wherein LG is triflate or a suitable halogen) provides compounds of Formula 1-7. For example, compounds of Formula 1-6 can be reacted with triflic anhydride in an appropriate solvent, such as $CH_2Cl_2$, to prepare compounds of Formula 1-7 where LG is triflate (i.e., $—OSO_2CF_3$). Alternatively, compounds of Formula 1-6 can be reacted with an appropriate phosphoryl halide (e.g., such as $POCl_3$) under appropriate conditions (e.g., neat or in an appropriate solvent, such as toluene) to generate compounds of Formula 1-7 where LG is a suitable halogen.

Scheme 1.

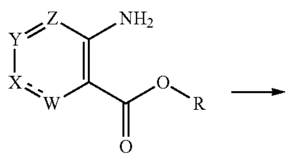

1-1

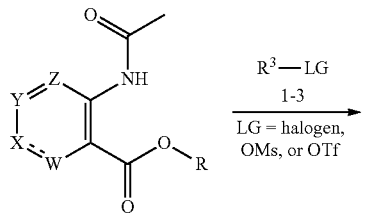

1-2

-continued

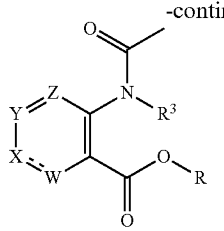

1-4

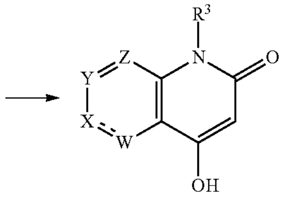

1-5

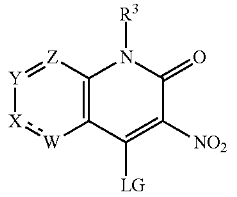

1-7

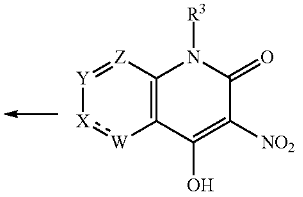

1-6

Compounds of Formula 2-8 can be prepared, for example, using the process illustrated in Scheme 2. In the process depicted in Scheme 2, nucleophilic aromatic substitution reactions between compounds of Formula 2-1 (e.g., wherein R' is an alkyl group, such as methyl or ethyl) and compounds of Formula 1-7 under appropriate conditions (e.g., in the presence of a base, such as N,N-diisopropylethylamine, in an appropriate solvent, such as $CH_3CN$ or 1-butanol) affords compounds of Formula 2-2. Alternatively, compounds of Formula 2-2 can be accessed via suitable transition metal catalyzed C—N bond forming reactions (e.g., including, but not limited to, Buchwald-Hartwig amination (*Chem. Sci.* 2011, 2, 27-50), Cu-catalyzed amination (*Org. React.* 2014, 85, 1-688), among others) between compounds of Formula 2-1 and compounds of Formula 1-7. Reduction of the nitro group in compounds of Formula 2-2 under appropriate conditions (e.g., iron in the presence of ammonium chloride, or hydrogen gas in the presence of a palladium catalyst, such as Pd/C) provides compounds of Formula 2-3. Intramolecular cyclization of compounds of Formula 2-3 under appropriate conditions (e.g., in the presence of a base, such as sodium hydride, in a suitable solvent, such as N,N-dimethylformamide) affords compounds of Formula 2-4. Reaction of compounds of Formula 2-4 with appropriate electrophiles of Formula 2-5 (e.g., methyl iodide) under appropriate conditions (e.g., in the presence of a base, such as sodium hydride, in a suitable solvent, such as N,N-dimethylformamide) affords compounds of Formula 2-6. Removal of an appropriate protecting group (e.g., wherein PG is a group such as tert-butoxycarbonyl) from compounds of Formula 2-6 under appropriate conditions (e.g., in the presence of an acid, such as HCl or trifluoroacetic acid, in a suitable solvent, such as tetrahydrofuran, 1-4-dioxane, or $CH_2Cl_2$), followed by nucleophilic substitution reactions with compounds of Formula 2-7 under appropriate conditions (e.g., in the presence of a base, such as N,N-diisopropylethylamine, in an appropriate solvent, such as $CH_3CN$) generates compounds of Formula 2-8.

Scheme 2.

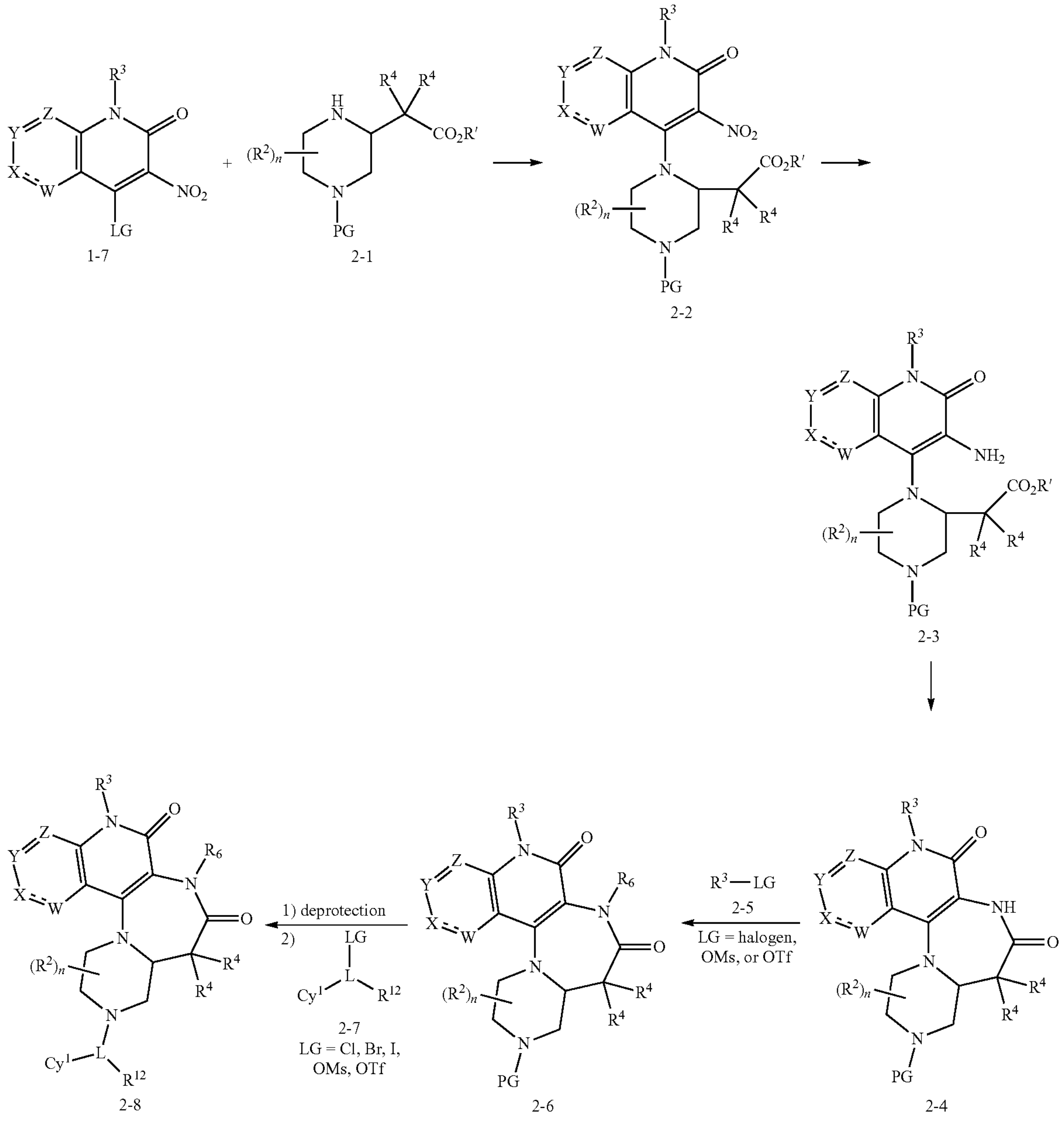

Compounds of Formula 3-6 can be synthesized, for example, using the process shown in Scheme 3. As depicted in Scheme 3, acylation of compounds of Formula 3-1 (e.g., wherein R is an alkyl group, such as methyl or ethyl) under appropriate conditions (i.e., using an acid chloride, such as methyl 3-chloro-3-oxopropanoate, in the presence of a base, such as pyridine, in a suitable solvent, such as $CH_2Cl_2$ or 1,2-dichloroethane) provides compounds of Formula 3-2. Compounds of Formula 3-1 are commercially available, or can be readily synthesized according to methods known by persons skilled in the art. Cyclization of compounds of Formula 3-2 under appropriate conditions (e.g., using a suitable base, such as sodium methoxide) provides compounds of Formula 3-3. Reaction of compounds of Formula 3-3 with appropriate electrophiles of Formula 3-4 (e.g., methyl iodide) under appropriate conditions (e.g., in the presence of a base, such as lithium bis(trimethylsilyl)amide, in an appropriate solvent, such as N,N-dimethylformamide) affords compounds of Formula 3-5. Conversion of the hydroxyl group in compounds of Formula 3-5 into an appropriate leaving group (i.e., wherein LG is triflate or a suitable halogen) provides compounds of Formula 3-6. For example, compounds of Formula 3-5 can be reacted with triflic anhydride in an appropriate solvent, such as $CH_2Cl_2$, to prepare compounds of Formula 3-6 where LG is triflate (i.e., $—OSO_2CF_3$). Alternatively, compounds of Formula 3-5 can be reacted with an appropriate phosphoryl halide (e.g., such as $POCl_3$) under appropriate conditions (e.g., neat or in an appropriate solvent, such as toluene) to generate compounds of Formula 3-6 where LG is a suitable halogen.

Scheme 3.

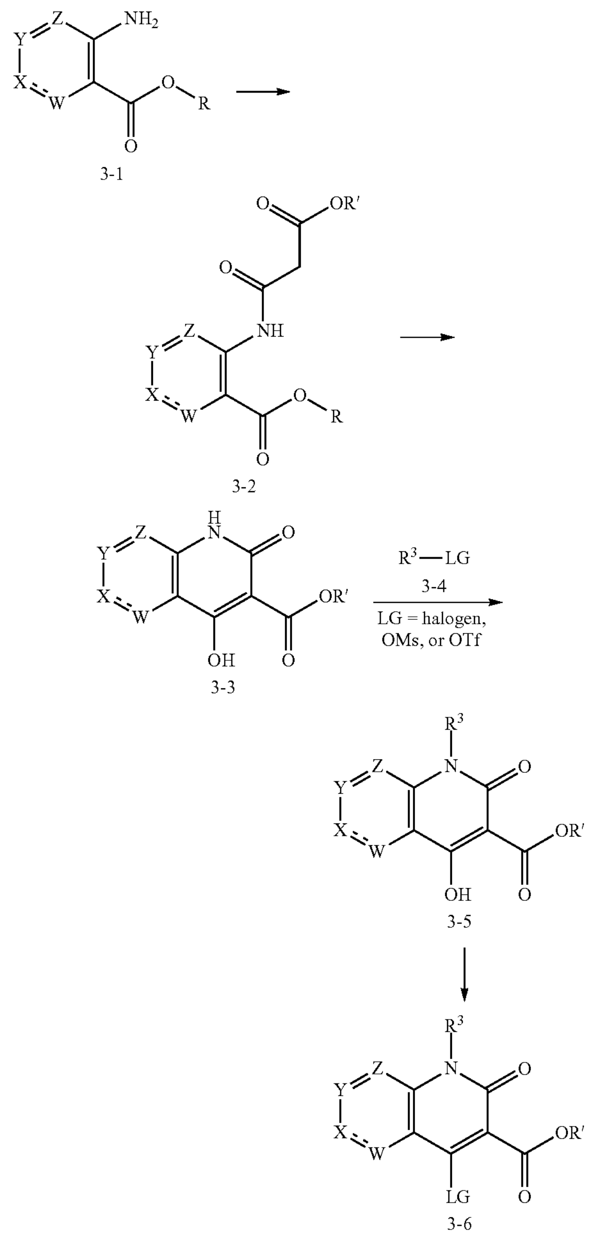

3-1, 3-2, 3-3, 3-5, 3-6

Compounds of Formula 4-4 can be prepared, for example, using the process illustrated in Scheme 4. In the process depicted in Scheme 4, nucleophilic substitution reactions between compounds of Formula 4-1 and compounds of Formula 4-2 under appropriate conditions (e.g., in the presence of a base, such as N,N-diisopropylethylamine, in an appropriate solvent, such as $CH_3CN$) generates compounds of Formula 4-3. Removal of an appropriate protecting group (e.g., wherein PG is a group such as tert-butoxycarbonyl) from compounds of Formula 4-3 under appropriate conditions (e.g., in the presence of an acid, such as HCl or trifluoroacetic acid, in a suitable solvent, such as tetrahydrofuran, 1-4-dioxane, or $CH_2Cl_2$) affords compounds of Formula 4-4.

Scheme 4.

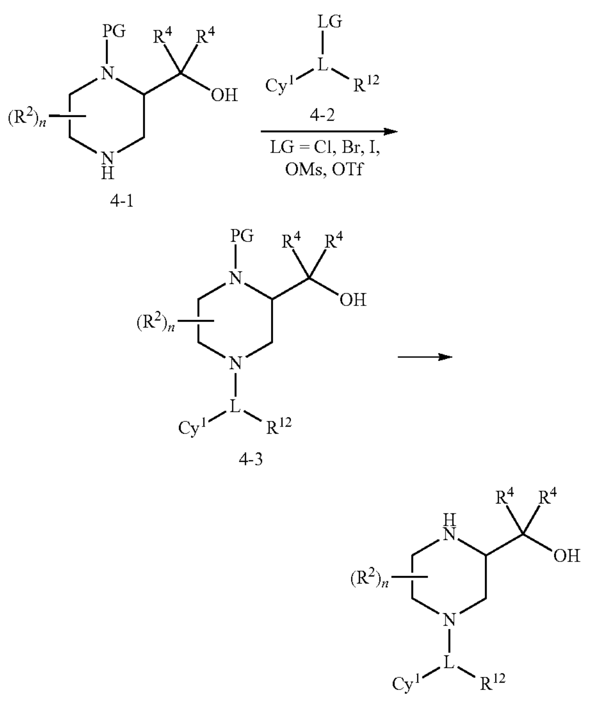

4-1, 4-3, 4-4

Compounds of Formula 5-2 can be prepared, for example, using the process illustrated in Scheme 5. In the process depicted in Scheme 5, nucleophilic aromatic substitution reactions between compounds of Formula 3-6 (e.g., wherein R' is an alkyl group, such as methyl or ethyl) and compounds of Formula 4-4 under appropriate conditions (e.g., in the presence of a base, such as N,N-diisopropylethylamine, in an appropriate solvent, such as $CH_3CN$ or 1-butanol) affords compounds of Formula 5-1. Alternatively, compounds of Formula 5-1 can be accessed via suitable transition metal catalyzed C—N bond forming reactions (e.g., including, but not limited to, Buchwald-Hartwig amination (*Chem. Sci.* 2011, 2, 27-50), Cu-catalyzed amination (*Org. React.* 2014, 85, 1-688), among others) between compounds of Formula 3-6 and compounds of Formula 4-4. Intramolecular cyclization of compounds of Formula 5-1 under appropriate conditions (e.g., in the presence of a Lewis acid, such as $AlMe_3$, in a suitable solvent, such as $CH_2Cl_2$; or in the presence of a BrIInsted acid, such as p-toluenesulfonic acid, in a suitable solvent, such as toluene) generates compounds of Formula 5-2.

Scheme 5.

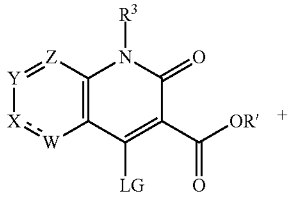

3-6

-continued

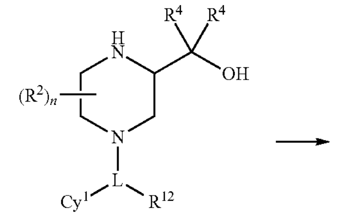

4-4

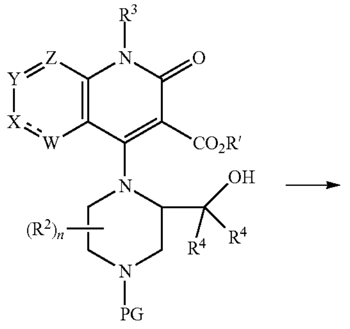

5-1

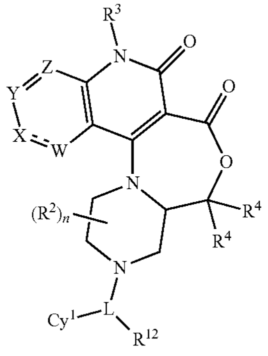

5-2

The reactions for preparing compounds described herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, (e.g., temperatures which can range from the solvent's freezing temperature to the solvent's boiling temperature). A given reaction can be carried out in one solvent or a mixture of more than one solvent. Depending on the particular reaction step, suitable solvents for a particular reaction step can be selected by the skilled artisan.

The expressions, "ambient temperature" or "room temperature" or "rt" as used herein, are understood in the art, and refer generally to a temperature, e.g., a reaction temperature, that is about the temperature of the room in which the reaction is carried out, for example, a temperature from about 20° C. to about 30° C.

Preparation of compounds described herein can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, Protective Groups in Organic Synthesis, 3$^{rd}$ Ed., Wiley & Sons, Inc., New York (1999).

Reactions can be monitored according to any suitable method known in the art. For example, product formation can be monitored by spectroscopic means, such as nuclear magnetic resonance spectroscopy (e.g., $^{1}$H or $^{13}$C), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) and normal phase silica chromatography.

Methods of Use

The compounds described herein can inhibit the activity of DGK. Compounds that inhibit DGK are useful in providing a means of preventing the growth or inducing apoptosis of cancer cells. Such compounds are also useful in treating cancer cells exhibiting alterations in diacylglycerol-regulating enzymes and effectors. It is therefore anticipated that the compounds of the disclosure are useful in treating or preventing cancer, such as solid tumors.

In certain embodiments, the disclosure provides a method for treating a DGK-related disorder in a patient in need thereof, comprising the step of administering to said patient a compound of the disclosure, or a pharmaceutically acceptable composition thereof.

The compounds or salts described herein can be selective. By "selective," it is meant that the compound binds to or inhibits DGKα or DGKζ with greater affinity or potency, respectively, compared to at least one other DGK isoforms, or kinase, etc. In some embodiments, selectivity can be at least about 2-fold, 5-fold, 10-fold, at least about 20-fold, at least about 50-fold, at least about 100-fold, at least about 200-fold, at least about 500-fold or at least about 1000-fold. The compounds of the present disclosure can also be dual antagonists (i.e., inhibitors), e.g. inhibit both DGKα and DGKζ kinases. In some embodiments, the compounds of the invention are selective inhibitors of DGKα (e.g., over one or more other DGK isoforms, or kinase, etc.). In some embodiments, the compounds of the invention are selective inhibitors of DGKζ (e.g., over one or more other DGK isoforms, or kinase, etc.). Selectivity can be measured by methods routine in the art. In some embodiments, selectivity can be tested at the $K_m$ ATP concentration of each enzyme. In some embodiments, the selectivity of compounds of the invention can be determined by cellular assays associated with particular DGK kinase activity.

Based on compelling evidence that DGKα and DGKζ negatively regulate signaling pathways downstream of the T cell receptor, developing DGK inhibitors can boost T cell effector function and inhibit tumor progression. DGK inhibitors can be used to treat, alone or in combination with other therapies, renal cell carcinoma, mesothelioma, glioblastoma multiforme, colorectal cancer, melanoma, pancreatic cancer (Chen, S. S. et al., *Front. Cell Dev. Biol.*, 2016. 4:130; Gu, J. et al., *Oncoimmunol.*, 2021. 10, e1941566; Jung I.-Y. et al., *Cancer Res.*, 2018. 78:p 4692-4703; Sitaram, P., et al., *Int. J Mol. Sci.*, 2019. 20:p 5821-5848; Wesley, E. M., et al., *Immunohorizons*, 2018. 2:p 107-118)

In addition, DGKα has been shown to enhance esophageal squamous cell carcinoma (ESCC), and human hepatocellular carcinoma (HCC) progression (Chen, J. et al., *Oncogene*, 2019. 38:p 2533-2550; Takeishi, K. et al., *J. Hepatol.*, 2012. 57:p 77-83), to support colon and breast cancer growth in three-dimensional (3D) culture (Torres-Ayuso, P. et al., *Oncotarget*, 2014. 5:p 9710-9726), to enhance mammary carcinoma invasiveness (Rainero, E. et al., *PLOS ONE*, 2014. 9(6): e97144) and promote metastasis of non-small cell lung cancer (NSCLC) (Fu, L. et al., *Cancer*

*letters,* 2022. 532: 215585) whereas DGKζ has been implicated as a potential oncogene in osteosarcoma proliferation (Yu, W. et al., *Front. Oncol.,* 2019. 8:655) and contributed to enhanced invasion of human metastatic colon cancer cells (Cai, K. et al., *BMC Cancer,* 2014. 14:208). It has also been reported DGK inhibition has the potential to reduce immunopathology in X-linked lymphoproliferative disease patient (Velnati, S. et al., *Eur. J Med. Chem.,* 2019. 164: p 378-390; Ruffo, E. et al., *Sci. Transl. Med.* 2016. 8 (321):321ra7).

In some embodiments, the DGK-related disorder is a solid tumor. Example solid tumors include, but are not limited to, breast cancer, colorectal cancer, gastric cancer, and glioblastoma (see e.g., Cooke & Kazanietz, *Sci. Signal,* 2022, 15, eabo0264:1-26). Example cancers associated with alterations in DAG-regulating enzymes and effector include, but are not limited to, uveal melanoma, myelodysplastic syndrome (MDS), angiosarcoma, nodal peripheral T cell lymphoma, adult T-cell leukemia lymphoma (ATLL), cutaneous T-cell lymphoma (CTCL)/Sezary syndrome, chronic lymphocytic leukemia (CLL), breast cancer, gastric cancer, colorectal cancer, oral squamous cell carcinoma (SCC), esophageal SCC, chronic myeloid leukemia (CML), colon cancer, prostate cancer, hepatocellular carcinoma (HCC), blue nevi, NK/T cell lymphoma, glioma, ovarian cancer, liver cancer, melanoma, heptacarcinoma, ostersarcoma, chordiod glioma, pigmented epithelioid melanocytoma, papillary glioneuronal tumor, fibrous histiocytoma, pituitary tumor, thyroid cancer, head and neck SCC, lung cancer, pediatric T-cell acute lymphoblastic leukemia (T-ALL), endometrial cancer, angiolipoma, salivary gland cancer, acute myeloid leukemia (AML), Epstein-Barr virus-associated (EBV)-associated B cell lymphoma, diffuse large B cell lymphoma (DLBCL), and cervical cancer (see e.g., Cooke & Kazanietz, *Sci. Signal,* 2022, 15, eabo0264:1-26).

In some embodiments, the cancer is selected from lung cancer, bladder cancer, urothelial cancer, esophageal cancer, stomach cancer, mesothelioma, liver cancer, diffuse large B cell lymphoma, kidney cancer, head and neck cancer, cholangiocarcinoma, cervical cancer, endocervical cancer, and melanoma.

In some embodiments, the cancer is selected from non-small cell lung cancer (lung squamous cell carcinoma (LUSC), lung adenocarcinoma (LUAD)), bladder urothelial carcinoma, esophageal carcinoma, stomach adenocarcinoma, mesothelioma, liver hepatocellular carcinoma, diffuse large B cell lymphoma (DLBCL), kidney renal clear cell carcinoma, head and neck squamous cell carcinoma, cholangiocarcinoma, cervical squamous cell carcinoma, endocervical adenocarcinoma, and metastatic melanoma.

In some embodiments, the cancer is a myelodysplastic syndrome. As used herein, myelodysplastic syndromes are intended to encompass heterogeneous and clonal hematopoietic disorders that are characterized by ineffective hematopoiesis on one or more of the major myeloid cell lineages. Myelodysplastic syndromes are associated with bone marrow failure, peripheral blood cytopenias, and a propensity to progress to acute myeloid leukemia (AML). Moreover, clonal cytogenetic abnormalities can be detected in about 50% of cases with MDS. In 1997, The World Health Organization (WHO) in conjunction with the Society for Hematopathology (SH) and the European Association of Hematopathology (EAHP) proposed new classifications for hematopoietic neoplasms (Harris, et al., *J Clin Oncol* 1999; 17:3835-3849; Vardiman, et al., *Blood* 2002; 100:2292-2302). For MDS, the WHO utilized not only the morphologic criteria from the French-American-British (FAB) classification but also incorporated available genetic, biologic, and clinical characteristics to define subsets of MDS (Bennett, et al., *Br. J. Haematol.* 1982; 51:189-199). In 2008, the WHO classification of MDS (Table 1) was further refined to allow precise and prognostically relevant subclassification of unilineage dysplasia by incorporating new clinical and scientific information (Vardiman, et al., *Blood* 2009; 114: 937-951; Swerdlow, et al., *WHO Classification of Tumours of Haematopoietic and Lymphoid Tissues.* 4th Edition. Lyon France: IARC Press; 2008:88-103; Bunning and Germing, "Myelodysplastic syndromes/neoplasms" in Chapter 5, Swerdlow, et al, eds. *WHO Classification of Tumours of Haematopoietic and Lymphoid Tissues.* (ed. 4th edition): Lyon, France: IARC Press; 2008:88-103).

TABLE 1

2008 WHO Classification for De Novo Myelodysplastic Syndrome

| Subtype | Blood | Bone Marrow |
|---|---|---|
| Refractory cytopenia with unilineage dysplasia (RCUD) | Single or Bicytopenia | Dysplasia in ≥10% of 1 cell line, <5% blasts |
| Refractory anemia with ring sideroblasts (RARS) | Anemia, no blasts | ≥15% of erythroid precursors w/ring sideroblasts, erythroid dysplasia only, <5% blasts |
| Refractory cytopenia with multilineage dysplasia | Cytopenia(s), <1 × $10^9$/L monocytes | Dysplasia in ≥10% of cells in ≥2 hematopoietic lineages, ±15% ring sideroblasts, <5% blasts |
| Refractory anemia with excess blasts-1 (RAEB-1) | Cytopenia(s), ≤2% to 4% blasts, <1 × $10^9$/L monocytes | Unilineage or multilineage dysplasia, No Auer rods, 5% to 9% blasts |
| Refractory anemia with excess blasts-2 (RAEB-2) | Cytopenia(s), ≤5% to 19% blasts, <1 × $10^9$/L monocytes | Unilineage or multilineage dysplasia, ±Auer rods, 10% to 19% blasts |
| Myelodysplastic syndrome, unclassified (MDS-U) | Cytopenias | Unilineage or no dysplasia but characteristic MDS cytogenetics, <5% blasts |
| MDS associated with isolated del(5q) | Anemia, platelets normal or increased | Unilineage erythroid. Isolated del(5q), <5% blasts |

In some embodiments, the myelodysplastic syndrome is refractory cytopenia with unilineage dysplasia (RCUD).

In some embodiments, the myelodysplastic syndrome is refractory anemia with ring sideroblasts (RARS).

In some embodiments, the myelodysplastic syndrome is refractory anemia with ring sideroblasts associated with thrombocytosis (RARS-T).

In some embodiments, the myelodysplastic syndrome is refractory cytopenia with multilineage dysplasia.

In some embodiments, the myelodysplastic syndrome is refractory anemia with excess blasts-1 (RAEB-1).

In some embodiments, the myelodysplastic syndrome is refractory anemia with excess blasts-2 (RAEB-2).

In some embodiments, the myelodysplastic syndrome is myelodysplastic syndrome, unclassified (MDS-U).

In some embodiments, the myelodysplastic syndrome is myelodysplastic syndrome associated with isolated del(5q).

In some embodiments, the myelodysplastic syndrome is refractory to erythropoiesis-stimulating agents.

In some embodiments, the compounds of the disclosure can be useful in the treatment of myeloproliferative disorder/myelodysplastic overlap syndrome (MPD/MDS overlap syndrome).

In some embodiments, provided herein is a method of increasing survival or progression-free survival in a patient, comprising administering a compound provided herein to the patient. In some embodiments, the patient has cancer. In some embodiments, the patient has a disease or disorder described herein. As used herein, progression-free survival refers to the length of time during and after the treatment of a solid tumor that a patient lives with the disease but it does not get worse. Progression-free survival can refer to the length of time from first administering the compound until the earlier of death or progression of the disease. Progression of the disease can be defined by RECIST v. 1.1 (Response Evaluation Criteria in Solid Tumors), as assessed by an independent centralized radiological review committee. In some embodiments, administering of the compound results in a progression free survival that is greater than about 1 month, about 2 months, about 3 months, about 4 months, about 5 months, about 6 months, about 8 months, about 9 months, about 12 months, about 16 months, or about 24 months. In some embodiments, the administering of the compound results in a progression free survival that is at least about 1 month, about 2 months, about 3 months, about 4 months, about 5 months, about 6 months, about 8 months, about 9 months, or about 12 months; and less than about 24 months, about 16 months, about 12 months, about 9 months, about 8 months, about 6 months, about 5 months, about 4 months, about 3 months, or about 2 months. In some embodiments, the administering of the compound results in an increase of progression free survival that is at least about 1 month, about 2 months, about 3 months, about 4 months, about 5 months, about 6 months, about 8 months, about 9 months, or about 12 months; and less than about 24 months, about 16 months, about 12 months, about 9 months, about 8 months, about 6 months, about 5 months, about 4 months, about 3 months, or about 2 months.

The present disclosure further provides a compound described herein, or a pharmaceutically acceptable salt thereof, for use in any of the methods described herein.

The present disclosure further provides use of a compound described herein, or a pharmaceutically acceptable salt thereof, for the preparation of a medicament for use in any of the methods described herein.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" a DGK with a compound described herein includes the administration of a compound described herein to an individual or patient, such as a human, having a DGK, as well as, for example, introducing a compound described herein into a sample containing a cellular or purified preparation containing the DGK.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent such as an amount of any of the solid forms or salts thereof as disclosed herein that elicits the biological or medicinal response in a tissue, system, animal, individual or human that is being sought by a researcher, veterinarian, medical doctor or other clinician. An appropriate "effective" amount in any individual case may be determined using techniques known to a person skilled in the art.

The phrase "pharmaceutically acceptable" is used herein to refer to those compounds, materials, compositions, and/or dosage forms which are, within the scope of sound medical judgment, suitable for use in contact with the tissues of human beings and animals without excessive toxicity, irritation, allergic response, immunogenicity or other problem or complication, commensurate with a reasonable benefit/risk ratio.

As used herein, the phrase "pharmaceutically acceptable carrier or excipient" refers to a pharmaceutically-acceptable material, composition, or vehicle, such as a liquid or solid filler, diluent, solvent, or encapsulating material. Excipients or carriers are generally safe, non-toxic and neither biologically nor otherwise undesirable and include excipients or carriers that are acceptable for veterinary use as well as human pharmaceutical use. In one embodiment, each component is "pharmaceutically acceptable" as defined herein. See, e.g., *Remington: The Science and Practice of Pharmacy,* 21st ed.; Lippincott Williams & Wilkins: Philadelphia, Pa., 2005; *Handbook of Pharmaceutical Excipients,* 6th ed.; Rowe et al., Eds.; The Pharmaceutical Press and the American Pharmaceutical Association: 2009; *Handbook of Pharmaceutical Additives,* 3rd ed.; Ash and Ash Eds.; Gower Publishing Company: 2007; *Pharmaceutical Preformulation and Formulation,* 2nd ed.; Gibson Ed.; CRC Press LLC: Boca Raton, Fla., 2009.

As used herein, the term "treating" or "treatment" refers to inhibiting the disease; for example, inhibiting a disease, condition or disorder in an individual who is experiencing or displaying the pathology or symptomatology of the disease, condition or disorder (i.e., arresting further development of the pathology and/or symptomatology) or ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

In some embodiments, the compounds of the invention are useful in preventing or reducing the risk of developing any of the diseases referred to herein; e.g., preventing or reducing the risk of developing a disease, condition or disorder in an individual who may be predisposed to the disease, condition or disorder but does not yet experience or display the pathology or symptomatology of the disease.

It is appreciated that certain features of the disclosure, which are, for clarity, described in the context of separate embodiments, can also be provided in combination in a single embodiment (while the embodiments are intended to be combined as if written in multiply dependent form). Conversely, various features of the disclosure which are, for brevity, described in the context of a single embodiment, can also be provided separately or in any suitable subcombination.

Combination Therapies

I. Immune-Checkpoint Therapies

In some embodiments, DGKα and DGKζ inhibitors provided herein can be used in combination with one or more immune checkpoint inhibitors for the treatment of cancer as described herein.

Compounds of the present disclosure can be used in combination with one or more immune checkpoint inhibitors for the treatment of diseases, such as cancer or infections. Exemplary immune checkpoint inhibitors include inhibitors against immune checkpoint molecules such as CBL-B, CD20, CD28, CD40, CD70, CD122, CD96, CD73, CD47, CDK2, GITR, CSF1R, JAK, PI3K delta, PI3K gamma, TAM, arginase, HPK1, CD137 (also known as 4-1BB), ICOS, A2AR, B7-H3, B7-H4, BTLA, CTLA-4, LAG3, TIM3, TLR (TLR7/8), TIGIT, CD112R, VISTA, PD-1, PD-L1 and PD-L2. In some embodiments, the immune checkpoint molecule is a stimulatory checkpoint molecule selected from CD27, CD28, CD40, ICOS, OX40, GITR and CD137. In some embodiments, the immune checkpoint molecule is an inhibitory checkpoint molecule selected from A2AR, B7-H3, B7-H4, BTLA, CTLA-4, IDO, KIR, LAG3, PD-1, TIM3, TIGIT, and VISTA. In some embodiments, the compounds provided herein can be used in combination with one or more agents selected from KIR inhibitors, TIGIT inhibitors, LAIR1 inhibitors, CD160 inhibitors, 2B4 inhibitors and TGFR beta inhibitors.

In some embodiments, the compounds provided herein can be used in combination with one or more agonists of immune checkpoint molecules, e.g., OX40, CD27, GITR, and CD137 (also known as 4-1 BB).

In some embodiments, the inhibitor of an immune checkpoint molecule is anti-PD1 antibody, anti-PD-L1 antibody, or anti-CTLA-4 antibody.

In some embodiments, the inhibitor of an immune checkpoint molecule is an inhibitor of PD-1 or PD-L1, e.g., an anti-PD-1 or anti-PD-L1 monoclonal antibody. In some embodiments, the anti-PD-1 or anti-PD-L1 antibody is nivolumab, pembrolizumab, atezolizumab, durvalumab, avelumab, cemiplimab, atezolizumab, avelumab, tislelizumab, spartalizumab (PDR001), cetrelimab (JNJ-63723283), toripalimab (JS001), camrelizumab (SHR-1210), sintilimab (IBI308), AB122 (GLS-010), AMP-224, AMP-514/MEDI-0680, BMS936559, JTX-4014, BGB-108, SHR-1210, MEDI4736, FAZ053, BCD-100, KN035, CS1001, BAT1306, LZM009, AK105, HLX10, SHR-1316, CBT-502 (TQB2450), A167 (KL-A167), STI-A101 (ZKAB001), CK-301, BGB-A333, MSB-2311, HLX20, TSR-042, or LY3300054. In some embodiments, the inhibitor of PD-1 or PD-L1 is one disclosed in U.S. Pat. Nos. 7,488,802, 7,943,743, 8,008,449, 8,168,757, 8,217, 149, or 10,308,644; U.S. Publ. Nos. 2017/0145025, 2017/0174671, 2017/0174679, 2017/0320875, 2017/0342060, 2017/0362253, 2018/0016260, 2018/0057486, 2018/0177784, 2018/0177870, 2018/0179179, 2018/0179201, 2018/0179202, 2018/0273519, 2019/0040082, 2019/0062345, 2019/0071439, 2019/0127467, 2019/0144439, 2019/0202824, 2019/0225601, 2019/0300524, or 2019/0345170; or PCT Pub. Nos. WO 03042402, WO 2008156712, WO 2010089411, WO 2010036959, WO 2011066342, WO 2011159877, WO 2011082400, or WO 2011161699, which are each incorporated herein by reference in their entirety. In some embodiments, the inhibitor of PD-L1 is INCB086550.

In some embodiments, the antibody is an anti-PD-1 antibody, e.g., an anti-PD-1 monoclonal antibody. In some embodiments, the anti-PD-1 antibody is nivolumab, pembrolizumab, cemiplimab, spartalizumab, camrelizumab, cetrelimab, toripalimab, sintilimab, AB122, AMP-224, JTX-4014, BGB-108, BCD-100, BAT1306, LZM009, AK105, HLX10, or TSR-042. In some embodiments, the anti-PD-1 antibody is nivolumab, pembrolizumab, cemiplimab, spartalizumab, camrelizumab, cetrelimab, toripalimab, or sintilimab. In some embodiments, the anti-PD-1 antibody is pembrolizumab. In some embodiments, the anti-PD-1 antibody is nivolumab. In some embodiments, the anti-PD-1 antibody is cemiplimab. In some embodiments, the anti-PD-1 antibody is spartalizumab. In some embodiments, the anti-PD-1 antibody is camrelizumab. In some embodiments, the anti-PD-1 antibody is cetrelimab. In some embodiments, the anti-PD-1 antibody is toripalimab. In some embodiments, the anti-PD-1 antibody is sintilimab. In some embodiments, the anti-PD-1 antibody is AB122. In some embodiments, the anti-PD-1 antibody is AMP-224. In some embodiments, the anti-PD-1 antibody is JTX-4014. In some embodiments, the anti-PD-1 antibody is BGB-108. In some embodiments, the anti-PD-1 antibody is BCD-100. In some embodiments, the anti-PD-1 antibody is BAT1306. In some embodiments, the anti-PD-1 antibody is LZM009. In some embodiments, the anti-PD-1 antibody is AK105. In some embodiments, the anti-PD-1 antibody is HLX10. In some embodiments, the anti-PD-1 antibody is TSR-042. In some embodiments, the anti-PD-1 monoclonal antibody is nivolumab or pembrolizumab. In some embodiments, the anti-PD-1 monoclonal antibody is MGA012 (INCMGA0012; retifanlimab). In some embodiments, the anti-PD1 antibody is SHR-1210. Other anti-cancer agent(s) include antibody therapeutics such as 4-1BB (e.g., urelumab, utomilumab). In some embodiments, the inhibitor of an immune checkpoint molecule is an inhibitor of PD-L1, e.g., an anti-PD-L1 monoclonal antibody. In some embodiments, the anti-PD-L1 monoclonal antibody is atezolizumab, avelumab, durvalumab, tislelizumab, BMS-935559, MEDI4736, atezolizumab (MPDL3280A; also known as RG7446), avelumab (MSB0010718C), FAZ053, KN035, CS1001, SHR-1316, CBT-502, A167, STI-A101, CK-301, BGB-A333, MSB-2311, HLX20, or LY3300054. In some embodiments, the anti-PD-L1 antibody is atezolizumab, avelumab, durvalumab, or tislelizumab. In some embodiments, the anti-PD-L1 antibody is atezolizumab. In some embodiments, the anti-PD-L1 antibody is avelumab. In some embodiments, the anti-PD-L1 antibody is durvalumab. In some embodiments, the anti-PD-L1 antibody is tislelizumab. In some embodiments, the anti-PD-L1 antibody is BMS-935559. In some embodiments, the anti-PD-L1 antibody is MEDI4736. In some embodiments, the anti-PD-L1 antibody is FAZ053. In some embodiments, the anti-PD-L1 antibody is KN035. In some embodiments, the anti-PD-L1 antibody is CS1001. In some embodiments, the anti-PD-L1 antibody is SHR-1316. In some embodiments, the anti-PD-L1 antibody is CBT-502. In some embodiments, the anti- PD-L1 antibody is A167. In some embodiments, the anti-PD-L1 antibody is STI-A101. In some embodiments, the anti-PD-L1 antibody is CK-301. In some embodiments, the anti-PD-L1 antibody is BGB-A333. In some embodiments, the anti-PD-L1 antibody is MSB-2311. In some embodiments, the anti-PD-L1 antibody is HLX20. In some embodiments, the anti-PD-L1 antibody is LY3300054.

In some embodiments, the inhibitor of an immune checkpoint molecule is a small molecule that binds to PD-L1, or a pharmaceutically acceptable salt thereof. In some embodiments, the inhibitor of an immune checkpoint molecule is a small molecule that binds to and internalizes PD-L1, or a pharmaceutically acceptable salt thereof. In some embodiments, the inhibitor of an immune checkpoint molecule is a compound selected from those in US 2018/0179201, US 2018/0179197, US 2018/0179179, US 2018/0179202, US 2018/0177784, US 2018/0177870, U.S. Ser. No. 16/369,654 (filed Mar. 29, 2019), and U.S. Ser. No. 62/688,164, or a pharmaceutically acceptable salt thereof, each of which is incorporated herein by reference in its entirety.

In some embodiments, the inhibitor of an immune checkpoint molecule is an inhibitor of KIR, TIGIT, LAIR1, CD160, 2B4 and TGFR beta.

In some embodiments, the inhibitor is MCLA-145.

In some embodiments, the inhibitor of an immune checkpoint molecule is an inhibitor of CTLA-4, e.g., an anti-CTLA-4 antibody. In some embodiments, the anti-CTLA-4 antibody is ipilimumab, tremelimumab, AGEN1884, or CP-675,206.

In some embodiments, the inhibitor of an immune checkpoint molecule is an inhibitor of LAG3, e.g., an anti-LAG3 antibody. In some embodiments, the anti-LAG3 antibody is BMS-986016, LAG525, INCAGN2385, or eftilagimod alpha (IMP321).

In some embodiments, the inhibitor of an immune checkpoint molecule is an inhibitor of CD73. In some embodiments, the inhibitor of CD73 is oleclumab.

In some embodiments, the inhibitor of an immune checkpoint molecule is an inhibitor of TIGIT. In some embodiments, the inhibitor of TIGIT is OMP-31M32.

In some embodiments, the inhibitor of an immune checkpoint molecule is an inhibitor of VISTA. In some embodiments, the inhibitor of VISTA is JNJ-61610588 or CA-170.

In some embodiments, the inhibitor of an immune checkpoint molecule is an inhibitor of B7-H3. In some embodiments, the inhibitor of B7-H3 is enoblituzumab, MGD009, or 8H9.

In some embodiments, the inhibitor of an immune checkpoint molecule is an inhibitor of KIR. In some embodiments, the inhibitor of KIR is lirilumab or IPH4102.

In some embodiments, the inhibitor of an immune checkpoint molecule is an inhibitor of A2aR. In some embodiments, the inhibitor of A2aR is CPI-444.

In some embodiments, the inhibitor of an immune checkpoint molecule is an inhibitor of TGF-beta. In some embodiments, the inhibitor of TGF-beta is trabedersen, galusertinib, or M7824.

In some embodiments, the inhibitor of an immune checkpoint molecule is an inhibitor of PI3K-gamma. In some embodiments, the inhibitor of PI3K-gamma is IPI-549.

In some embodiments, the inhibitor of an immune checkpoint molecule is an inhibitor of CD47. In some embodiments, the inhibitor of CD47 is Hu5F9-G4 or TTI-621.

In some embodiments, the inhibitor of an immune checkpoint molecule is an inhibitor of CD73. In some embodiments, the inhibitor of CD73 is MEDI9447.

In some embodiments, the inhibitor of an immune checkpoint molecule is an inhibitor of CD70. In some embodiments, the inhibitor of CD70 is cantuzumab or BMS-936561.

In some embodiments, the inhibitor of an immune checkpoint molecule is an inhibitor of TIM3, e.g., an anti-TIM3 antibody. In some embodiments, the anti-TIM3 antibody is INCAGN2390, MBG453, or TSR-022.

In some embodiments, the inhibitor of an immune checkpoint molecule is an inhibitor of CD20, e.g., an anti-CD20 antibody. In some embodiments, the anti-CD20 antibody is obinutuzumab or rituximab.

In some embodiments, the agonist of an immune checkpoint molecule is an agonist of OX40, CD27, CD28, GITR, ICOS, CD40, TLR7/8, and CD137 (also known as 4-1BB).

In some embodiments, the agonist of CD137 is urelumab. In some embodiments, the agonist of CD137 is utomilumab.

In some embodiments, the agonist of an immune checkpoint molecule is an inhibitor of GITR. In some embodiments, the agonist of GITR is TRX518, MK-4166, INCAGN1876, MK-1248, AMG228, BMS-986156, GWN323, MEDI1873, or MEDI6469. In some embodiments, the agonist of an immune checkpoint molecule is an agonist of OX40, e.g., OX40 agonist antibody or OX40L fusion protein. In some embodiments, the anti-OX40 antibody is INCAGN01949, MEDI0562 (tavolimab), MOXR-0916, PF-04518600, GSK3174998, BMS-986178, or 9B12. In some embodiments, the OX40L fusion protein is MEDI6383.

In some embodiments, the agonist of an immune checkpoint molecule is an agonist of CD40. In some embodiments, the agonist of CD40 is CP-870893, ADC-1013, CDX-1140, SEA-CD40, RO7009789, JNJ-64457107, APX-005M, or Chi Lob 7/4.

In some embodiments, the agonist of an immune checkpoint molecule is an agonist of ICOS. In some embodiments, the agonist of ICOS is GSK-3359609, JTX-2011, or MEDI-570.

In some embodiments, the agonist of an immune checkpoint molecule is an agonist of CD28. In some embodiments, the agonist of CD28 is theralizumab.

In some embodiments, the agonist of an immune checkpoint molecule is an agonist of CD27. In some embodiments, the agonist of CD27 is varlilumab.

In some embodiments, the agonist of an immune checkpoint molecule is an agonist of TLR7/8. In some embodiments, the agonist of TLR7/8 is MEDI9197.

The compounds of the present disclosure can be used in combination with bispecific antibodies. In some embodiments, one of the domains of the bispecific antibody targets PD-1, PD-L1, CTLA-4, GITR, OX40, TIM3, LAG3, CD137, ICOS, CD3 or TGF.beta. receptor. In some embodiments, the bispecific antibody binds to PD-1 and PD-L1. In some embodiments, the bispecific antibody that binds to PD-1 and PD-L1 is MCLA-136. In some embodiments, the bispecific antibody binds to PD-L1 and CTLA-4. In some embodiments, the bispecific antibody that binds to PD-L1 and CTLA-4 is AK104.

In some embodiments, the compounds of the disclosure can be used in combination with one or more metabolic enzyme inhibitors. In some embodiments, the metabolic enzyme inhibitor is an inhibitor of IDO1, TDO, or arginase. Examples of IDO1 inhibitors include epacadostat, NLG919, BMS-986205, PF-06840003, IOM2983, RG-70099 and LY338196. Inhibitors of arginase inhibitors include INCB1158.

As provided throughout, the additional compounds, inhibitors, agents, etc. can be combined with the present compound in a single or continuous dosage form, or they can be administered simultaneously or sequentially as separate dosage forms.

II. Cancer Therapies

Cancer cell growth and survival can be impacted by multiple signaling pathways.

Thus, it is useful to combine different enzyme/protein/receptor inhibitors, exhibiting different preferences in the targets which they modulate the activities of, to treat such conditions. Examples of agents that may be combined with compounds of the present disclosure, or solid forms or salts thereof, include inhibitors of the PI3K-AKT-mTOR pathway, inhibitors of the Raf-MAPK pathway, inhibitors of JAK-STAT pathway, inhibitors of beta catenin pathway, inhibitors of notch pathway, inhibitors of hedgehog pathway, inhibitors of Pim kinases, and inhibitors of protein chaperones and cell cycle progression. Targeting more than one signaling pathway (or more than one biological molecule involved in a given signaling pathway) may reduce the likelihood of drug-resistance arising in a cell population, and/or reduce the toxicity of treatment.

The compounds of the present disclosure, or solid forms or salts thereof, can be used in combination with one or more other enzyme/protein/receptor inhibitors for the treatment of diseases, such as cancer. Examples of cancers include solid tumors and liquid tumors, such as blood cancers. For example, the compounds of the present disclosure, or solid forms or salts thereof, can be combined with one or more inhibitors of the following kinases for the treatment of cancer: Akt1, Akt2, Akt3, TGF-□R, PKA, PKG, PKC, CaM-kinase, phosphorylase kinase, MEKK, ERK, MAPK, mTOR, EGFR, HER2, HER3, HER4, INS-R, IGF-1R, IR-R, PDGFαR, PDGFβR, CSFIR, KIT, FLK-II, KDR/FLK-1, FLK-4, fit-1, FGFR1, FGFR2, FGFR3, FGFR4, c-Met, Ron, Sea, TRKA, TRKB, TRKC, FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK and B-Raf. In some embodiments, the compounds of the present disclosure, or solid forms or salts thereof, can be combined with one or more of the following inhibitors for the treatment of cancer. Non-limiting examples of inhibitors that can be combined with the compounds of the present disclosure, or solid forms or salts thereof, for treatment of cancers include an FGFR inhibitor (FGFR1, FGFR2, FGFR3 or FGFR4, e.g., AZD4547, BAY1187982, ARQ087, BGJ398, BIBF1120, TKI258, lucitanib, dovitinib, TAS-120, JNJ-42756493, Debio1347, INCB54828, INCB62079 and INCB63904), a JAK inhibitor (JAK1 and/or JAK2, e.g., ruxolitinib, baricitinib or INCB39110), an IDO inhibitor (e.g., epacadostat and NLG919), an LSD1 inhibitor (e.g., GSK2979552, INCB59872 and INCB60003), a TDO inhibitor, a PI3K-delta inhibitor (e.g., INCB50797 and INCB50465), a PI3K-gamma inhibitor such as a PI3K-gamma selective inhibitor, a CSF1R inhibitor (e.g., PLX3397 and LY3022855), a TAM receptor tyrosine kinases (Tyro-3, Axl, and Mer), an angiogenesis inhibitor, an interleukin receptor inhibitor, bromo and extra terminal family members inhibitors (for example, bromodomain inhibitors or BET inhibitors such as OTX015, CPI-0610, INCB54329 and INCB57643) and an adenosine receptor antagonist or combinations thereof. Inhibitors of HDAC such as panobinostat and vorinostat. Inhibitors of c-Met such as onartuzumab, tivantinib, and INC-280. Inhibitors of BTK such as ibrutinib. Inhibitors of mTOR such as rapamycin, sirolimus, temsirolimus, and everolimus. Inhibitors of Raf, such as vemurafenib and dabrafenib. Inhibitors of MEK such as trametinib, selumetinib and GDC-0973. Inhibitors of Hsp90 (e.g., tanespimycin), cyclin dependent kinases (e.g., palbociclib), PARP (e.g., olaparib) and Pim kinases (LGH447, INCB053914 and SGI-1776) can also be combined with compounds of the present disclosure.

Compounds of the present disclosure, or solid forms or salts thereof, can be used in combination with one or more agents for the treatment of diseases such as cancer. In some embodiments, the agent is an alkylating agent, a proteasome inhibitor, a corticosteroid, or an immunomodulatory agent. Examples of an alkylating agent include bendamustine, nitrogen mustards, ethylenimine derivatives, alkyl sulfonates, nitrosoureas and triazenes, uracil mustard, chlormethine, cyclophosphamide (Cytoxan™), ifosfamide, melphalan, chlorambucil, pipobroman, triethylene-melamine, triethylenethiophosphoramine, busulfan, carmustine, lomustine, streptozocin, dacarbazine, and temozolomide. In some embodiments, the proteasome inhibitor is carfilzomib. In some embodiments, the corticosteroid is dexamethasone (DEX). In some embodiments, the immunomodulatory agent is lenalidomide (LEN) or pomalidomide (POM).

The compounds of the present disclosure, or solid forms or salts thereof, can further be used in combination with other methods of treating cancers, for example by chemotherapy, irradiation therapy, tumor-targeted therapy, adjuvant therapy, immunotherapy or surgery. Examples of immunotherapy include cytokine treatment (e.g., interferons, GM-CSF, G-CSF, IL-2), CRS-207 immunotherapy, cancer vaccine, monoclonal antibody, adoptive T cell transfer, CAR (Chimeric antigen receptor) T cell treatment as a booster for T cell activation, oncolytic virotherapy and immunomodulating small molecules, including thalidomide or JAK1/2 inhibitor and the like. The compounds can be administered in combination with one or more anti-cancer drugs, such as a chemotherapeutics. Example chemotherapeutics include any of: abarelix, abiraterone, afatinib, aflibercept, aldesleukin, alemtuzumab, alitretinoin, allopurinol, altretamine, amsacrine, anastrozole, aphidicolin, arsenic trioxide, asparaginase, axitinib, azacitidine, bevacizumab, bexarotene, baricitinib, bicalutamide, bleomycin, bortezomib, bortezomib, brivanib, buparlisib, busulfan intravenous, busulfan oral, calusterone, camptosar, capecitabine, carboplatin, carmustine, cediranib, cetuximab, chlorambucil, cisplatin, cladribine, clofarabine, crizotinib, cyclophosphamide, cytarabine, dacarbazine, dacomitinib, dactinomycin, dalteparin sodium, dasatinib, dactinomycin, daunorubicin, decitabine, degarelix, denileukin, denileukin diftitox, deoxycoformycin, dexrazoxane, docetaxel, doxorubicin, droloxifene, dromostanolone propionate, eculizumab, enzalutamide, epidophyllotoxin, epirubicin, epothilones, erlotinib, estramustine, etoposide phosphate, etoposide, exemestane, fentanyl citrate, filgrastim, floxuridine, fludarabine, fluorouracil, flutamide, fulvestrant, gefitinib, gemcitabine, gemtuzumab ozogamicin, goserelin acetate, histrelin acetate, ibritumomab tiuxetan, idarubicin, idelalisib, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mithramycin, mitomycin C, mitotane, mitoxantrone, nandrolone phenpropionate, navelbene, necitumumab, nelarabine, neratinib, nilotinib, nilutamide, nofetumomab, oserelin, oxaliplatin, paclitaxel, pamidronate, panitumumab, pazopanib, pegaspargase, pegfilgrastim, pemetrexed disodium, pentostatin, pilaralisib, pipobroman, plicamycin, ponatinib, porfimer, prednisone, procarbazine, quinacrine, ranibizumab, rasburicase, regorafenib, reloxafine, revlimid, rituximab, ruxolitinib, sorafenib, streptozocin, sunitinib, sunitinib maleate, tamoxifen, tegafur, temozolomide, teniposide, testolactone, thalidomide, thioguanine, thiotepa, topotecan, toremifene, tositumomab, trastuzumab, tretinoin, triptorelin, uracil mustard, valrubicin, vandetanib, vinblastine, vincristine, vindesine, vinorelbine, vorinostat and zoledronate.

Other anti-cancer agent(s) include antibody therapeutics such as trastuzumab (Herceptin), antibodies to costimulatory molecules such as CTLA-4 (e.g., ipilimumab or tremelimumab), 4-1BB, antibodies to PD-1 and PD-L1, or antibodies to cytokines (IL-10, TGF-β, etc.). Examples of antibodies to PD-1 and/or PD-L1 that can be combined with compounds of the present disclosure for the treatment of cancer or infections such as viral, bacteria, fungus and parasite infections include, but are not limited to, nivolumab, pembrolizumab, MPDL3280A, MEDI-4736 and SHR-1210.

Other anti-cancer agents include inhibitors of kinases associated cell proliferative disorder. These kinases include but not limited to Aurora-A, CDK1, CDK2, CDK3, CDK5, CDK7, CDK8, CDK9, ephrin receptor kinases, CHK1, CHK2, SRC, Yes, Fyn, Lck, Fer, Fes, Syk, Itk, Bmx, GSK3, JNK, PAK1, PAK2, PAK3, PAK4, PDK1, PKA, PKC, Rsk, and SGK.

Other anti-cancer agents also include those that block immune cell migration such as antagonists to chemokine receptors, including CCR2 and CCR4.

The compounds of the present disclosure, or solid forms or salts thereof, can further be used in combination with one or more anti-inflammatory agents, steroids, immunosuppressants or therapeutic antibodies. The steroids include but are not limited to 17 alpha-ethinylestradiol, diethylstilbestrol, testosterone, prednisone, fluoxymesterone, methylprednisolone, methyltestosterone, prednisolone, triamcinolone, chlorotrianisene, hydroxyprogesterone, aminoglutethimide, and medroxyprogesteroneacetate.

The compounds of the present disclosure, or solid forms or salts thereof, can also be used in combination with lonafarnib (SCH6636), tipifarnib (R115777), L778123, BMS 214662, tezacitabine (MDL 101731), Sml1, triapine, didox, trimidox and amidox.

The compounds of the disclosure, or salts or solid forms thereof, can be combined with another immunogenic agent, such as cancerous cells, purified tumor antigens (including recombinant proteins, peptides, and carbohydrate molecules), cells, and cells transfected with genes encoding immune stimulating cytokines. Non-limiting examples of tumor vaccines that can be used include peptides of melanoma antigens, such as peptides of gp100, MAGE antigens, Trp-2, MARTI and/or tyrosinase, or tumor cells transfected to express the cytokine GM-CSF.

The compounds of the present disclosure, or solid forms or salts thereof, can be used in combination with a vaccination protocol for the treatment of cancer. In some embodiments, the tumor cells are transduced to express GM-CSF. In some embodiments, tumor vaccines include the proteins from viruses implicated in human cancers such as Human Papilloma Viruses (HPV), Hepatitis Viruses (HBV and HCV) and Kaposi's Herpes Sarcoma Virus (KHSV). In some embodiments, the compounds of the present disclosure, or solid forms or salts thereof, can be used in combination with tumor specific antigen such as heat shock proteins isolated from tumor tissue itself. In some embodiments, the compounds of the present disclosure, or solid forms or salts thereof, can be combined with dendritic cells immunization to activate potent anti-tumor responses.

The compounds of the present disclosure, or solid forms or salts thereof, can be used in combination with bispecific macrocyclic peptides that target Fe alpha or Fe gamma receptor-expressing effectors cells to tumor cells. The compounds of the present disclosure, or solid forms or salts thereof, can also be combined with macrocyclic peptides that activate host immune responsiveness.

The compounds of the present disclosure, or solid forms or salts thereof, can be used in combination with bone marrow transplant for the treatment of a variety of tumors of hematopoietic origin.

Suitable antiviral agents contemplated for use in combination with the compounds of the present disclosure can comprise nucleoside and nucleotide reverse transcriptase inhibitors (NRTIs), non-nucleoside reverse transcriptase inhibitors (NNRTIs), protease inhibitors and other antiviral drugs.

Example suitable NRTIs include zidovudine (AZT); didanosine (ddl); zalcitabine (ddC); stavudine (d4T); lamivudine (3TC); abacavir (1592U89); adefovir dipivoxil [bis(POM)-PMEA]; lobucavir (BMS-180194); BCH-10652; emitricitabine [(−)-FTC]; beta-L-FD4 (also called beta-L-D4C and named beta-L-2', 3'-dicleoxy-5-fluoro-cytidene); DAPD, ((−)-beta-D-2,6,-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2,4 (1H,3H)-pyrimidinedione); and (+)-calanolide A (NSC-675451) and B. Typical suitable protease inhibitors include saquinavir (Ro 31-8959); ritonavir (ABT-538); indinavir (MK-639); nelfnavir (AG-1343); amprenavir (141W94); lasinavir (BMS-234475); DMP-450; BMS-2322623; ABT-378; and AG-1 549. Other antiviral agents include hydroxyurea, ribavirin, IL-2, IL-12, pentafuside and Yissum Project No. 11607.

When more than one pharmaceutical agent is administered to a patient, they can be administered simultaneously, separately, sequentially, or in combination (e.g., for more than two agents).

In some embodiments, the compounds of the present disclosure, or solid forms or salts thereof, can be used in combination with INCB086550.

Pharmaceutical Formulations and Dosage Forms

When employed as pharmaceuticals, the compounds of the disclosure can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral, or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This disclosure also includes pharmaceutical compositions which contain, as the active ingredient, the compound of the disclosure or a pharmaceutically acceptable salt thereof, in combination with one or more pharmaceutically acceptable carriers (excipients). In some embodiments, the composition is suitable for topical administration. In making the compositions of the disclosure, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The compounds of the disclosure may be milled using known milling procedures such as wet milling to obtain a particle size appropriate for tablet formation and for other formulation types. Finely divided (nanoparticulate) preparations of the compounds of the disclosure can be prepared by processes known in the art, e.g., see International App. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the disclosure can be formulated so as to provide quick, sustained or delayed release of the active ingredient after administration to the patient by employing procedures known in the art.

The compositions can be formulated in a unit dosage form, each dosage containing from about 5 to about 1000 mg (1 g), more usually about 100 to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, the compositions of the disclosure contain from about 5 to about 50 mg of the active ingredient. One having ordinary skill in the art will appreciate that this embodies compositions containing about 5 to about 10, about 10 to about 15, about 15 to about 20, about 20 to about 25, about 25 to about 30, about 30 to about 35, about 35 to about 40, about 40 to about 45, or about 45 to about 50 mg of the active ingredient.

In some embodiments, the compositions of the disclosure contain from about 50 to about 500 mg of the active ingredient. One having ordinary skill in the art will appreciate that this embodies compositions containing about 50 to about 100, about 100 to about 150, about 150 to about 200, about 200 to about 250, about 250 to about 300, about 350 to about 400, or about 450 to about 500 mg of the active ingredient.

In some embodiments, the compositions of the disclosure contain from about 500 to about 1000 mg of the active ingredient. One having ordinary skill in the art will appreciate that this embodies compositions containing about 500 to about 550, about 550 to about 600, about 600 to about 650, about 650 to about 700, about 700 to about 750, about 750 to about 800, about 800 to about 850, about 850 to about 900, about 900 to about 950, or about 950 to about 1000 mg of the active ingredient.

Similar dosages may be used of the compounds described herein in the methods and uses of the disclosure.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present disclosure. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present disclosure.

The tablets or pills of the present disclosure can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present disclosure can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, for example, liquid paraffin, polyoxyethylene alkyl ether, propylene glycol, white Vaseline, and the like. Carrier compositions of creams can be based on water in combination with glycerol and one or more other components, e.g. glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like. In some embodiments, topical formulations contain at least about 0.1, at least about 0.25, at least about 0.5, at least about 1, at least about 2, or at least about 5 wt % of the compound of the disclosure. The topical formulations can be suitably packaged in tubes of, for example, 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound of the present disclosure can vary according to, for example, the particular use for which the treatment is made, the manner of administration of the compound, the health and condition of the patient, and the judgment of the prescribing physician. The proportion or concentration of a compound of the disclosure in a pharmaceutical composition can vary depending upon a number of factors including dosage, chemical characteristics (e.g., hydrophobicity), and the route of administration. For example, the compounds of the disclosure can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the disclosure can further include one or more additional pharmaceutical agents such as a chemotherapeutic, steroid, anti-inflammatory compound, or immunosuppressant, examples of which are listed herein.

Labeled Compounds and Assay Methods

Another aspect of the present disclosure relates to labeled compounds of the disclosure (radio-labeled, fluorescent-labeled, etc.) that would be useful not only in imaging techniques but also in assays, both in vitro and in vivo, for localizing and quantitating DGK in tissue samples, including human, and for identifying DGK inhibitors by binding of a labeled compound. Substitution of one or more of the atoms of the compounds of the present disclosure can also be useful in generating differentiated ADME (Adsorption, Distribution, Metabolism and Excretion.) Accordingly, the present disclosure includes DGK assays that contain such labeled or substituted compounds.

The present disclosure further includes isotopically-labeled compounds of the disclosure. An "isotopically" or "radio-labeled" compound is a compound of the disclosure where one or more atoms are replaced or substituted by an atom having an atomic mass or mass number different from the atomic mass or mass number typically found in nature (i.e., naturally occurring). Suitable radionuclides that may be incorporated in compounds of the present disclosure include but are not limited to $^{2}H$ (also written as D for deuterium), $^{3}H$ (also written as T for tritium) $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. For example, one or more hydrogen atoms in a compound of the present disclosure can be replaced by deuterium atoms (e.g., one or more hydrogen atoms of a $C_{1-6}$ alkyl group of Formula I can be optionally substituted with deuterium atoms, such as $—CD_3$ being substituted for $—CH_3$). In some embodiments, alkyl groups of the disclosed Formulas (e.g., Formula I) can be perdeuterated.

One or more constituent atoms of the compounds presented herein can be replaced or substituted with isotopes of the atoms in natural or non-natural abundance. In some embodiments, the compound includes at least one deuterium atom. For example, one or more hydrogen atoms in a compound presented herein can be replaced or substituted by deuterium (e.g., one or more hydrogen atoms of a $C_{1-6}$ alkyl group can be replaced by deuterium atoms, such as $—CD_3$ being substituted for $—CH_3$). In some embodiments, the compound includes two or more deuterium atoms. In some embodiments, the compound includes 1-2, 1-3, 1-4, 1-5, 1-6, 1-8, 1-10, 1-12, 1-14, 1-16, 1-18, or 1-20 deuterium atoms. In some embodiments, all of the hydrogen atoms in a compound can be replaced or substituted by deuterium atoms.

In some embodiments, each hydrogen atom of the compounds provided herein, such as hydrogen atoms attached to carbon atoms of alkyl, alkenyl, alkynyl, aryl, phenyl, cycloalkyl, heterocycloalkyl, or heteroaryl substituents or $—C_{1-4}$ alkyl-, alkylene, alkenylene, and alkynylene linking groups, as described herein, is optionally replaced by deuterium atoms.

In some embodiments, each hydrogen atom of the compounds provided herein, such as hydrogen atoms to carbon atoms of alkyl, alkenyl, alkynyl, aryl, phenyl, cycloalkyl, heterocycloalkyl, or heteroaryl substituents or $—C_{1-4}$ alkyl-, alkylene, alkenylene, and alkynylene linking groups, as described herein, is replaced by deuterium atoms (i.e., the alkyl, alkenyl, alkynyl, aryl, phenyl, cycloalkyl, heterocycloalkyl, or heteroaryl substituents, or —$C_{1-4}$ alkyl-, alkylene, alkenylene, and alkynylene linking groups are perdeuterated).

In some embodiments, 1, 2, 3, 4, 5, 6, 7, 8, 9, 10, 11, or 12 hydrogen atoms, attached to carbon atoms of alkyl, alkenyl, alkynyl, aryl, phenyl, cycloalkyl, heterocycloalkyl, or heteroaryl substituents or —$C_{1-4}$ alkyl-, alkylene, alkenylene, and alkynylene linking groups, as described herein, are optionally replaced by deuterium atoms.

In some embodiments, 1, 2, 3, 4, 5, 6, 7, or 8 hydrogen atoms, attached to carbon atoms of alkyl, alkenyl, alkynyl, aryl, phenyl, cycloalkyl, heterocycloalkyl, or heteroaryl substituents or —$C_{1-4}$ alkyl-, alkylene, alkenylene, and alkynylene linking groups, as described herein, are optionally replaced by deuterium atoms.

In some embodiments, the compound provided herein (e.g., the compound of any of Formulas I-IX), or a pharmaceutically acceptable salt thereof, comprises at least one deuterium atom.

In some embodiments, the compound provided herein (e.g., the compound of any of Formulas I-IX), or a pharmaceutically acceptable salt thereof, comprises two or more deuterium atoms.

In some embodiments, the compound provided herein (e.g., the compound of any of Formulas I-IX), or a pharmaceutically acceptable salt thereof, comprises three or more deuterium atoms.

In some embodiments, for a compound provided herein (e.g., the compound of any of Formulas I-IX), or a pharmaceutically acceptable salt thereof, all of the hydrogen atoms are replaced by deuterium atoms (i.e., the compound is "perdeuterated").

Synthetic methods for including isotopes into organic compounds are known in the art (Deuterium Labeling in Organic Chemistry by Alan F. Thomas (New York, N.Y., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765; The Organic Chemistry of Isotopic Labelling by James R. Hanson, Royal Society of Chemistry, 2011). Isotopically labeled compounds can be used in various studies such as NMR spectroscopy, metabolism experiments, and/or assays.

Substitution with heavier isotopes, such as deuterium, may afford certain therapeutic advantages resulting from greater metabolic stability, for example, increased in vivo half-life or reduced dosage requirements, and hence may be preferred in some circumstances. (see e.g., A. Kerekes et. al. J. *Med. Chem.* 2011, 54, 201-210; R. Xu et. al. J. *Label Compd. Radiopharm.* 2015, 58, 308-312). In particular, substitution at one or more metabolism sites may afford one or more of the therapeutic advantages.

The radionuclide that is incorporated in the instant radio-labeled compounds will depend on the specific application of that radio-labeled compound. For example, for in vitro DGK labeling and competition assays, compounds that incorporate $^{3}H$, $^{14}C$, $^{82}Br$, $^{125}I$, $^{131}I$ or $^{35}S$ can be useful. For radio-imaging applications $^{11}C$, $^{18}F$, $^{125}I$, $^{123}I$, $^{124}I$, $^{131}I$, $^{75}Br$, $^{76}Br$ or $^{77}Br$ can be useful.

It is understood that a "radio-labeled" or "labeled compound" is a compound that has incorporated at least one radionuclide. In some embodiments, the radionuclide is selected from the group consisting of $^{3}H$, $^{14}C$, $^{125}I$, $^{35}S$ and $^{82}Br$.

The present disclosure can further include synthetic methods for incorporating radio-isotopes into compounds of the disclosure. Synthetic methods for incorporating radio-isotopes into organic compounds are well known in the art, and an ordinary skill in the art will readily recognize the methods applicable for the compounds of disclosure.

A labeled compound of the disclosure can be used in a screening assay to identify/evaluate compounds. For example, a newly synthesized or identified compound (i.e., test compound) which is labeled can be evaluated for its ability to bind DGK by monitoring its concentration variation when contacting with DGK, through tracking of the labeling. For example, a test compound (labeled) can be evaluated for its ability to reduce binding of another compound which is known to bind to DGK (i.e., standard compound). Accordingly, the ability of a test compound to compete with the standard compound for binding to DGK directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present disclosure also includes pharmaceutical kits useful, for example, in the treatment or prevention of DGK-associated diseases or disorders as described herein, which include one or more containers containing a pharmaceutical composition comprising a therapeutically effective amount of a compound of the disclosure. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results.

EXAMPLES

Preparatory LC-MS purifications of some of the compounds prepared were performed on Waters mass directed fractionation systems. The basic equipment setup, protocols, and control software for the operation of these systems have been described in detail in the literature (see e.g. "Two-Pump At Column Dilution Configuration for Preparative LC-MS", K. Blom, *J. Combi. Chem.,* 4, 295 (2002); "Optimizing Preparative LC-MS Configurations and Methods for Parallel Synthesis Purification", K. Blom, R. Sparks, J. Doughty, G. Everlof, T. Hague, A. Combs, *J. Combi. Chem.,* 5, 670 (2003); and "Preparative LC-MS Purification: Improved Compound Specific Method Optimization", K. Blom, B. Glass, R. Sparks, A. Combs, *J. Combi. Chem.,* 6, 874-883 (2004)). The compounds separated were typically subjected to analytical liquid chromatography mass spectrometry (LCMS) for purity analysis under the following conditions: Instrument; Agilent 1100 series, LC/MSD, Column: Waters Sunfire™ $C_{18}$ 5 μm, 2.1×50 mm, Buffers:

mobile phase A: 0.025% TFA in water and mobile phase B: acetonitrile; gradient 2% to 80% of B in 3 minutes with flow rate 2.0 mL/minute.

Some of the compounds prepared were also separated on a preparative scale by reverse-phase high performance liquid chromatography (RP-HPLC) with MS detector or flash chromatography (silica gel) as indicated in the Examples. Typical preparative reverse-phase high performance liquid chromatography (RP-HPLC) column conditions are as follows:

pH=2 purifications: Waters Sunfire™ $C_{18}$ 5 μm, 19×100 mm, eluting with mobile phase A: 0.1% TFA (trifluoroacetic acid) in water and mobile phase B: acetonitrile; the flow rate was 30 mL/minute, the separating gradient was optimized for each compound using the Compound Specific Method Optimization protocol as described in the literature (see e.g. "Preparative LCMS Purification: Improved Compound Specific Method Optimization", K. Blom, B. Glass, R. Sparks, A. Combs, *J. Comb. Chem.,* 6, 874-883 (2004)). For purifications using a 30×100 mm column, the flow rate was 60 mL/minute.

pH=10 purifications: Waters XBridge™ $C_{18}$ 5 μm, 19×100 mm column, eluting with mobile phase A: 0.15% $NH_4OH$ in water and mobile phase B: acetonitrile; the flow rate was 30 mL/minute, the separating gradient was optimized for each compound using the Compound Specific Method Optimization protocol as described in the literature (see e.g. "Preparative LCMS Purification: Improved Compound Specific Method Optimization", K. Blom, B. Glass, R. Sparks, A. Combs, *J. Comb. Chem.,* 6, 874-883 (2004)). For purifications using a 30×100 mm column, the flow rate was 60 mL/minute.

Intermediate 1. 8-Hydroxy-5-methyl-6-oxo-5,6-dihydro-1,5-naphthyridine-2-carbonitrile

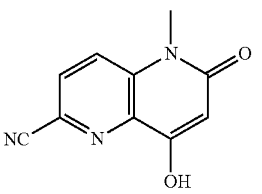

Step 1: Ethyl 3-acetamido-6-bromopicolinate

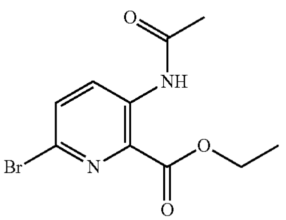 [SMILES: CCOC(=O)c1nc(Br)ccc1NC(C)=O]

To a mixture of ethyl 3-amino-6-bromopicolinate (5.00 g, 20.4 mmol, Combi-Blocks QH-5934) in THF (40 mL) was added acetic anhydride (19.3 mL, 204 mmol) and the reaction mixture was stirred at 90° C. overnight. After cooling to rt, the reaction mixture was concentrated in vacuo. To the crude residue was added EtOAc (10 mL) followed by $Et_2O$ (30 mL) and hexanes (200 mL) and the mixture was slurried for 30 mins. The solid precipitate was collected via vacuum filtration, washed with hexanes, and dried under air to afford the desired product (4.35 g, 74% yield) as an off-white solid. LC-MS calculated for $C_{10}H_{12}BrN_2O_3$ $(M+H)^+$: m/z=287.0. found 287.1.

Step 2: Ethyl 3-acetamido-6-cyanopicolinate

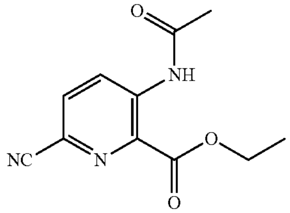 [SMILES: CCOC(=O)c1nc(C#N)ccc1NC(C)=O]

In a microwave vial with a stir bar, a mixture of ethyl 3-acetamido-6-bromopicolinate (1.7 g, 5.9 mmol) and copper(I) cyanide (0.80 g, 8.9 mmol) in DMF (15 mL) in a reaction vial was irradiated in a microwave reactor at 200° C. for 8 min. After cooling to rt, the reaction mixture was diluted with $CH_2Cl_2$ and water and the insoluble material was removed via filtration. The filtrate was transferred to a separatory funnel and after phase separation the organic phase was removed and the aqueous phase was extracted twice more with $CH_2Cl_2$. The combined organic phases were washed with sat. aq. NaCl, dried over $MgSO_4$, and concentrated. The crude residue was purified by flash column chromatography ($SiO_2$, EtOAc/hexanes) to afford the desired product (0.84 g, 61% yield). LC-MS calculated for $C_{11}H_{12}N_3O_3$ $(M+H)^+$: m/z=234.1. found 234.0.

Step 3: Ethyl 6-cyano-3-(N-methylacetamido)picolinate

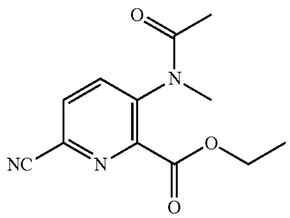 [SMILES: CCOC(=O)c1nc(C#N)ccc1N(C)C(C)=O]

A mixture of ethyl 3-acetamido-6-cyanopicolinate (2.40 g, 10.3 mmol), cesium carbonate (7.38 g, 22.64 mmol) and methyl iodide (1.3 mL, 20.6 mmol) in DMF (50 mL) was stirred at rt for 3 hours. The reaction mixture was diluted with $CH_2Cl_2$ and sat. aq. NaCl and shaken in a separatory funnel. After phase separation, the organic phase was removed and the aqueous phase was extracted once more with $CH_2Cl_2$. The combined organic solution was dried over $Na_2SO_4$ and concentrated. The crude residue was purified by flash column chromatography ($SiO_2$, EtOAc/hexanes) to afford the desired product (2.24 g, 88% yield). LC-MS calculated for $C_{12}H_{14}N_3O_3$ $(M+H)^+$: m/z=248.1. found 248.1.

Step 4: 8-Hydroxy-5-methyl-6-oxo-5,6-dihydro-1,5-naphthyridine-2-carbonitrile

A mixture ethyl 6-cyano-3-(N-methylacetamido)picolinate (0.82 g, 3.3 mmol) in anhydrous THF (30 ml) was cooled to −78° C. in a dry ice/acetone bath before a 0.5 molar solution of potassium bis(trimethylsilyl)amide in toluene (8 mL, 4 mmol, Aldrich 277304) was added dropwise over ca. 30 min. The reaction mixture was stirred at −78° C. for an additional 20 min before the dry ice/acetone bath was removed and the mixture was stirred at rt for 1 h. The reaction was diluted with $H_2O$ and extracted with EtOAc. After phase separation, the aqueous phase was removed and acidified with 1 molar aq. HCl. The fine yellow precipitate that formed was collected via filtration, washed with $H_2O$ (2 mL), and dried under vacuum to afford the desired product (0.47 g, 70% yield). LC-MS calculated for $C_{10}H_8N_3O_2$ $(M+H)^+$: m/z=202.1. found 202.1.

Intermediate 2. 6-Cyano-1-methyl-3-nitro-2-oxo-1,2-dihydro-1,5-naphthyridin-4-yl trifluoromethanesulfonate

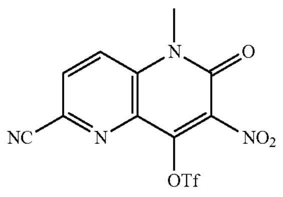 [SMILES: Cn1c(=O)c([N+](=O)[O-])c(OS(=O)(=O)C(F)(F)F)c2nc(C#N)ccc21]

Step 1: 8-Hydroxy-5-methyl-7-nitro-6-oxo-5,6-dihydro-1,5-naphthyridine-2-carbonitrile

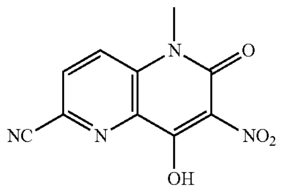 [SMILES: Cn1c(=O)c([N+](=O)[O-])c(O)c2nc(C#N)ccc21]

To a mixture of 8-hydroxy-5-methyl-6-oxo-5,6-dihydro-1,5-naphthyridine-2-carbonitrile (Intermediate 1, 603 mg, 3.0 mmol) in AcOH (3.0 mL) was added nitric acid (0.4 mL, 9 mmol) and the mixture was stirred at 100° C. for 30 min. After cooling to rt, the mixture was diluted with ice water (30 mL) and slurried for 30 mins. The solid precipitate that formed was collected via filtration, washed with water, and dried under air to afford the desired product (492 mg, 67% yield) as a yellow solid. The crude material obtained was used directly without further purification. LC-MS calculated for $C_{10}H_7N_4O_4$ $(M+H)^+$: m/z=247.0. found 247.0.

Step 2: 6-Cyano-1-methyl-3-nitro-2-oxo-1,2-dihydro-1,5-naphthyridin-4-yl trifluoromethanesulfonate In an oven-dried microwave vial with a stir bar, a mixture of 8-hydroxy-5-methyl-7-nitro-6-oxo-5,6-dihydro-1,5-naphthyridine-2-carbonitrile (492 mg, 2.00 mmol) in $CH_2Cl_2$ (10 mL) was irradiated in a microwave reactor at 70° C. for 15 mins. After cooling to rt, 4-dimethylaminopyridine (24.2 mg, 0.20 mmol) and N-ethyl-N-isopropylpropan-2-amine (0.57 mL, 3.3 mmol) were added and the mixture was purged with nitrogen and cooled to 0° C. in an ice bath before trifluoromethanesulfonic anhydride (0.5 mL, 3 mmol, Aldrich 176176) was added dropwise. The ice bath was removed and the mixture was stirred at rt for 4 h. The reaction mixture was diluted with sat. aq. $NaHCO_3$ and extracted with $CH_2Cl_2$. The combined organic phases were dried over $MgSO_4$ and concentrated. The crude material obtained was used directly without further purification. LC-MS calculated for $C_{11}H_6F_3N_4O_6S$ $(M+H)^+$: m/z=379.0. found 379.1.

Intermediates 3 and 4. tert-Butyl 4-(6-cyano-1-methyl-3-nitro-2-oxo-1,2-dihydro-1,5-naphthyridin-4-yl)-3-(2-methoxy-2-oxoethyl)piperazine-1-carboxylate

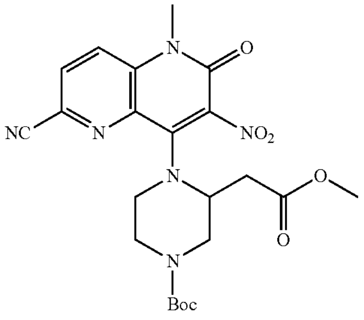

To a mixture of 6-cyano-1-methyl-3-nitro-2-oxo-1,2-dihydro-1,5-naphthyridin-4-yl trifluoromethanesulfonate (Intermediate 2, 340 mg, 0.9 mmol), tert-butyl 3-(2-methoxy-2-oxoethyl)piperazine-1-carboxylate (233 mg, 0.901 mmol, AstaTech 66875) in $CH_3CN$ (4.5 mL) was added N-ethyl-N-isopropylpropan-2-amine (0.47 mL, 2.7 mmol) and the reaction mixture was stirred at 85° C. for 4 h. After cooling to rt, the reaction mixture was concentrated in vacuo and the crude residue was purified using flash column chromatography ($SiO_2$, EtOAc/hexanes) to afford the desired product (mixture of enantiomers, 98 mg, 22% yield) as a yellowish-brown waxy solid. The racemic mixture was purified by preparative chiral HPLC (ChiralPak D3 N-5 column, 250×20 mm, 5 μm, eluting with a gradient of 70% EtOH in hexanes, at flow rate of 20 mL/min).

Intermediate 3: Retention time on preparative chiral HPLC $t_r$=9.6 min, LC-MS calculated for $C_{22}H_{27}N_6O_7$ $(M+H)^+$: m/z=487.2. found 487.3.

Intermediate 4: Retention time on preparative chiral HPLC $t_r$=12.4 min, LC-MS calculated for $C_{22}H_{27}N_6O_7$ $(M+H)^+$: m/z=487.2. found 487.3.

Intermediate 5. (R)-(4-(Bis(4-fluorophenyl)methyl)piperazin-2-yl)methanol hydrochloride

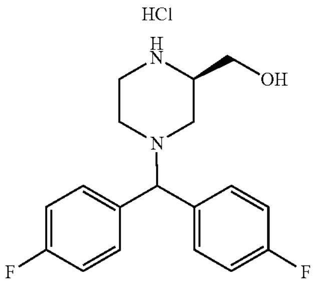 [SMILES: Cl ; OC[C@H]1CN(C(c2ccc(F)cc2)c2ccc(F)cc2)CCN1]

Step 1: tert-Butyl (R)-4-(bis(4-fluorophenyl)methyl)-2-(hydroxymethyl)piperazine-1-carboxylate

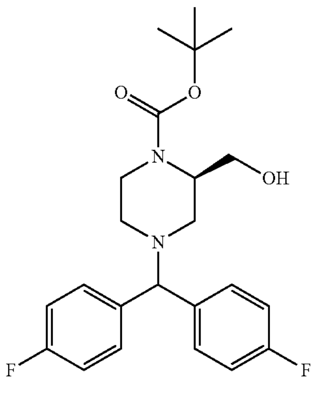 [SMILES: CC(C)(C)OC(=O)N1CCN(C(c2ccc(F)cc2)c2ccc(F)cc2)C[C@@H]1CO]

A mixture of tert-butyl (R)-2-(hydroxymethyl)piperazine-1-carboxylate (2.16 g, mmol, AstaTech 56773), 4,4'-(chloromethylene)bis(fluorobenzene) (2.86 g, 12.00 mmol, Combi-Blocks QA-4728) and N-ethyl-N-isopropylpropan-2-amine (5.24 mL, 30.0 mmol) in $CH_3CN$ (25 mL) was stirred at 85° C. overnight. After cooling to rt, the reaction mixture was concentrated in vacuo and the crude residue was purified using flash column chromatography (40 g $SiO_2$, EtOAc/hexanes) to afford the desired product (2.54 g, 61% yield) as a light yellow waxy solid. LC-MS calculated for $C_{23}H_{29}F_2N_2O_3$ $(M+H)^+$: m/z=419.2. found 419.2.

Step 2: (R)-(4-(Bis(4-fluorophenyl)methyl)piperazin-2-yl)methanol hydrochloride

To a mixture of tert-butyl (R)-4-(bis(4-fluorophenyl)methyl)-2-(hydroxymethyl)piperazine-1-carboxylate (2.54 g, 6.07 mmol) in THF (30 mL) was added a 4 molar solution of HCl in 1,4-dioxane (15 mL, 60 mmol) and the reaction mixture was purged with $N_2$ and stirred at 80° C. for 2 h. After cooling to rt, the reaction mixture was concentrated to ½ volume, diluted with $Et_2O$ (30 mL) and hexanes (60 mL), and slurried for 30 mins. The solid precipitate was collected via filtration, washed with hexanes, and dried under vacuum to afford the desired product (2.05 g, 95% yield) as a white solid. LC-MS calculated for $C_{18}H_{21}F_2N_2O$ $(M+H)^+$: m/z=319.2. found 319.1.

Intermediate 6: (R)-11-(Bis(4-fluorophenyl)methyl)-2-bromo-5-methyl-9,9a,10,11,12,13-hexahydro-6H-pyrazino[2',1':3,4][1,4]oxazepino[6,5-c][1,5]naphthyridine-6,7(5H)-dione

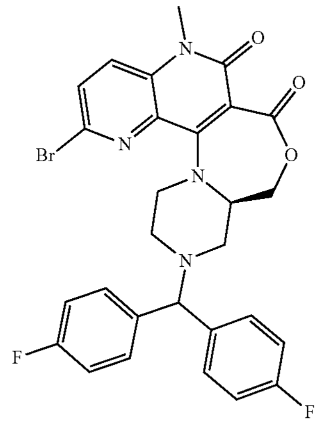 [SMILES: Cn1c(=O)c2c(c3nc(Br)ccc31)N1CCN(C(c3ccc(F)cc3)c3ccc(F)cc3)C[C@@H]1COC2=O]

Step 1: Methyl 6-bromo-3-(3-methoxy-3-oxopropanamido)picolinate

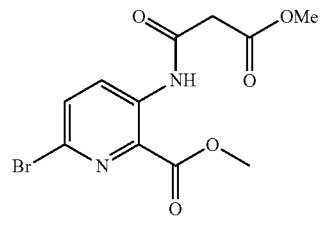 [SMILES: COC(=O)CC(=O)Nc1ccc(Br)nc1C(=O)OC]

A mixture of methyl 3-amino-6-bromopicolinate (1.2 g, 5.19 mmol) and pyridine (0.822 g, 10.4 mmol) in $CH_2Cl_2$ (20 mL) was cooled to 0° C. before a mixture of methyl 3-chloro-3-oxopropanoate (0.851 g, 6.23 mmol) in $CH_2Cl_2$ (5.0 mL) was added dropwise. The reaction was allowed to warm to rt and stirred for 2 h. LC-MS indicated full conversion. The reaction was diluted with $CH_2Cl_2$ and washed with 1 N HCl. The organic phase was dried over $Na_2SO_4$, concentrated, and the crude residue was purified using flash column chromatography (24 g $SiO_2$, EtOAc/hexanes) to afford the desired product (1.07 g, 62% yield) white solid. LC-MS calculated for $C_{11}H_{12}BrN_2O_5$ $(M+H)^+$: m/z=331.0. found 331.1.

Step 2: Methyl 6-bromo-4-hydroxy-2-oxo-1,2-dihydro-1,5-naphthyridine-3-carboxylate

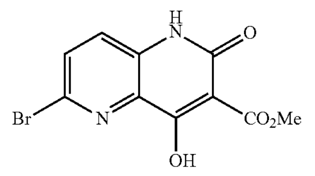 [SMILES: COC(=O)c1c(O)c2nc(Br)ccc2[nH]c1=O]

To a mixture of methyl 6-bromo-3-(3-methoxy-3-oxopropanamido)picolinate (1.07 g, 3.23 mmol) in MeOH (10.0 mL) was added a 5 M solution of NaOMe in MeOH (2.1 mL, 10.5 mmol) dropwise. White precipitate formed immediately and the cloudy solution was stirred at rt for 1 h. The reaction mixture was quenched via the addition of water and acidified with 1 N HCl. The solid precipitate was collected by filtration and washed with MeOH to afford the desired product (700 mg, 72% yield) as red solid. LC-MS calculated for $C_{10}H_8BrN_2O_4$ $(M+H)^+$: m/z=299.0. found 299.0.

Step 3: Methyl 6-bromo-4-hydroxy-1-methyl-2-oxo-1,2-dihydro-1,5-naphthyridine-3-carboxylate

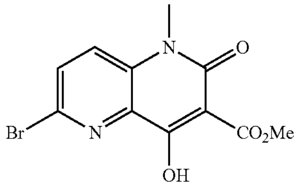 [SMILES: COC(=O)c1c(O)c2nc(Br)ccc2n(C)c1=O]

To a mixture of methyl 6-bromo-4-hydroxy-2-oxo-1,2-dihydro-1,5-naphthyridine-3-carboxylate (700 mg, 2.34 mmol) in DMF (30 mL) was added a 1 M solution of LiHMDS in THF (7.8 mL, 7.8 mmol) dropwise and the reaction was stirred at rt for 5 mins before methyl iodide (1.84 g, 13 mmol) was added and the mixture was stirred at rt for 1 h. LC-MS indicated full conversion. The reaction mixture was quenched via the addition of water, acidified with 1 N HCl, and extracted with EtOAc. The combined organic phases were washed with brine (3×), dried over $Na_2SO_4$, and concentrated to afford the desired product (450 mg, 61% yield) as red solid. The crude material obtained was used directly without further purification. LC-MS calculated for $C_{11}H_{10}BrN_2O_4$ $(M+H)^+$: m/z=313.0. found 313.0.

Step 4: Methyl 6-bromo-1-methyl-2-oxo-4-(((trifluoromethyl)sulfonyl)oxy)-1,2-dihydro-1,5-naphthyridine-3-carboxylate

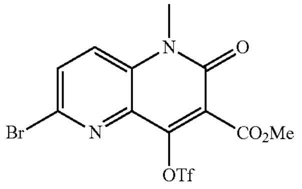 [SMILES: COC(=O)c1c(OS(=O)(=O)C(F)(F)F)c2nc(Br)ccc2n(C)c1=O]

A mixture of methyl 6-bromo-4-hydroxy-1-methyl-2-oxo-1,2-dihydro-1,5-naphthyridine-3-carboxylate (125 mg, 0.40 mmol) and 4-dimethylaminopyridine (6.4 mg, mmol) in $CH_2Cl_2$ (2.0 mL) was cooled to 0° C. in an ice-bath before N-ethyl-N-isopropylpropan-2-amine (0.11 mL, 0.82 mmol) and trifluoromethanesulfonic anhydride (0.10 mL, 0.75 mmol) were added dropwise. The ice-bath was removed and the reaction mixture was stirred at rt for 3 h. LC-MS indicated full conversion. The reaction mixture was quenched via the addition of sat. aq. $NaHCO_3$ and extracted with $CH_2Cl_2$. The combined organic phases were dried over $Na_2SO_4$ and concentrated to afford the desired product as brown solid. The crude material obtained was used directly without further purification. LC-MS calculated for $C_{12}H_9BrF_3N_2O_6S$ $(M+H)^+$: m/z=444.9. found 444.9.

Step 5: Methyl (R)-4-(4-(bis(4-fluorophenyl)methyl)-2-(hydroxymethyl)piperazin-1-yl)-6-bromo-1-methyl-2-oxo-1,2-dihydro-1,5-naphthyridine-3-carboxylate

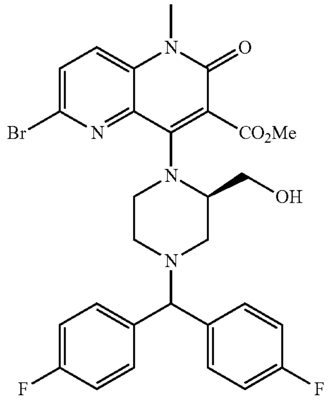 [SMILES: COC(=O)c1c(N2CCN(C(c3ccc(F)cc3)c3ccc(F)cc3)C[C@@H]2CO)c2nc(Br)ccc2n(C)c1=O]

To a mixture of methyl 6-bromo-1-methyl-2-oxo-4-(((trifluoromethyl)sulfonyl)oxy)-1,2-dihydro-1,5-naphthyridine-3-carboxylate (Step 4) in $CH_3CN$ (3.0 mL) was added N-ethyl-N-isopropylpropan-2-amine (0.17 mL, 1.26 mmol) and (R)-(4-(bis(4-fluorophenyl)methyl)piperazin-2-yl)methanol hydrochloride (Intermediate 5, 158 mg, 0.44 mmol) and the reaction mixture was stirred at 75° C. for 1 h. LC-MS indicated full conversion. After cooling to rt, the reaction mixture was concentrated in vacuo and the crude residue was purified by flash column chromatography (24 g $SiO_2$, EtOAc/hexanes) to afford the desired product (130 mg, 53% yield over 2 steps) as a yellow solid. LC-MS calculated for $C_{29}H_{28}BrF_2N_4O_4$ $(M+H)^+$: m/z=613.1. found 613.2.

Step 6: (R)-11-(Bis(4-fluorophenyl)methyl)-2-bromo-5-methyl-9,9a,10,11,12,13-hexahydro-6H-pyrazino[2',1':3,4][1,4]oxazepino[6,5-c][1,5]naphthyridine-6,7(5H)-dione To a mixture of methyl (R)-4-(4-(bis(4-fluorophenyl)methyl)-2-(hydroxymethyl)piperazin-1-yl)-6-bromo-1-methyl-2-oxo-1,2-dihydro-1,5-naphthyridine-3-carboxylate (200 mg, 0.326 mmol) in toluene (2.0 mL) was added p-toluenesulfonic acid monohydrate (6.20 mg, 0.033 mmol) and the reaction mixture was stirred at 95° C. overnight. LC-MS indicated the full conversion. After cooling to rt, the reaction mixture was concentrated in vacuo and the crude residue was purified by flash column chromatography (4 g $SiO_2$, EtOAc/hexanes) to afford the desired product (140 mg, 74% yield) as yellow solid. LC-MS calculated for $C_{28}H_{24}BrF_2N_4O_3$ $(M+H)^+$: m/z=581.1. found 581.0.

Intermediate 7: Methyl 6-bromo-3-(3-methoxy-3-oxopropanamido)pyrazine-2-carboxylate

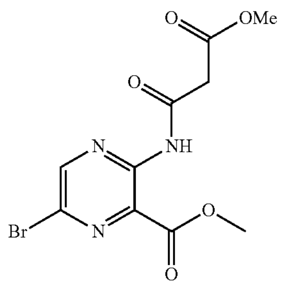

+

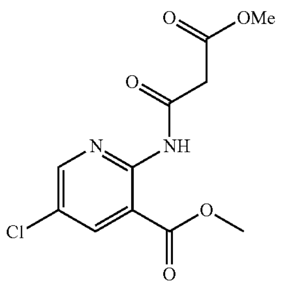

~1:1

To a mixture of methyl 3-amino-6-bromopyrazine-2-carboxylate (2.32 g, 10.0 mmol) in 1,2-DCE (20 mL) was added methyl 3-chloro-3-oxopropanoate (1.64 g, 12.0 mmol) in $CH_2Cl_2$ (5.0 mL) dropwise at rt before the reaction mixture was heated to refluxing for 1 hour. After cooling to rt, the reaction mixture was diluted with $CH_2Cl_2$, washed with 1 N HCl, dried over $Na_2SO_4$, and concentrated to afford the desired product mixture (1.40 g). The crude material obtained was used directly without further purification. LC-MS calculated for $C_{10}H_{11}BrN_3O_5$ $(M+H)^+$: m/z=332.0. found 331.9. LC-MS calculated for $C_{10}H_{11}ClN_3O_5$ $(M+H)^+$: m/z=288.0. found 288.0.

Intermediate 8: Methyl (R)-8-(4-(bis(4-fluorophenyl)methyl)-2-(hydroxymethyl)piperazin-1-yl)-2-bromo-5-methyl-6-oxo-5,6-dihydropyrido[2,3-b]pyrazine-7-carboxylate

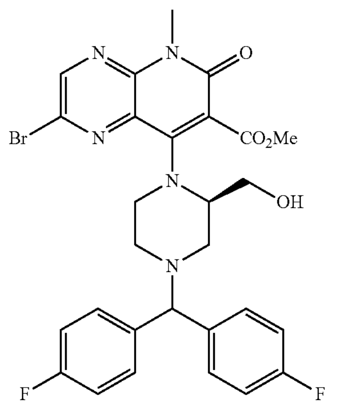

+

-continued

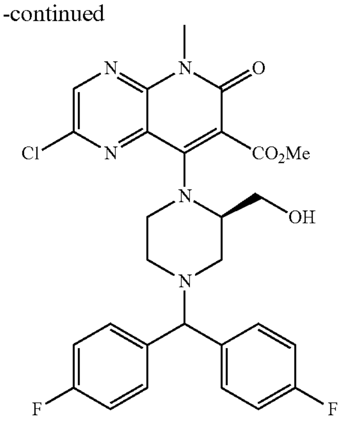

~1:1

The title compound mixture was prepared according to the procedures described in Intermediate 6, Steps 2-5 with Intermediate 7 replacing methyl 6-bromo-3-(3-methoxy-3-oxopropanamido)picolinate in Step 2. LC-MS calculated for $C_{28}H_{27}BrF_2N_5O_4$ $(M+H)^+$: m/z=614.2. found 614.0. LC-MS calculated for $C_{28}H_{27}ClF_2N_5O_4$ $(M+H)^+$: m/z=570.2. found 570.1.

Intermediate 9: (R)-11-(Bis(4-fluorophenyl)methyl)-2-bromo-5-methyl-9,9a,10,11,12,13-hexahydro-6H-pyrazino[2,1-c]pyrazino[2',3': 5,6]pyrido[4,3-e][1,4]oxazepine-6,7(5H)-dione

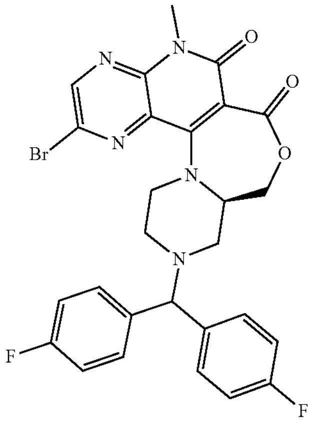

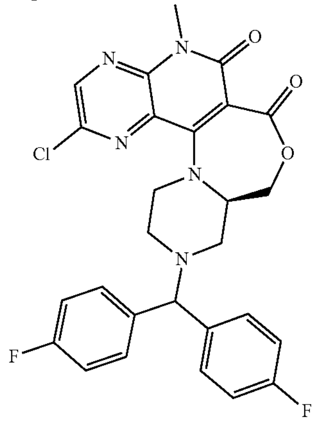

~1:1

To a mixture of Intermediate 8 (130 mg, 0.21 mmol) in dry $CH_2Cl_2$ (2.0 mL) was added a 2 M solution of $AlMe_3$ in toluene (0.13 mL, 0.26 mmol) dropwise and the reaction mixture was stirred at rt overnight. The mixture was quenched by slowly addition of aq. $NaHCO_3$, slurried with Celite, and filtered. The filtrate was extracted with $CH_2Cl_2$, dried over $Na_2SO_4$, and concentrated. The crude residue was purified by flash column chromatography (4 g $SiO_2$, EtOAc/hexanes) to afford desired product mixture as yellow foamy solid (90 mg). LC-MS calculated for $C_{27}H_{23}BrF_2N_5O_3$ $(M+H)^+$: m/z=582.1. found 582.1. LC-MS calculated for $C_{27}H_{23}ClF_2N_5O_3$ $(M+H)^+$: m/z=538.1. found 538.1.

Intermediate 10. (S)-(4-(Bis(4-fluorophenyl)methyl)piperazin-2-yl)methanol hydrochloride

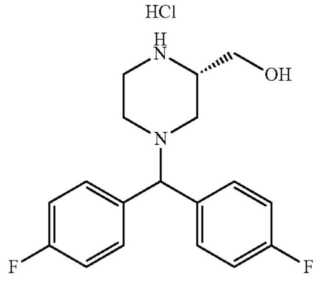 [SMILES: Cl ; OC[C@@H]1CN(C(c2ccc(F)cc2)c2ccc(F)cc2)CCN1]

The title compound was prepared according to the procedures described in Intermediate 5, with tert-butyl (S)-2-(hydroxymethyl)piperazine-1-carboxylate replacing tert-butyl (R)-2-(hydroxymethyl)piperazine-1-carboxylate. LC-MS calculated for $C_{18}H_{21}F_2N_2O$ $(M+H)^+$: m/z=319.2. found 319.0.

Intermediate 11: Methyl (S)-4-(4-(bis(4-fluorophenyl)methyl)-2-(hydroxymethyl)piperazin-1-yl)-6-bromo-1-methyl-2-oxo-1,2-dihydro-1,5-naphthyridine-3-carboxylate

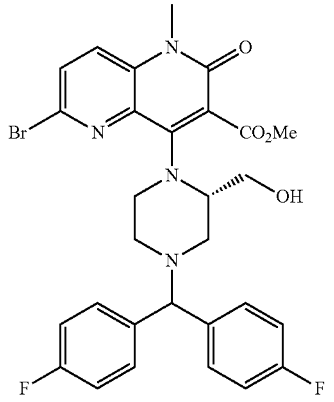 [SMILES: COC(=O)c1c(N2CCN(C(c3ccc(F)cc3)c3ccc(F)cc3)C[C@H]2CO)c2nc(Br)ccc2n(C)c1=O]

The title compound was prepared according to the procedures described in Intermediate 6, Steps 1-5 with (S)-(4-(bis(4-fluorophenyl)methyl)piperazin-2-yl)methanol hydrochloride (Intermediate 10) replacing (R)-(4-(bis(4-fluorophenyl)methyl)piperazin-2-yl)methanol hydrochloride in Step 5. LC-MS calculated for $C_{29}H_{28}BrF_2N_4O_4$ $(M+H)^+$: m/z=613.1. found 613.1.

Intermediate 12: (S)-11-(Bis(4-fluorophenyl)methyl)-2-bromo-5-methyl-9,9a,10,11,12,13-hexahydro-6H-pyrazino[2',1':3,4][1,4]oxazepino[6,5-c][1,5]naphthyridine-6,7(5H)-dione

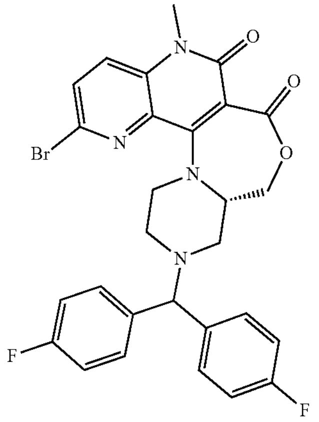 [SMILES: Cn1c(=O)c2c(c3nc(Br)ccc31)N1CCN(C(c3ccc(F)cc3)c3ccc(F)cc3)C[C@H]1COC2=O]

To a mixture of methyl (S)-4-(4-(bis(4-fluorophenyl)methyl)-2-(hydroxymethyl)piperazin-1-yl)-6-bromo-1-methyl-2-oxo-1,2-dihydro-1,5-naphthyridine-3-carboxylate (Intermediate 11, 275 mg, 0.45 mmol) in dry $CH_2Cl_2$ (2.0 mL) was added a 2 M solution of $AlMe_3$ in toluene (0.27 mL, 0.54 mmol) dropwise and the reaction mixture was stirred at rt overnight. The mixture was quenched by slowly addition of aq. $NaHCO_3$, slurried with Celite, and filtered. The filtrate was extracted with $CH_2Cl_2$, dried over $Na_2SO_4$, and concentrated. The crude residue was purified by flash column chromatography (4 g $SiO_2$, EtOAc/hexanes) to afford desired product mixture as yellow foamy solid. LC-MS calculated for $C_{28}H_{24}BrF_2N_4O_3$ $(M+H)^+$: m/z=581.1. found 581.0.

Intermediate 13. ((2R,5R)-4-(Bis(4-fluorophenyl)methyl)-5-methylpiperazin-2-yl)methanol

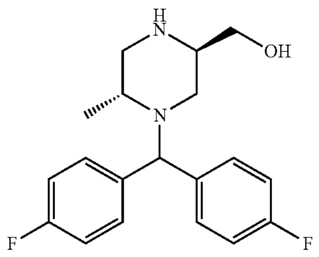 [SMILES: C[C@@H]1CN[C@@H](CO)CN1C(c1ccc(F)cc1)c1ccc(F)cc1]

Step 1: Benzyl (2R,5R)-2-(hydroxymethyl)-5-methylpiperazine-1-carboxylate hydrochloride

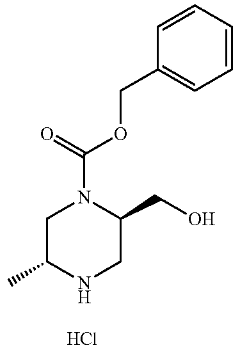 [SMILES: C[C@@H]1CN(C(=O)OCc2ccccc2)[C@@H](CO)CN1 ; Cl]

To a mixture of 1-benzyl 4-(tert-butyl) (2R,5R)-2-(hydroxymethyl)-5-methylpiperazine-1,4-dicarboxylate (364 mg, 1.0 mmol, AstaTech C92269) in THF (5 mL) was added a 4 molar solution of HCl in 1,4-dioxane (1.25 mL, 5 mmol) and the reaction mixture was purged with $N_2$ and stirred at 60° C. for 2 h. After cooling to rt, the reaction mixture was concentrated in vacuo. The crude material obtained was used directly without further purification. LC-MS calculated for $C_{14}H_{21}N_2O_3$ $(M+H)^+$: m/z=265.2. found 265.1.

Step 2: Benzyl (2R,5R)-4-(bis(4-fluorophenyl)methyl)-2-(hydroxymethyl)-5-methylpiperazine-1-carboxylate

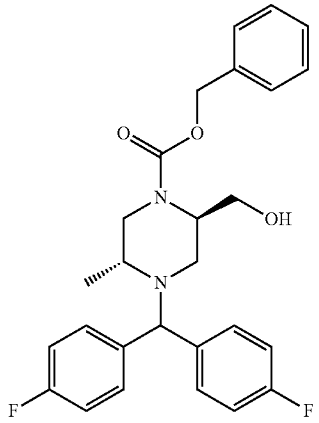 [SMILES: C[C@@H]1CN(C(=O)OCc2ccccc2)[C@@H](CO)CN1C(c1ccc(F)cc1)c1ccc(F)cc1]

A mixture of benzyl (2R,5R)-2-(hydroxymethyl)-5-methylpiperazine-1-carboxylate hydrochloride (Step 1), 4,4'-(chloromethylene)bis(fluorobenzene) (239 mg, 1.0 mmol, Combi-Blocks QA-4728) and N-ethyl-N-isopropylpropan-2-amine (0.52 mL, 3.0 mmol) in $CH_3CN$ (5 mL) was stirred at 85° C. overnight. After cooling to rt, the reaction mixture was concentrated in vacuo and the crude residue was purified using flash column chromatography ($SiO_2$, EtOAc/hexanes). LC-MS calculated for $C_{27}H_{29}F_2N_2O_3$ $(M+H)^+$: m/z=467.2. found 467.2.

Step 3: ((2R,5R)-4-(Bis(4-fluorophenyl)methyl)-5-methylpiperazin-2-yl)methanol

To a mixture of benzyl (2R,5R)-4-(bis(4-fluorophenyl)methyl)-2-(hydroxymethyl)-5-methylpiperazine-1-carboxylate (Step 2) in MeOH (5 mL) was added Pd/C (10 wt %, 106 mg, 0.1 mmol) and the reaction mixture was equipped with a balloon of $H_2$ and stirred at ambient temperature overnight. The mixture was filtered over a pad of celite and the filter cake washed with MeOH. The filtrate was concentrated in vacuo, and the crude material obtained was used directly without further purification. LC-MS calculated for $C_{19}H_{23}F_2N_2O$ $(M+H)^+$: m/z=333.2. found 333.2.

Intermediate 14: Methyl 4-((2R,5R)-4-(bis(4-fluorophenyl)methyl)-2-(hydroxymethyl)-5-methylpiperazin-1-yl)-6-bromo-1-methyl-2-oxo-1,2-dihydro-1,5-naphthyridine-3-carboxylate

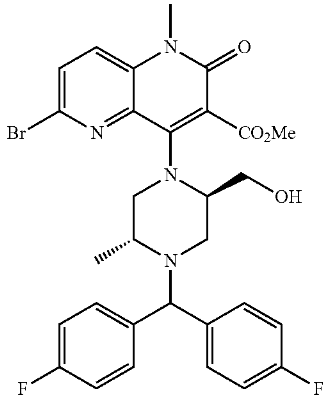 [SMILES: COC(=O)c1c(N2C[C@@H](C)N(C(c3ccc(F)cc3)c3ccc(F)cc3)C[C@@H]2CO)c2nc(Br)ccc2n(C)c1=O]

The title compound was prepared according to the procedures described in Intermediate 6, Steps 1-5 with ((2R,5R)-4-(bis(4-fluorophenyl)methyl)-5-methylpiperazin-2-yl)methanol (Intermediate 13) replacing (R)-(4-(bis(4-fluorophenyl)methyl)piperazin-2-yl)methanol hydrochloride in Step 5. LC-MS calculated for $C_{30}H_{30}BrF_2N_4O_4$ $(M+H)^+$: m/z=627.1. found 627.1.

Intermediate 15: (9aR,12R)-11-(Bis(4-fluorophenyl)methyl)-2-bromo-5,12-dimethyl-9,9a,10,11,12,13-hexahydro-6H-pyrazino[2',1':3,4][1,4]oxazepino[6,5-c][1,5]naphthyridine-6,7(5H)-dione

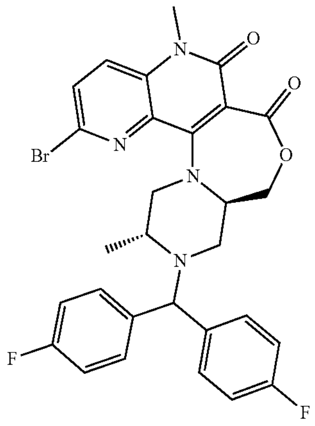 [SMILES: C[C@@H]1CN2c3c(c(=O)n(C)c4ccc(Br)nc34)C(=O)OC[C@H]2CN1C(c1ccc(F)cc1)c1ccc(F)cc1]

The title compound was prepared according to the procedures described in Intermediate 12, with methyl 4-((2R, 5R)-4-(bis(4-fluorophenyl)methyl)-2-(hydroxymethyl)-5-methylpiperazin-1-yl)-6-bromo-1-methyl-2-oxo-1,2-dihydro-1,5-naphthyridine-3-carboxylate (Intermediate 14) replacing methyl (S)-4-(4-(bis(4-fluorophenyl)methyl)-2-(hydroxymethyl)piperazin-1-yl)-6-bromo-1-methyl-2-oxo-1,2-dihydro-1,5-naphthyridine-3-carboxylate. LC-MS calculated for $C_{29}H_{26}BrF_2N_4O_3$ $(M+H)^+$: m/z=595.1. found 595.1.

Intermediate 16: Methyl (R)-4-(4-(bis(4-fluorophenyl)methyl)-2-(hydroxymethyl)piperazin-1-yl)-6-bromo-1-methyl-2-oxo-1,2-dihydroquinoline-3-carboxylate

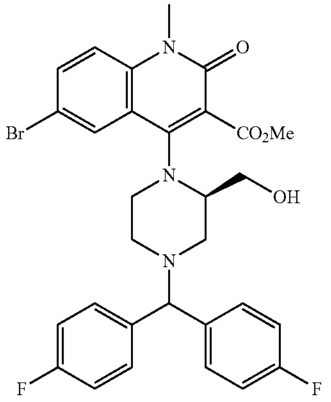 [SMILES: COC(=O)c1c(N2CCN(C(c3ccc(F)cc3)c3ccc(F)cc3)C[C@@H]2CO)c2cc(Br)ccc2n(C)c1=O]

The title compound was prepared according to the procedures described in Intermediate 6, Steps 1-5 with methyl 2-amino-5-bromobenzoate (Aldrich 528811) replacing methyl 3-amino-6-bromopicolinate in Step 1. LC-MS calculated for $C_{30}H_{29}BrF_2N_3O_4$ $(M+H)^+$: m/z=612.1. found 612.1.

Intermediate 17: (R)-3-(Bis(4-fluorophenyl)methyl)-12-bromo-9-methyl-1,2,3,4,4a,5-hexahydro-7H-pyrazino[2',1':3,4][1,4]oxazepino[6,5-c]quinoline-7,8(9H)-dione

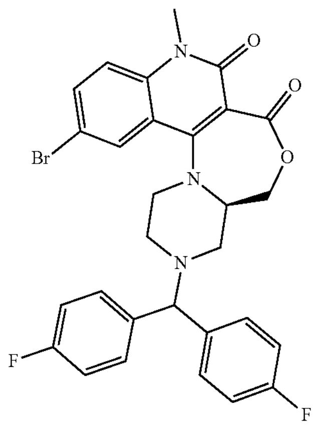 [SMILES: Cn1c(=O)c2c(c3cc(Br)ccc31)N1CCN(C(c3ccc(F)cc3)c3ccc(F)cc3)C[C@@H]1COC2=O]

The title compound was prepared according to the procedures described in Intermediate 12, with methyl (R)-4-(4-(bis(4-fluorophenyl)methyl)-2-(hydroxymethyl)piperazin-1-yl)-6-bromo-1-methyl-2-oxo-1,2-dihydroquinoline-3-carboxylate (Intermediate 16) replacing methyl (S)-4-(4-(bis(4-fluorophenyl)methyl)-2-(hydroxymethyl)piperazin-1-yl)-6-bromo-1-methyl-2-oxo-1,2-dihydro-1,5-naphthyridine-3-carboxylate. LC-MS calculated for $C_{29}H_{25}BrF_2N_3O_3$ $(M+H)^+$: m/z=580.1. found 580.1.

Intermediate 18: Methyl 5-bromo-3-(3-methoxy-3-oxopropanamido)picolinate

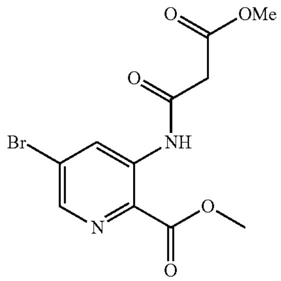 [SMILES: COC(=O)CC(=O)Nc1cc(Br)cnc1C(=O)OC]

The title compound was prepared according to the procedures described in Intermediate 7, with methyl 3-amino-5-bromopicolinate (Combi-Blocks ST-6151) replacing methyl 3-amino-6-bromopyrazine-2-carboxylate. LC-MS calculated for $C_{11}H_{12}BrN_2O_5$ $(M+H)^+$: m/z=331.0. found 331.0.

Intermediate 19: Methyl (R)-4-(4-(bis(4-fluorophenyl)methyl)-2-(hydroxymethyl)piperazin-1-yl)-7-bromo-1-methyl-2-oxo-1,2-dihydro-1,5-naphthyridine-3-carboxylate

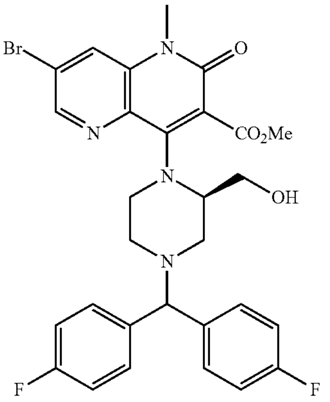 [SMILES: COC(=O)c1c(N2CCN(C(c3ccc(F)cc3)c3ccc(F)cc3)C[C@@H]2CO)c2ncc(Br)cc2n(C)c1=O]

The title compound was prepared according to the procedures described in Intermediate 6, Steps 2-5 with methyl 5-bromo-3-(3-methoxy-3-oxopropanamido)picolinate (Intermediate 18) replacing methyl 6-bromo-3-(3-methoxy-3-oxopropanamido)picolinate in Step 2. LC-MS calculated for $C_{29}H_{28}BrF_2N_4O_4$ $(M+H)^+$: m/z=613.1. found 613.1.

Intermediate 20: (R)-11-(bis(4-fluorophenyl)methyl)-3-bromo-5-methyl-9,9a,10,11,12,13-hexahydro-6H-pyrazino[2',1':3,4][1,4]oxazepino[6,5-c][1,5]naphthyridine-6,7(5H)-dione

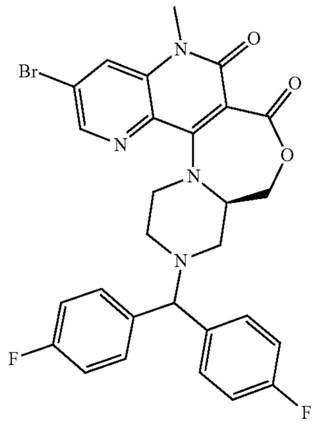 [SMILES: Cn1c(=O)c2c(c3ncc(Br)cc31)N1CCN(C(c3ccc(F)cc3)c3ccc(F)cc3)C[C@@H]1COC2=O]

The title compound was prepared according to the procedures described in Intermediate 12, with methyl (R)-4-(4-(bis(4-fluorophenyl)methyl)-2-(hydroxymethyl)piperazin-1-yl)-7-bromo-1-methyl-2-oxo-1,2-dihydro-1,5-naphthyridine-3-carboxylate (Intermediate 19) replacing methyl (S)-4-(4-(bis(4-fluorophenyl)methyl)-2-(hydroxymethyl)piperazin-1-yl)-6-bromo-1-methyl-2-oxo-1,2-dihydro-1,5-naphthyridine-3-carboxylate. LC-MS calculated for $C_{28}H_{24}BrF_2N_4O_3$ $(M+H)^+$: m/z=581.1. found 581.0.

Example 1. 11-(Bis(4-fluorophenyl)methyl)-5,7-dimethyl-6,8-dioxo-5,6,7,8,9,9a,10,11,12,13-decahydropyrazino[1',2': 4,5][1,4]diazepino[2,3-c][1,5]naphthyridine-2-carbonitrile

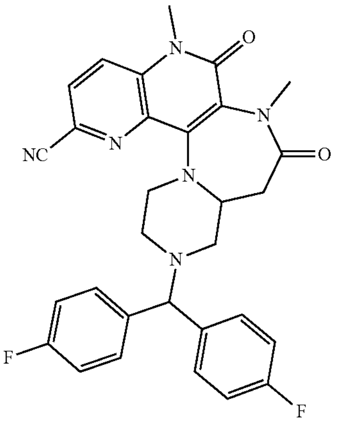 [SMILES: CN1C(=O)CC2CN(C(c3ccc(F)cc3)c3ccc(F)cc3)CCN2c2c1c(=O)n(C)c1ccc(C#N)nc21]

Step 1: tert-Butyl 4-(3-amino-6-cyano-1-methyl-2-oxo-1,2-dihydro-1,5-naphthyridin-4-yl)-3-(2-methoxy-2-oxoethyl)piperazine-1-carboxylate

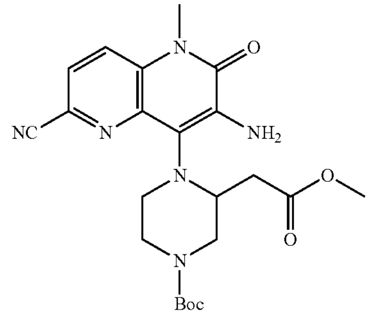 [SMILES: COC(=O)CC1CN(C(=O)OC(C)(C)C)CCN1c1c(N)c(=O)n(C)c2ccc(C#N)nc12]

A mixture of tert-butyl 4-(6-cyano-1-methyl-3-nitro-2-oxo-1,2-dihydro-1,5-naphthyridin-4-yl)-3-(2-methoxy-2-oxoethyl)piperazine-1-carboxylate (Intermediate 3, 19.5 mg, 0.040 mmol), iron (11.2 mg, 0.20 mmol), and ammonium chloride (21.4 mg, 0.40 mmol) in a 1:1:1 mixture of THF/MeOH/$H_2O$ (0.2 mL) was stirred at 60° C. for 1 h. After cooling to rt, the mixture was diluted with sat. aq. NaCl and extracted with $CH_2Cl_2$. The combined organic phases were dried over $MgSO_4$ and concentrated. The crude material obtained was used directly without further purification. LC-MS calculated for $C_{22}H_{29}N_6O_5$ $(M+H)^+$: m/z=457.2. found 457.2.

Step 2: tert-Butyl 2-cyano-5,7-dimethyl-6,8-dioxo-5,7,8,9,9a,10,12,13-octahydropyrazino[1',2':4,5][1,4]diazepino[2,3-c][1,5]naphthyridine-11(6H)-carboxylate

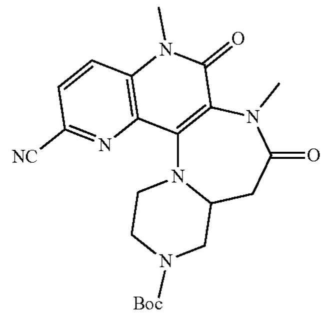 [SMILES: CN1C(=O)CC2CN(C(=O)OC(C)(C)C)CCN2c2c1c(=O)n(C)c1ccc(C#N)nc21]

To a mixture of tert-butyl 4-(3-amino-6-cyano-1-methyl-2-oxo-1,2-dihydro-1,5-naphthyridin-4-yl)-3-(2-methoxy-2-oxoethyl)piperazine-1-carboxylate (Step 1) in DMF (0.2 mL) was added sodium hydride (60% dispersion in mineral oil, 4.8 mg, 0.12 mmol) and the mixture was stirred at 60° C. for 2 h. After cooling to rt, additional sodium hydride (60% dispersion in mineral oil, 4.8 mg, 0.12 mmol) was added followed by methyl iodide (17.1 mg, 0.12 mmol) and the mixture was stirred at rt for 2 h. The reaction mixture was quenched via the dropwise addition of sat. aq. $NH_4Cl$ and extracted with $CH_2Cl_2$. The combined organic phases were dried over $MgSO_4$ and concentrated. The crude material obtained was used directly without further purification. LC-MS calculated for $C_{22}H_{26}N_6O_4Na$ $(M+Na)^+$: m/z=461.2. found 461.2.

Step 3: 5,7-Dimethyl-6,8-dioxo-5,6,7,8,9,9a,10,11,12,13-decahydropyrazino[1',2':4,5][1,4]diazepino[2,3-c][1,5]naphthyridine-2-carbonitrile hydrochloride

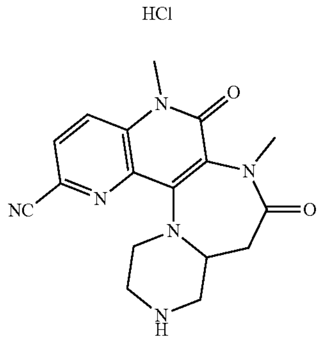 [SMILES: Cl ; CN1C(=O)CC2CNCCN2c2c1c(=O)n(C)c1ccc(C#N)nc21]

To a mixture of tert-butyl 2-cyano-5,7-dimethyl-6,8-dioxo-5,7,8,9,9a,10,12,13-octahydropyrazino[1',2':4,5][1,4]diazepino[2,3-c][1,5]naphthyridine-11(6H)-carboxylate (Step 2) in THF (0.2 mL) was added a 4 molar solution of HCl in 1,4-dioxane (0.1 mL, 0.4 mmol) and the reaction mixture was purged with $N_2$ and stirred at 60° C. for 2 h. After cooling to rt, the reaction mixture was concentrated in vacuo and the crude material obtained was used directly without further purification. LC-MS calculated for $C_{17}H_{19}N_6O_2$ $(M+H)^+$: m/z=339.2. found 339.1.

Step 4: (8aR,11R)-10-(Bis(4-fluorophenyl)methyl)-5,11-dimethyl-6,8-dioxo-5,7,8,8a,9,10,11,12-octahydro-6H-pyrazino[1',2':4,5]pyrazino[2,3-c][1,5]naphthyridine-2-carbonitrile A mixture of 5,7-dimethyl-6,8-dioxo-5,6,7,8,9,9a,10,11,12,13-decahydropyrazino[1',2':4,5][1,4]diazepino[2,3-c][1,5]naphthyridine-2-carbonitrile hydrochloride (Step 3), 4,4'-(chloromethylene)bis(fluorobenzene) (14.35 mg, 0.060 mmol), and N-ethyl-N-isopropylpropan-2-amine (16 mg, 0.12 mmol) in $CH_3CN$ (0.2 mL) was stirred at 85° C. overnight. After cooling to rt, the reaction mixture was diluted with acetonitrile, water, and several drops of TFA, and the mixture was filtered and purified by preparative HPLC (Sunfire C18 column, eluting with a gradient of acetonitrile/water containing 0.1% TFA, at flow rate of 60 mL/min) to afford the desired product as its TFA salt. LC-MS calculated for $C_{30}H_{27}F_2N_6O_2$ $(M+H)^+$: m/z=541.2. found 541.1.

Example 2. 11-(Bis(4-fluorophenyl)methyl)-5,7-dimethyl-6,8-dioxo-5,6,7,8,9,9a,10,11,12,13-decahydropyrazino[1',2': 4,5][1,4]diazepino[2,3-c][1,5]naphthyridine-2-carbonitrile

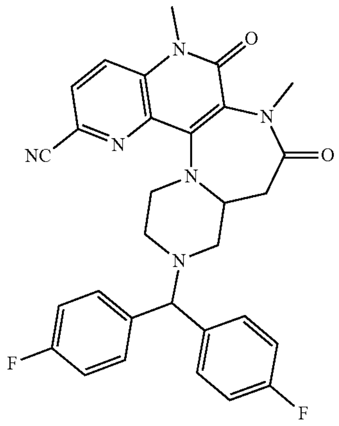 [SMILES: CN1C(=O)CC2CN(C(c3ccc(F)cc3)c3ccc(F)cc3)CCN2c2c1c(=O)n(C)c1ccc(C#N)nc21]

The title compound was prepared according to the procedures described in Example 1, with tert-butyl 4-(6-cyano-1-methyl-3-nitro-2-oxo-1,2-dihydro-1,5-naphthyridin-4-yl)-3-(2-m ethoxy-2-oxoethyl)piperazine-1-carboxylate (Intermediate 4) replacing Intermediate 3 in Step 1. LC-MS calculated for $C_{30}H_{27}F_2N_6O_2$ $(M+H)^+$: m/z=541.2. found 541.1.

Example 3: (R)-11-(Bis(4-fluorophenyl)methyl)-5-methyl-6,7-dioxo-5,7,9,9a,10,11,12,13-octahydro-6H-pyrazino[2',1':3,4][1,4]oxazepino[6,5-c][1,5]naphthyridine-2-carbonitrile

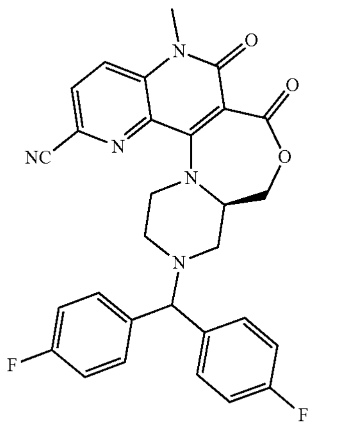 [SMILES: Cn1c(=O)c2c(c3nc(C#N)ccc31)N1CCN(C(c3ccc(F)cc3)c3ccc(F)cc3)C[C@@H]1COC2=O]

To a mixture of (R)-11-(bis(4-fluorophenyl)methyl)-2-bromo-5-methyl-9,9a,10,11,12,13-hexahydro-6H-pyrazino[2',1':3,4][1,4]oxazepino[6,5-c][1,5]naphthyridine-6,7(5H)-dione (Intermediate 6, 23.2 mg, 0.040 mmol) in DMF (0.3 mL) was added copper(I) iodide (8 mg, 0.04 mmol), 1-methyl-1H-imidazole (3 mg, 0.040 mmol), and potassium ferrocyanide (14 mg, 0.04 mmol) and the reaction mixture was stirred at 130° C. for 4 h. After cooling to rt, the mixture was diluted with acetonitrile, water, and several drops of TFA. The resulting mixture was filtered and purified by preparative HPLC (Sunfire C18 column, eluting with a gradient of acetonitrile/water containing 0.1% TFA, at flow rate of 60 mL/min) to afford the desired product as its TFA salt. LC-MS calculated for $C_{29}H_{24}F_2N_5O_2$ $(M+H)^+$: m/z=528.2. found 528.2.

Example 4: (R)-2-(11-(Bis(4-fluorophenyl)methyl)-5-methyl-6,7-dioxo-5,7,9,9a,10,11,12,13-octahydro-6H-pyrazino[2',1':3,4][1,4]oxazepino[6,5-c][1,5]naphthyridin-2-yl)acetonitrile

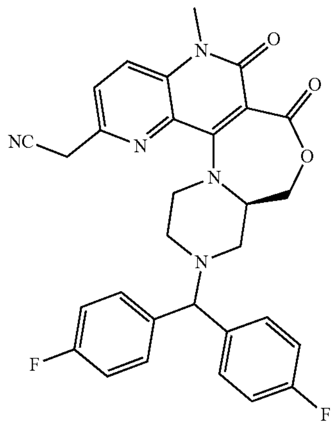 [SMILES: Cn1c(=O)c2c(c3nc(CC#N)ccc31)N1CCN(C(c3ccc(F)cc3)c3ccc(F)cc3)C[C@@H]1COC2=O]

To a mixture of (R)-11-(bis(4-fluorophenyl)methyl)-2-bromo-5-methyl-9,9a,10,11,12,13-hexahydro-6H-pyrazino[2',1':3,4][1,4]oxazepino[6,5-c][1,5]naphthyridine-6,7(5H)-dione (Intermediate 6, 14.5 mg, 0.025 mmol), 4-(4,4,5,5-tetramethyl-1,3,2-dioxaborolan-2-yl)isoxazole (14.76 mg, 0.076 mmol) and potassium fluoride (4.4 mg, 0.076 mmol) in DMSO (0.3 mL) was added [1,1'-bis(diphenylphosphino)ferrocene]dichloropalladium(II), complex with dichloromethane (2.1 mg, 2.6 μmol) and water (1.4 mg, 0.08 mmol) and the reaction mixture was flushed with $N_2$ and stirred at 130° C. overnight. After cooling to rt, the mixture was diluted with acetonitrile, water, and several drops of TFA. The resulting mixture was filtered and purified by preparative HPLC (Sunfire C18 column, eluting with a gradient of acetonitrile/water containing 0.1% TFA, at flow rate of 60 mL/min) to afford the desired product as its TFA salt. LC-MS calculated for $C_{30}H_{26}F_2N_5O_3$ $(M+H)^+$: m/z=542.2. found 542.3.

Example 5: (R)-2-(11-(Bis(4-fluorophenyl)methyl)-5-methyl-6,7-dioxo-5,7,9,9a,10,11,12,13-octahydro-6H-pyrazino[2,1-c]pyrazino[2',3': 5,6]pyrido[4,3-e][1,4]oxazepin-2-yl)acetonitrile

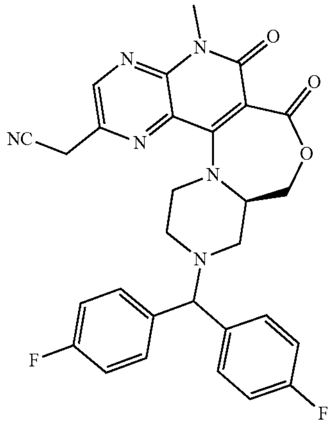 [SMILES: Cn1c(=O)c2c(c3nc(CC#N)cnc31)N1CCN(C(c3ccc(F)cc3)c3ccc(F)cc3)C[C@@H]1COC2=O]

The title compound was prepared according to the procedures described in Example 4, with Intermediate 9 replacing (R)-11-(bis(4-fluorophenyl)methyl)-2-bromo-5-methyl-9,9a,10,11,12,13-octahydro-6H-pyrazino[2',1':3,4][1,4]oxazepino[6,5-c][1,5]naphthyridine-6,7(5H)-dione. LC-MS calculated for $C_{29}H_{25}F_2N_6O_3$ $(M+H)^+$: m/z=543.2. found 543.3.

Example 6: (S)-11-(Bis(4-fluorophenyl)methyl)-5-methyl-6,7-dioxo-5,7,9,9a,10,11,12,13-octahydro-6H-pyrazino[2',1':3,4][1,4]oxazepino[6,5-c][1,5]naphthyridine-2-carbonitrile

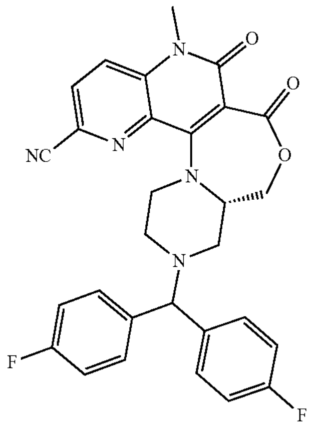 [SMILES: Cn1c(=O)c2c(c3nc(C#N)ccc31)N1CCN(C(c3ccc(F)cc3)c3ccc(F)cc3)C[C@H]1COC2=O]

The title compound was prepared according to the procedures described in Example 3, with (S)-11-(bis(4-fluorophenyl)methyl)-2-bromo-5-methyl-9,9a,10,11,12,13-hexahydro-6H-pyrazino[2',1':3,4][1,4]oxazepino[6,5-c][1,5]naphthyridine-6,7(5H)-dione (Intermediate 12) replacing (R)-11-(bis(4-fluorophenyl)methyl)-2-bromo-5-methyl-9,9a,10,11,12,13-hexahydro-6H-pyrazino[2',1':3,4][1,4]oxazepino[6,5-c][1,5]naphthyridine-6,7(5H)-dione. LC-MS calculated for $C_{29}H_{24}F_2N_5O_3$ $(M+H)^+$: m/z=528.2. found 528.2.

Example 7: (9aR,12R)-11-(Bis(4-fluorophenyl)methyl)-5,12-dimethyl-6,7-dioxo-5,7,9,9a,10,11,12,13-octahydro-6H-pyrazino[2',1':3,4][1,4]oxazepino[6,5-c][1,5]naphthyridine-2-carbonitrile

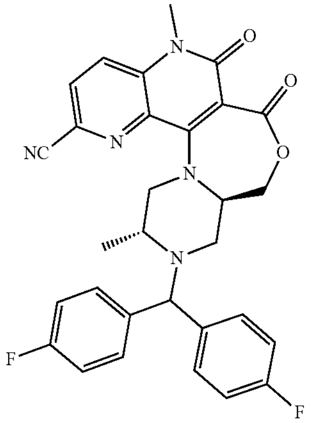 [SMILES: C[C@@H]1CN2c3c(c(=O)n(C)c4ccc(C#N)nc34)C(=O)OC[C@H]2CN1C(c1ccc(F)cc1)c1ccc(F)cc1]

The title compound was prepared according to the procedures described in Example 3, with (9aR,12R)-11-(bis(4-fluorophenyl)methyl)-2-bromo-5,12-dimethyl-9,9a,10,11,12,13-hexahydro-6H-pyrazino[2',1':3,4][1,4]oxazepino[6,5-c][1,5]naphthyridine-6,7(51-1)-dione (Intermediate 15) replacing (R)-11-(bis(4-fluorophenyl)methyl)-2-bromo-5-methyl-9,9a,10,11,12,13-hexahydro-6H-pyrazino[2',1':3,4][1,4]oxazepino[6,5-c][1,5]naphthyridine-6,7(5H)-dione. LC-MS calculated for $C_{30}H_{26}F_2N_5O_3$ $(M+H)^+$: m/z=542.2. found 542.2.

Example 8: (R)-2-(3-(Bis(4-fluorophenyl)methyl)-9-methyl-7,8-dioxo-1,2,3,4,4a,5,8,9-octahydro-7H-pyrazino[2',1':3,4][1,4]oxazepino[6,5-c]quinolin-12-yl)acetonitrile

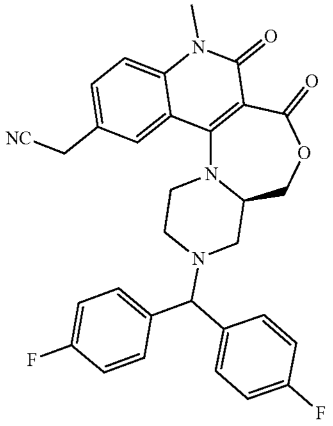 [SMILES: Cn1c(=O)c2c(c3cc(CC#N)ccc31)N1CCN(C(c3ccc(F)cc3)c3ccc(F)cc3)C[C@@H]1COC2=O]

The title compound was prepared according to the procedures described in Example 4, with (R)-3-(bis(4-fluorophenyl)methyl)-12-bromo-9-methyl-1,2,3,4,4a,5-hexahydro-7H-pyrazino[2',1':3,4][1,4]oxazepino[6,5-c]quinoline-7,8(9H)-dione (Intermediate 17) replacing (R)-11-(bis(4-fluorophenyl)methyl)-2-bromo-5-methyl-9,9a,10,11,12,13-hexahydro-6H-pyrazino[2',1':3,4][1,4]oxazepino[6,5-c][1,5]naphthyridine-6,7(5H)-dione. LC-MS calculated for $C_{31}H_{27}F_2N_4O_3$ $(M+H)^+$: m/z=541.2. found 541.3.

Example 9: (R)-11-(Bis(4-fluorophenyl)methyl)-5-methyl-6,7-dioxo-5,7,9,9a,10,11,12,13-octahydro-6H-pyrazino[2',1':3,4][1,4]oxazepino[6,5-c][1,5]naphthyridine-3-carbonitrile

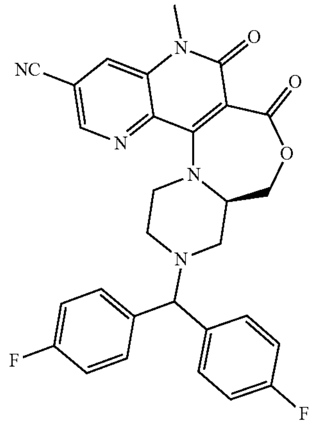 [SMILES: Cn1c(=O)c2c(c3ncc(C#N)cc31)N1CCN(C(c3ccc(F)cc3)c3ccc(F)cc3)C[C@@H]1COC2=O]

To a mixture of (R)-11-(bis(4-fluorophenyl)methyl)-3-bromo-5-methyl-9,9a,10,11,12,13-hexahydro-6H-pyrazino[2',1':3,4][1,4]oxazepino[6,5-c][1,5]naphthyridine-6,7(5H)-dione (Intermediate 20, 23.2 mg, 0.040 mmol) in N-methyl-2-pyrrolidone (0.3 mL) was added [1,1'-bis(diphenylphosphino)ferrocene]dichloropalladium(II), complex with dichloromethane (4.2 mg, 5.2 Zn (0.6 mg, 0.01 mmol), and $Zn(CN)_2$ (9.4 mg, 0.08 mmol) and the reaction mixture was stirred at 80° C. for 5 h. After cooling to rt, the mixture was diluted with acetonitrile, water, and several drops of TFA. The resulting mixture was filtered and purified by preparative HPLC (Sunfire C18 column, eluting with a gradient of acetonitrile/water containing 0.1% TFA, at flow rate of 60 mL/min) to afford the desired product as its TFA salt. LC-MS calculated for $C_{29}H_{24}F_2N_5O_3$ $(M+H)^+$: m/z=528.2. found 528.3.

Example 10: (R)-2-(11-(Bis(4-fluorophenyl)methyl)-5-methyl-6,7-dioxo-5,7,9,9a,10,11,12,13-octahydro-6H-pyrazino[2',1':3,4][1,4]oxazepino[6,5-c][1,5]naphthyridin-3-yl)acetonitrile

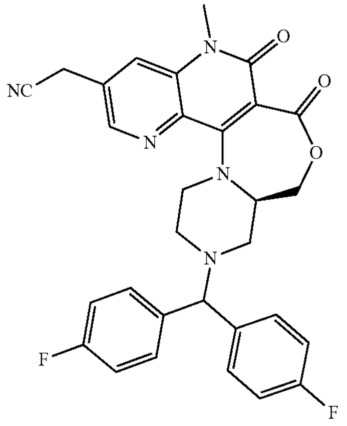 [SMILES: Cn1c(=O)c2c(c3ncc(CC#N)cc31)N1CCN(C(c3ccc(F)cc3)c3ccc(F)cc3)C[C@@H]1COC2=O]

The title compound was prepared according to the procedures described in Example 4, with (R)-11-(bis(4-fluorophenyl)methyl)-3-bromo-5-methyl-9,9a,10,11,12,13-hexahydro-6H-pyrazino[2',1':3,4][1,4]oxazepino[6,5-c][1,5]naphthyridine-6,7(5H)-dione (Intermediate 20) replacing (R)-11-(bis(4-fluorophenyl)methyl)-2-bromo-5-methyl-9,9a,10,11,12,13-hexahydro-6H-pyrazino[2',1':3,4][1,4]oxazepino[6,5-c][1,5]naphthyridine-6,7(5H)-dione. LC-MS calculated for $C_{30}H_{26}F_2N_5O_3$ $(M+H)^+$: m/z=542.2. found 542.3.

Example A. In Vitro DGKα and DGKζ Inhibition Assays

The DGKα and DGKζ biochemical reactions were performed using His-tagged human recombinant enzymes (Signal Chem, DGKα, #D21-10BH; DGKζ, #D30-10H)) and DLG (Dilauroyl-sn-glycerol) lipid substrate (Signal Chem, #D430-59). ADP-Glo assay was performed using ADP-Glo™ kinase Assay kit (Promega, #V9104). The reactions were carried out in assay buffer containing 40 mM Tris, pH 7.5, 0.1% CHAPS, 0.1% Prionex, 40 mM NaCl, 5 mM $MgCl_2$, 1 mM $CaCl_2$, and 1 mM DTT. DGKα reactions contained 0.1 nM DGKα, 50 μM ATP, and 20 μM DLG. And DGKζ reactions contained 0.4 nM DGKζ, 30 μM ATP, and 20 μM DLG.

For compound inhibition studies, 40 nL test compound in DMSO was added to wells of white polystyrene plates in 384-well (Greiner, #784075) or 1536-well format (Greiner, #782075). Compounds were added with top concentration of 2 mM with 11 point, 3-fold dilution series. Enzyme solution (contains 2×DGK enzyme concentration in 1× assay buffer) was added to the plate in 2 μL/well volume, followed by 2 μL/well of substrate solution (contains 2× concentration of ATP and DLG substrate in 1× assay buffer). Plates were then centrifuged for 1 min at 1200 RPM and sealed or lidded. For 4 μL reaction volume, test compounds were therefore diluted 100× to final top concentration of 20 μM. After 90 minute incubation, reactions were quenched by addition of 2 μL/well Promega ADP-Glo Reagent, followed by centrifugation and lidding. After 60 min incubation, 2 μL/well Promega Kinase Detection Reagent was added, plates centrifuged, and incubated for 30 min. Plates were then read using Luminescence method on BMG PHERAstar FSX plate reader. Percent inhibition was calculated and $IC_{50}$s were determined using 4-parameter fit in Genedata Screener. Labcyte Echo acoustic dispenser was used for compound addition, and Formulatrix Tempest liquid handler was used for all reagent dispenses.

The compounds of the disclosure were tested in one or more of the assays described in Example A, and the resulting data are shown in Table A.

TABLE A

| Example | DGKα $IC_{50}$ (nM) | DGKζ $IC_{50}$ (nM) |
|---|---|---|
| 1 | + | +++ |
| 2 | ++ | + |
| 3 | + | + |
| 4 | + | + |
| 5 | ++ | ++ |
| 6 | + | + |

TABLE A-continued

| Example | DGKα $IC_{50}$ (nM) | DGKζ $IC_{50}$ (nM) |
|---|---|---|
| 7 | + | +++ |
| 8 | + | ++ |
| 9 | + | ++++ |
| 10 | + | ++++ |

+ refers to $IC_{50}$ of ≤40 nM
++ refers to $IC_{50}$ of >40 nM to ≤200 nM
+++ refers to $IC_{50}$ of >200 nM to ≤2000 nM
++++ refers to $IC_{50}$ of >2000 nM Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A compound of Formula I:

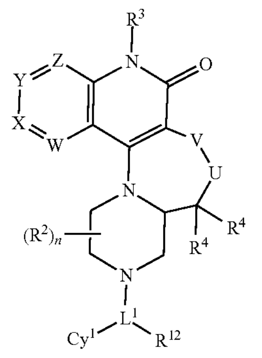

I or a pharmaceutically acceptable salt thereof, wherein:

$\overline{---}$ is a single or double bond;

U is C(O) and V is $NR^6$; or

U is $NR^5$ or O and V is C(O);

W is $CR^7$, C(O), N, or $NR^7$;

X is $CR^8$, C(O), N, or $NR^8$;

Y is $CR^9$ or N;

Z is $CR^{10}$ or N;

wherein:

(i) when W is C(O) then X is $NR^8$;

(ii) when X is C(O) then W is $NR^7$; and (iii) no more than 2 of W, X, Y, and Z can be N or a substituted N;

n is 0, 1, or 2;

each $R^2$ is independently selected from halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, CN, $NO_2$, $OR^{a2}$, $NHOR^{a2}$, $C(O)R^{b2}$, $C(O)NR^{c2}R^{d2}$, $C(O)NR^{c2}(OR^{a2})$, $C(O)OR^{a2}$, $OC(O)R^{b2}$, $OC(O)NR^{c2}R^{d2}$, $NR^{c2}R^{d2}$, $NR^{c2}NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)NR^{c2}R^{d2}$, $NR^{c2}S(O)_2R^{b2}$, $NR^{c2}S(O)(=NR^{e2})R^{b2}$, $NR^{c2}S(O)_2NR^{c2}R^{d2}$, $S(O)R^{b2}$, $S(O)NR^{c2}R^{d2}$, $S(O)_2R^{b2}$, $S(O)_2NR^{c2}R^{d2}$, $OS(O)(=NR^{e2})R^{b2}$, and $OS(O)_2R^{b2}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, and 4-7 membered heterocycloalkyl of $R^2$ are each optionally substituted with 1, 2, 3, or 4 independently selected $R^M$ substituents;

each $R^{a2}$, $R^{c2}$, and $R^{d2}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

or, any $R^{c2}$ and $R^{d2}$ attached to the same N atom, together with the N atom to which they are attached, form a 5-6 membered heteroaryl or a 4-7 membered heterocycloalkyl group;

each $R^{b2}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

each $R^{e2}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

$R^3$ is selected from H, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, and 4-7 membered heterocycloalkyl, wherein the $C_{1-6}$ alkyl, $C_{2-6}$ alkenyl, $C_{2-6}$ alkynyl, phenyl, $C_{3-7}$ cycloalkyl, 5-6 membered heteroaryl, and 4-7 membered heterocycloalkyl of $R^3$ are each optionally substituted with 1, 2, 3, or 4 independently selected $R^M$ substituents;

each $R^4$ is independently selected from H, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, wherein the $C_{1-6}$ alkyl, $C_{2-6}$ alkenyl, $C_{2-6}$ alkynyl, phenyl, $C_{3-7}$ cycloalkyl, 5-6 membered heteroaryl, and 4-7 membered heterocycloalkyl of $R^4$ are each optionally substituted with 1, 2, 3, or 4 independently selected $R^M$ substituents;

or, two $R^4$ groups attached to the same carbon atom, together with the carbon atom to which they are attached, form a $C_{3-6}$ cycloalkyl, which is optionally substituted with 1, 2, 3, or 4 independently selected $R^M$ substituents;

$R^5$ is selected from H, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, wherein the $C_{1-6}$ alkyl, $C_{2-6}$ alkenyl, $C_{2-6}$ alkynyl, phenyl, $C_{3-7}$ cycloalkyl, 5-6 membered heteroaryl, and 4-7 membered heterocycloalkyl of $R^5$ are each optionally substituted with 1, 2, 3, or 4 independently selected $R^M$ substituents;

$R^6$ is selected from H, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, wherein the $C_{1-6}$ alkyl, $C_{2-6}$ alkenyl, $C_{2-6}$ alkynyl, phenyl, $C_{3-7}$ cycloalkyl, 5-6 membered heteroaryl, and 4-7 membered heterocycloalkyl of $R^6$ are each optionally substituted with 1, 2, 3, or 4 independently selected $R^M$ substituents;

$R^7$ is selected from H, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a7}$, $SR^{a7}$, $NHOR^{a7}$, $C(O)R^{b7}$, $C(O)NR^{c7}R^{d7}$, $C(O)NR^{c7}(OR^{a7})$, $C(O)OR^{a7}$, $OC(O)R^{b7}$, $OC(O)NR^{c7}R^{d7}$, $NR^{c7}R^{d7}$, $NR^{c7}NR^{c7}R^{d7}$, $NR^{c7}C(O)R^{b7}$, $NR^{c7}C(O)OR^{a7}$, $NR^{c7}C(O)NR^{c7}R^{d7}$, $C(=NR^{e7})R^{b7}$, $C(=NR^{e7})NR^{c7}R^{d7}$, $C(=NOR^{a7})R^{b7}$, $C(=NOR^{a7})OR^{a7}$, $NR^{c7}C(=NR^{e7})NR^{c7}R^{d7}$, $NR^{c7}C(=NR^{e7})R^{b7}$, $NR^{c7}S(O)R^{b7}$, $NR^{c7}S(O)NR^{c7}R^{d7}$, $NR^{c7}S(O)_2R^{b7}$, $NR^{c7}S(O)(=NR^{e7})R^{b7}$, $NR^{c7}S(O)_2NR^{c7}R^{d7}$, $S(O)R^{b7}$, $S(O)NR^{c7}R^{d7}$, $S(O)_2R^{b7}$, $S(O)_2NR^{c7}R^{d7}$, $OS(O)(=NR^{e7})R^{b7}$, and $OS(O)_2R^{b7}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^7$ are each optionally substituted with 1, 2, 3, 4, 5, 6, 7, or 8 independently selected $R^{7A}$ substituents;

each $R^{a7}$, $R^{c7}$, and $R^{d7}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a7}$, $R^{c7}$ and $R^{d7}$ are each optionally substituted with 1, 2, 3, 4, 5, 6, 7, or 8 independently selected $R^{7A}$ substituents;

or, any $R^{c7}$ and $R^{d7}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, 4, 5, 6, 7, or 8 independently selected $R^{7A}$ substituents;

each $R^{b7}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b7}$ are each optionally substituted with 1, 2, 3, 4, 5, 6, 7, or 8 independently selected $R^{7A}$ substituents;

each $R^{e7}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{7A}$ is independently selected from halo, oxo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a71}$, $SR^{a71}$, $NHOR^{a71}$, $C(O)R^{b71}$, $C(O)NR^{c71}R^{d71}$, $C(O)NR^{b71}(OR^{a71})$, $C(O)OR^{a71}$, OC(O)

$R^{b71}$, OC(O)NR$^{c71}$R$^{d71}$, NR$^{c71}$R$^{d71}$, NR$^{c71}$NR$^{c71}$R$^{d71}$ NR$^{c71}$C(O)R$^{b71}$, NR$^{c71}$C(O)OR$^{a71}$, NR$^{c71}$C(O)NR$^{c71}$R$^{d71}$, C(═NR$^{e71}$)R$^{b71}$, C(═NR$^{e71}$)NR$^{c71}$R$^{d71}$, C(═NOR$^{a71}$)R$^{b71}$, C(═NOR$^{a71}$)OR$^{a71}$, NR$^{b71}$C(═NR$^{e71}$)NR$^{c71}$R$^{d71}$, NR$^{c71}$C(═NR$^{e71}$)R$^{b71}$, NR$^{c71}$S(O)R$^{b71}$, NR$^{c71}$S(O)NR$^{c71}$R$^{d71}$, NR$^{c71}$S(O)$_2$R$^{b71}$, NR$^{c71}$S(O)(═NR$^{e71}$)R$^{b71}$, NR$^{c71}$S(O)$_2$NR$^{c71}$R$^{d71}$, S(O)R$^{b71}$, S(O)NR$^{c71}$R$^{d71}$, S(O)$_2$R$^{b71}$, S(O)$_2$NR$^{c71}$R$^{d71}$, OS(O)(═NR$^{e71}$)R$^{b71}$, and OS(O)$_2$R$^{b71}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{7A}$ are each optionally substituted with 1, 2, 3, or 4 independently selected $R^M$ substituents;

each $R^{a71}$, $R^{c71}$, and $R^{d71}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a71}$, $R^{c71}$ and $R^{d71}$ are each optionally substituted with 1, 2, 3, or 4 independently selected $R^M$ substituents;

or, any $R^{c71}$ and $R^{d71}$ attached to the same N atom, together with the N atom to which they are attached, form a 5-6 membered heteroaryl or a 4-7 membered heterocycloalkyl group, wherein the 5-6 membered heteroaryl or 4-7 membered heterocycloalkyl group is optionally substituted with 1, 2, 3, or 4 independently selected $R^M$ substituents;

each $R^{b71}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{b71}$ are each optionally substituted with 1, 2, 3, or 4 independently selected $R^M$ substituents;

each $R^{e71}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

$R^8$ is selected from H, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_1$-6 alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, OR$^{a8}$, SR$^{a8}$, NHOR$^{a8}$, C(O)R$^{b8}$, C(O)NR$^{c8}$R$^{d8}$, C(O)NR$^{c8}$(OR$^{a8}$), C(O)OR$^{a8}$, OC(O)R$^{b8}$, OC(O)NR$^{c8}$R$^{d8}$, NR$^{c8}$R$^{d8}$, NR$^{c8}$NR$^{c8}$R$^{d8}$, NR$^{c8}$C(O)R$^{b8}$, NR$^{c8}$C(O)OR$^{a8}$, NR$^{c8}$C(O)NR$^{c8}$R$^{d8}$, C(═NR$^{e8}$)R$^{b8}$, C(═NR$^{e8}$)NR$^{c8}$R$^{d8}$, C(═NOR$^{a8}$)R$^{b8}$, C(═NOR$^{a8}$)OR$^{a8}$, NR$^{c8}$C(═NR$^{e8}$)NR$^{c8}$R$^{d8}$, NR$^{c8}$C(═NR$^{e8}$)R$^{b8}$, NR$^{c8}$S(O)R$^{b8}$, NR$^{c8}$S(O)NR$^{c8}$R$^{d8}$, NR$^{c8}$S(O)$_2$R$^{b8}$, NR$^{c8}$S(O)(═NR$^{e8}$)R$^{b8}$, NR$^{c8}$S(O)$_2$NR$^{c8}$R$^{d8}$, S(O)R$^{b8}$, S(O)NR$^{c8}$R$^{d8}$, S(O)$_2$R$^{b8}$, S(O)$_2$NR$^{c8}$R$^{d8}$, OS(O)(═NR$^{e8}$)R$^{b8}$, and OS(O)$_2$R$^{b8}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^8$ are each optionally substituted with 1, 2, 3, 4, 5, 6, 7, or 8 independently selected $R^{8A}$ substituents;

each $R^{a8}$, $R^{c8}$, and $R^{d8}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a8}$, $R^{c8}$ and $R^{d8}$ are each optionally substituted with 1, 2, 3, 4, 5, 6, 7, or 8 independently selected $R^{8A}$ substituents;

or, any $R^{c8}$ and $R^{d8}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, 4, 5, 6, 7, or 8 independently selected $R^{8A}$ substituents;

each $R^{b8}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b8}$ are each optionally substituted with 1, 2, 3, 4, 5, 6, 7, or 8 independently selected $R^{8A}$ substituents;

each $R^{e8}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{8A}$ is independently selected from halo, oxo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, OR$^{a81}$, SR$^{a81}$, NHOR$^{a81}$, C(O)R$^{b81}$, C(O)NR$^{c81}$R$^{d81}$, C(O)NR$^{c81}$(OR$^{a81}$), C(O)OR$^{a81}$, OC(O)R$^{b81}$, OC(O)NR$^{c81}$R$^{d81}$, NR$^{c81}$R$^{d81}$, NR$^{c81}$NR$^{c81}$R$^{d81}$, NR$^{c81}$C(O)R$^{b81}$, NR$^{c81}$C(O)OR$^{a81}$, NR$^{c81}$C(O)NR$^{c81}$R$^{d81}$, C(═NR$^{e81}$)R$^{b81}$, C(═NR$^{e81}$)NR$^{c81}$R$^{d81}$, C(═NOR$^{a81}$)R$^{b81}$, C(═NOR$^{a81}$)OR$^{a81}$, NR$^{c81}$C $(=NR^{e81})NR^{c81}R^{d81}$, $NR^{c81}C(=NR^{e81})R^{b81}$, $NR^{c81}S(O)R^{b81}$, $NR^{c81}S(O)NR^{c81}R^{d81}$, $NR^{c81}S(O)_2R^{b81}$, $NR^{c81}S(O)(=NR^{e81})R^{b81}$, $NR^{c81}S(O)_2NR^{c81}R^{d81}$, $S(O)R^{b81}$, $S(O)NR^{c81}R^{d81}$, $S(O)_2R^{b81}$, $S(O)_2NR^{c81}R^{d81}$, $OS(O)(=NR^{e81})R^{b81}$, and $OS(O)_2R^{b81}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{8A}$ are each optionally substituted with 1, 2, 3, or 4 independently selected $R^{M}$ substituents;

each $R^{a81}$, $R^{c81}$, and $R^{d81}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a81}$, $R^{c81}$ and $R^{d81}$ are each optionally substituted with 1, 2, 3, or 4 independently selected $R^{M}$ substituents;

or, any $R^{c81}$ and $R^{d81}$ attached to the same N atom, together with the N atom to which they are attached, form a 5-6 membered heteroaryl or a 4-7 membered heterocycloalkyl group, wherein the 5-6 membered heteroaryl or 4-7 membered heterocycloalkyl group is optionally substituted with 1, 2, 3, or 4 independently selected $R^{M}$ substituents;

each $R^{b81}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{b81}$ are each optionally substituted with 1, 2, 3, or 4 independently selected $R^{M}$ substituents;

each $R^{e81}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

$R^9$ is selected from H, halo, $C_{1-6}$ alkyl, $C_{1-6}$ haloalkyl, $C_{2-6}$ alkenyl, $C_{2-6}$ alkynyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a9}$, $SR^{a9}$, $NHOR^{a9}$, $C(O)R^{b9}$, $C(O)NR^{c9}R^{d9}$, $C(O)NR^{c9}(OR^{a9})$, $C(O)OR^{a9}$, $OC(O)R^{b9}$, $OC(O)NR^{c9}R^{d9}$, $NR^{c99}R^{d99}$, $NR^{c9}NR^{c9}R^{d9}$, $NR^{c9}C(O)R^{b9}$, $NR^{c9}C(O)OR^{a9}$, $NR^{c9}C(O)NR^{c9}R^{d9}$, $C(=NR^{e9})R^{b9}$, $C(=NR^{e9})NR^{c9}R^{d9}$, $C(=NOR^{a9})R^{b9}$, $C(=NOR^{a9})OR^{a9}$, $NR^{c9}C(=NR^{e9})NR^{c9}R^{d9}$, $NR^{c9}C(=NR^{e9})R^{b9}$, $NRCS(O)R^{b9}$, $NR^{c9}S(O)NR^{c9}R^{d9}$, $NR^{c9}S(O)_2R^{b9}$, $NR^{c9}S(O)(=NR^{e9})R^{b9}$, $NR^{c9}S(O)_2NR^{c9}R^{d9}$, $S(O)R^{b9}$, $S(O)NR^{c9}R^{d9}$, $S(O)_2R^{b9}$, $S(O)_2NR^{c9}R^{d9}$, $OS(O)(=NR^{e9})R^{b9}$, and $OS(O)_2R^{b9}$, wherein the $C_{1-6}$ alkyl, $C_{2-6}$ alkenyl, $C_{2-6}$ alkynyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^9$ are each optionally substituted with 1, 2, 3, 4, 5, 6, 7, or 8 independently selected $R^{9A}$ substituents;

each $R^{a9}$, $R^{c9}$, and $R^{d9}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a9}$, $R^{c9}$ and $R^{d9}$ are each optionally substituted with 1, 2, 3, 4, 5, 6, 7, or 8 independently selected $R^{9A}$ substituents;

or, any $R^{c9}$ and $R^{d9}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, 4, 5, 6, 7, or 8 independently selected $R^{9A}$ substituents;

each $R^{c99}$ and $R^{d99}$ is independently selected from H, $C_{1-6}$ alkyl, $C_{1-6}$ haloalkyl, $C_{2-6}$ alkenyl, $C_{2-6}$ alkynyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a9}$, $R^{c9}$ and $R^{d9}$ are each optionally substituted with 1, 2, 3, 4, 5, 6, 7, or 8 independently selected $R^{9A}$ substituents;

each $R^{b9}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b9}$ are each optionally substituted with 1, 2, 3, 4, 5, 6, 7, or 8 independently selected $R^{9A}$ substituents;

each $R^{e9}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{9A}$ is independently selected from halo, oxo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a91}$, $SR^{a91}$, NHOR a91, $C(O)R^{b91}$, $C(O)NR^{c91}R^{d91}$, $C(O)NR^{c91}(OR^{a91})$, $C(O)OR^{a91}$, OC(O)

$R^{b91}$, $OC(O)NR^{c91}R^{d91}$, $NR^{c91}R^{d91}$, $NR^{c91}NR^{c91}R^{d91}$, $NR^{c91}C(O)R^{b91}$, $NR^{c91}C(O)OR^{a91}$, $NR^{c91}C(O)NR^{c91}R^{d91}$, $C(=NR^{e91})R^{b91}$, $C(=NR^{e91})NR^{c91}R^{d91}$, $C(=NOR^{a91})R^{b91}$, $C(=NOR^{a91})OR^{a91}$, $NR^{c91}C(=NR^{e91})NR^{c91}R^{d91}$, $NR^{c91}C(=NR^{e91})R^{b91}$, $NR^{d91}S(O)R^{b91}$, $NR^{d91}S(O)NR^{c91}R^{d91}$, $NR^{c91}S(O)_2R^{b91}$, $NR^{c91}S(O)(=NR^{e91})R^{b91}$, $NR^{c91}S(O)_2NR^{c91}R^{d91}$, $S(O)R^{d91}$, $S(O)NR^{c91}R^{d91}$, $S(O)_2R^{b91}$, $S(O)_2NR^{c91}R^{d91}$, $OS(O)(=NR^{e91})R^{b91}$, and $OS(O)_2R^{b91}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{9A}$ are each optionally substituted with 1, 2, 3, or 4 independently selected $R^M$ substituents;

each $R^{a91}$, $R^{c91}$, and $R^{d91}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a91}$, $R^{c91}$ and $R^{d91}$ are each optionally substituted with 1, 2, 3, or 4 independently selected $R^M$ substituents;

or, any $R^{c91}$ and $R^{d91}$ attached to the same N atom, together with the N atom to which they are attached, form a 5-6 membered heteroaryl or a 4-7 membered heterocycloalkyl group, wherein the 5-6 membered heteroaryl or 4-7 membered heterocycloalkyl group is optionally substituted with 1, 2, 3, or 4 independently selected $R^M$ substituents;

each $R^{b91}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{b91}$ are each optionally substituted with 1, 2, 3, or 4 independently selected $R^M$ substituents;

each $R^{e91}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

$R^{10}$ is selected from H, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a10}$, $SR^{a10}$, $NHOR^{a10}$, $C(O)R^{b10}$, $C(O)NR^{c10}R^{d10}$, $C(O)NR^{c10}(OR^{a10})$, $C(O)OR^{a10}$, $OC(O)R^{b10}$, $OC(O)NR^{c10}R^{d10}$, $NR^{c10}R^{d10}$, $NR^{c10}NR^{c10}R^{d10}$, $NR^{c10}C(O)R^{b10}$, $NR^{c10}C(O)OR^{a10}$, $NR^{c10}C(O)NR^{c10}R^{d10}$, $C(=NR^{e10})R^{b10}$, $C(=NR^{e10})NR^{c10}R^{d10}$, $C(=NOR^{a10})R^{b10}$, $C(=NOR^{a10})OR^{a10}$, $NR^{c10}C(=NR^{e10})NR^{c10}R^{d10}$, $NR^{c10}C(=NR^{e10})R^{b10}$, $NR^{c10}S(O)R^{b10}$, $NR^{c10}S(O)NR^{c10}R^{d10}$, $NR^{c10}S(O)_2R^{b10}$, $NR^{c10}S(O)(=NR^{e10})R^{b10}$, $NR^{c10}S(O)_2NR^{c10}R^{d10}$, $S(O)R^{b10}$, $S(O)NR^{c10}R^{d10}$, $S(O)_2R^{b10}$, $S(O)_2NR^{c10}R^{d10}$, $OS(O)(=NR^{e10})R^{b10}$, and $OS(O)_2R^{b10}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_1$-6 alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{10}$ are each optionally substituted with 1, 2, 3, 4, 5, 6, 7, or 8 independently selected $R^{10A}$ substituents;

each $R^{a10}$, $R^{c10}$, and $R^{d10}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a10}$, $R^{e10}$ and $R^{d10}$ are each optionally substituted with 1, 2, 3, 4, 5, 6, 7, or 8 independently selected $R^{10A}$ substituents;

or, any $R^{c10}$ and $R^{d10}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, 4, 5, 6, 7, or 8 independently selected $R^{10A}$ substituents;

each $R^{b10}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b10}$ are each optionally substituted with 1, 2, 3, 4, 5, 6, 7, or 8 independently selected $R^{10A}$ substituents;

each $R^{e10}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{10A}$ is independently selected from halo, oxo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a101}$, $SR^{a101}$, $NHOR^{a101}$, $C(O)R^{b101}$, $C(O)NR^{c101}R^{d101}$, $C(O)NR^{c101}(OR^{a101})$, $C(O)OR^{a101}$, $OC(O)R^{b101}$, $OC(O)NR^{c101}R^{d101}$, $NR^{c101}R^{d101}$, $NR^{c101}NR^{c101}R^{d101}$, $NR^{c101}C(O)R^{b101}$, $NR^{c101}C(O)$ $OR^{a101}$, $NR^{c101}C(O)NR^{c101}R^{d101}$, $C(=NR^{e101})R^{b101}$, $C(=NR^{e101})NR^{c101}R^{d101}$, $C(=NOR^{a101})R^{b101}$, $C(=NOR^{a101})OR^{a101}$, $NR^{c101}C(=NR^{e101})NR^{c101}R^{d101}$, $NR^{c101}C(=NR^{e101})R^{b101}$, $NR^{c101}S(O)R^{b101}$, $NR^{c101}S(O)NR^{c101}R^{d101}$, $NR^{c101}S(O)_2R^{b101}$, $NR^{c101}S(O)(=NR^{e101})R^{b101}$, $NR^{c101}S(O)_2NR^{c101}R^{d101}$, $S(O)R^{b101}$ $S(O)NR^{c101}R^{d101}$, $S(O)_2R^{b101}$, $S(O)_2NR^{c101}R^{d101}$, $OS(O)(=NR^{e101})R^{b101}$, and $OS(O)_2R^{b101}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{10A}$ are each optionally substituted with 1, 2, 3, or 4 independently selected $R^M$ substituents;

each $R^{a101}$, $R^{c101}$, and $R^{d101}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a101}$, $R^{c101}$ and $R^{d101}$ are each optionally substituted with 1, 2, 3, or 4 independently selected $R^M$ substituents;

or, any $R^{c101}$ and $R^{d101}$ attached to the same N atom, together with the N atom to which they are attached, form a 5-6 membered heteroaryl or a 4-7 membered heterocycloalkyl group, wherein the 5-6 membered heteroaryl or 4-7 membered heterocycloalkyl group is optionally substituted with 1, 2, 3, or 4 independently selected $R^M$ substituents;

each $R^{b101}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{b101}$ are each optionally substituted with 1, 2, 3, or 4 independently selected $R^M$ substituents;

each $R^{e101}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

$L^1$ is $C_{1-3}$ alkyl, $C_{2-3}$ alkenyl, $C_{2-3}$ alkynyl, $C_{3-6}$ cycloalkyl, or 4-6 membered heterocycloalkyl;

$Cy^1$ is a $C_{6-10}$ aryl or 5-10 membered heteroaryl, wherein the $C_{6-10}$ aryl and 5-10 membered heteroaryl are each optionally substituted with 1, 2, 3, 4, 5, 6, 7, or 8 independently selected $R^{11}$ substituents;

each $R^{11}$ is independently selected from halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a11}$, $SR^{a11}$, $NHOR^{a11}$, $C(O)R^{b11}$, $C(O)NR^{c11}R^{d11}$, $C(O)NR^{c11}(OR^{a11})$, $C(O)OR^{a11}$, $OC(O)R^{b11}$, $OC(O)NR^{c11}R^{d11}$, $NR^{c11}R^{d11}$, $NR^{c11}NR^{c11}R^{d11}$, $NR^{c11}C(O)R^{b11}$, $NR^{c11}C(O)OR^{a11}$, $NR^{c11}C(O)NR^{c11}R^{d11}$, $C(=NR^{e11})R^{b11}$, $C(=NR^{e11})NR^{c11}R^{d11}$, $NR^{c11}C(=NR^{e11})NR^{c11}R^{d11}$, $NR^{c11}C(=NR^{e11})R^{b11}$, $NR^{c11}S(O)R^{b11}$, $NR^{c11}S(O)NR^{c11}R^{d11}$, $NR^{c11}S(O)_2R^{b11}$, $NR^{c11}S(O)(=NR^{e11})R^{b11}$, $NR^{c11}S(O)_2NR^{c11}R^{d11}$, $S(O)R^{b11}$, $S(O)NR^{c11}R^{d11}$, $S(O)_2R^{b11}$, $S(O)_2NR^{c11}R^{d11}$, $OS(O)(=NR^{e11})R^{b11}$, and $OS(O)_2R^{b11}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_1$-6 alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{11}$ are each optionally substituted with 1, 2, 3, 4, 5, 6, 7, or 8 independently selected $R^{11A}$ substituents;

each $R^{a11}$, $R^{c11}$, and $R^{d11}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a11}$, $R^{c11}$ and $R^{d11}$ are each optionally substituted with 1, 2, 3, 4, 5, 6, 7, or 8 independently selected $R^{11A}$ substituents;

or, any $R^{c11}$ and $R^{d11}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, 4, 5, 6, 7, or 8 independently selected $R^{11A}$ substituents;

each $R^{b11}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b11}$ are each optionally substituted with 1, 2, 3, 4, 5, 6, 7, or 8 independently selected $R^{11A}$ substituents;

each $R^{e11}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{11A}$ is independently selected from halo, $C_{1-6}$ alkyl, $C_{1-6}$ haloalkyl, $C_{2-6}$ alkenyl, $C_2$-6 alkynyl, phenyl, $C_{3-7}$ cycloalkyl, 5-6 membered heteroaryl, 4-7 membered heterocycloalkyl, CN, $NO_2$, $OR^{a111}$, $C(O)NR^{c111}R^{d111}$, $C(O)OR^{a111}$, $NR^{c111}R^{d111}$, $S(O)NR^{c111}R^{d111}$, $S(O)_2R^{b111}$, $S(O)_2NR^{c111}R^{d111}$, and $OS(O)_2R^{b111}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, and 4-7 membered heterocycloalkyl of $R^{11A}$ are each optionally substituted with 1, 2, 3, or 4 independently selected $R^M$ substituents;

each $R^{a111}$, $R^{c111}$, and $R^{d111}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a111}$, $R^{c111}$ and $R^{d111}$ are each optionally substituted with 1, 2, 3, or 4 independently selected $R^M$ substituents;

or, any $R^{c111}$ and $R^{d111}$ attached to the same N atom, together with the N atom to which they are attached, form a 5-6 membered heteroaryl or a 4-7 membered heterocycloalkyl group, wherein the 5-6 membered heteroaryl or 4-7 membered heterocycloalkyl group is optionally substituted with 1, 2, 3, or 4 independently selected $R^M$ substituents;

each $R^{b111}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{b111}$ are each optionally substituted with 1, 2, 3, or 4 independently selected $R^M$ substituents;

$R^{12}$ is selected from H, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_1$-6 alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a12}$, $SR^{a12}$, $NHOR^{a12}$, $C(O)R^{b12}$, $C(O)NR^{c12}R^{d12}$, $C(O)NR^{c12}(OR^{a12})$, $C(O)OR^{a12}$, $OC(O)R^{b12}$, $OC(O)NR^{c12}R^{d12}$, $NR^{c12}R^{d12}$, $NR^{c12}NR^{c12}R^{d12}$, $NR^{c12}C(O)R^{b12}$, $NR^{c12}C(O)OR^{a12}$, $NR^{c12}C(O)NR^{c12}R^{d12}$, $C({=}NR^{e12})R^{b12}$, $C({=}NR^{e12})$ $NR^{c12}R^{d12}$, $NR^{c12}C({=}NR^{e12})$ $NR^{c12}R^{d12}$, $NR^{c12}C({=}NR^{e12})R^{b12}$, $NR^{c12}S(O)R^{b12}$, $NR^{c12}S(O)NR^{c12}R^{d12}$, $NR^{c12}S(O)_2R^{b12}$, $NR^{c12}S(O)({=}NR^{e12})R^{b12}$, $NR^{c12}S(O)_2NR^{c12}R^{d12}$, $S(O)R^{b12}$, $S(O)NR^{c12}R^{d12}$ $S(O)_2R^{b12}$, $S(O)_2NR^{c12}R^{d12}$, $OS(O)({=}NR^{e12})R^{b12}$, and $OS(O)_2R^{b12}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{12}$ are each optionally substituted with 1, 2, 3, 4, 5, 6, 7, or 8 independently selected $R^{12A}$ substituents;

each $R^{a12}$, $R^{c12}$, and $R^{d12}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a12}$, $R^{c12}$ and $R^{d12}$ are each optionally substituted with 1, 2, 3, 4, 5, 6, 7, or 8 independently selected $R^{12A}$ substituents;

or, any $R^{c12}$ and $R^{d12}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, 4, 5, 6, 7, or 8 independently selected $R^{12A}$ substituents;

each $R^{b12}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b12}$ are each optionally substituted with 1, 2, 3, 4, 5, 6, 7, or 8 independently selected $R^{12A}$ substituents;

each $R^{e12}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{12A}$ is independently selected from halo, $C_{1-6}$ alkyl, $C_{1-6}$ haloalkyl, $C_{2-6}$ alkenyl, $C_2$-6 alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a121}$, $SR^{a121}$, $NHOR^{a121}$, $C(O)R^{b121}$, $C(O)NR^{c121}R^{d121}$, $C(O)NR^{c121}(OR^{a121})$, $C(O)OR^{a121}$, $OC(O)R^{b121}$, $OC(O)NR^{c121}R^{d121}$, $NR^{c121}R^{d121}$, $NR^{c121}NR^{c121}R^{d121}$, $NR^{c121}C(O)R^{b121}$, $NR^{c121}C(O)OR^{a121}$, $NR^{c121}C(O)NR^{c121}R^{d121}$, $C({=}NR^{e121})R^{b121}$, $C({=}NR^{e121})NR^{c121}R^{d121}$, $NR^{c121}C({=}NR^{e121})NR^{c121}R^{d121}$, $NR^{c121}C({=}NR^{e121})R^{b121}$, $NR^{c121}S(O)R^{b121}$, $NR^{c121}S(O)NR^{c121}R^{d121}$, $NR^{c121}S(O)_2R^{b121}$, $NR^{c121}S(O)({=}NR^{e121})R^{b121}$, $NR^{c121}S(O)_2NR^{c121}R^{d121}$, $S(O)R^{b121}$, $S(O)NR^{c121}R^{d121}$, $S(O)_2R^{b121}$, $S(O)_2NR^{c121}R^{d121}$ $OS(O)({=}NR^{e121})R^{b121}$, and $OS(O)_2R^{b121}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{12A}$ are each optionally substituted with 1, 2, 3, 4, 5, 6, 7, or 8 independently selected $R^{12B}$ substituents;

each $R^{a121}$, $R^{c121}$, and $R^{d121}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of Ral21, $R^{c121}$ and $R^{d121}$ are each optionally substituted with 1, 2, 3, 4, 5, 6, 7, or 8 independently selected $R^{12B}$ substituents;

or, any $R^{c121}$ and $R^{d121}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, 4, 5, 6, 7, or 8 independently selected $R^{12B}$ substituents;

each $R^{b121}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b121}$ are each optionally substituted with 1, 2, 3, 4, 5, 6, 7, or 8 independently selected $R^{12B}$ substituents;

each $R^{e121}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{12B}$ is independently selected from halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, CN, $NO_2$, $OR^{a122}$, $C(O)NR^{c122}R^{d122}$, $C(O)OR^{a122}$, $NR^{c122}R^{d122}$, $S(O)NR^{c122}R^{d122}$, $S(O)_2R^{b122}$, $S(O)_2NR^{c122}R^{d122}$, and $OS(O)_2R^{b122}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, and 4-7 membered heterocycloalkyl of $R^{12B}$ are each optionally substituted with 1, 2, 3, or 4 independently selected $R^{M}$ substituents;

each $R^{a122}$, $R^{c122}$, and $R^{d122}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a122}$, $R^{c122}$ and $R^{d122}$ are each optionally substituted with 1, 2, 3, or 4 independently selected $R^{M}$ substituents;

or, any $R^{c122}$ and $R^{d122}$ attached to the same N atom, together with the N atom to which they are attached, form a 5-6 membered heteroaryl or a 4-7 membered heterocycloalkyl group, wherein the 5-6 membered heteroaryl or 4-7 membered heterocycloalkyl group is optionally substituted with 1, 2, 3, or 4 independently selected $R^{M}$ substituents;

each $R^{b122}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{b122}$ are each optionally substituted with 1, 2, 3, or 4 independently selected $R^{M}$ substituents; and each $R^{M}$ is independently selected from H, OH, halo, oxo, CN, C(O)OH, $NH_2$, $NO_2$, $SF_5$, $C_{1-6}$ alkyl, $C_{1-6}$ alkoxy, $C_{1-6}$ haloalkoxy, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-.

2. The compound of claim 1, or a pharmaceutically acceptable salt thereof, wherein U is C(O) and V is $NR^6$.

3. The compound of claim 1, or a pharmaceutically acceptable salt thereof, wherein $R^6$ is selected from H, halo, $C_{1-6}$ alkyl, $C_{1-6}$ haloalkyl, $C_{2-6}$ alkenyl, and $C_{2-6}$ alkynyl.

4. The compound of claim 1, or a pharmaceutically acceptable salt thereof, wherein $R^6$ is H or $C_{1-6}$ alkyl.

5. The compound of claim 1, or a pharmaceutically acceptable salt thereof, wherein $R^6$ is methyl.

6. The compound of claim 1, or a pharmaceutically acceptable salt thereof, wherein U is O and V is C(O).

7. The compound of claim 1, or a pharmaceutically acceptable salt thereof, wherein W is $CR^7$ or N.

8. The compound of claim 1, or a pharmaceutically acceptable salt thereof, wherein $R^7$ is selected from H, halo, $C_{1-6}$ alkyl, $C_{1-6}$ haloalkyl, $C_{2-6}$ alkenyl, and $C_{2-6}$ alkynyl.

9. The compound of claim 1, or a pharmaceutically acceptable salt thereof, wherein W is CH or N.

10. The compound of claim 1, or a pharmaceutically acceptable salt thereof, wherein X is $CR^8$.

11. The compound of claim 1, or a pharmaceutically acceptable salt thereof, wherein $R^8$ is selected from H, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, CN, and $OR^{a8}$, wherein $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, and 4-7 membered heterocycloalkyl of $R^8$ are each optionally substituted with 1, 2, 3, or 4 independently selected $R^{8A}$ substituents.

12. The compound of claim 1, or a pharmaceutically acceptable salt thereof, wherein $R^8$ is selected from H, halo, $C_{1-6}$ alkyl, $C_{1-6}$ haloalkyl, $C_{2-6}$ alkenyl, $C_{2-6}$ alkynyl, and CN, wherein $C_{1-6}$ alkyl, $C_{2-6}$ alkenyl, and $C_{2-6}$ alkynyl of $R^8$ are each optionally substituted with 1, 2, 3, or 4 independently selected $R^{8A}$ substituents.

13. The compound of claim 1, or a pharmaceutically acceptable salt thereof, wherein each $R^{8A}$ is independently selected from halo, $C_{1-6}$ alkyl, $C_{1-6}$ haloalkyl, $C_{2-6}$ alkenyl, $C_{2-6}$ alkynyl, and CN.

14. The compound of claim 1, or a pharmaceutically acceptable salt thereof, wherein each $R^{8A}$ is CN.

15. The compound of claim 1, or a pharmaceutically acceptable salt thereof, wherein $R^8$ is selected from H, cyanomethyl, and cyano.

16. The compound of claim 1, or a pharmaceutically acceptable salt thereof, wherein Y is $CR^9$.

17. The compound of claim 1, or a pharmaceutically acceptable salt thereof, wherein $R^9$ is selected from H, halo, $C_{1-6}$ alkyl, $C_{1-6}$ haloalkyl, $C_{2-6}$ alkenyl, $C_{2-6}$ alkynyl, and CN, wherein $C_{1-6}$ alkyl, $C_{2-6}$ alkenyl, and $C_{2-6}$ alkynyl of $R^9$ are each optionally substituted with 1, 2, 3, or 4 independently selected $R^{9A}$ substituents.

18. The compound of claim 1, or a pharmaceutically acceptable salt thereof, wherein each $R^{9A}$ is independently selected from halo, $C_{1-6}$ alkyl, $C_{1-6}$ haloalkyl, $C_{2-6}$ alkenyl, $C_{2-6}$ alkynyl, and CN.

19. The compound of claim 1, or a pharmaceutically acceptable salt thereof, wherein each $R^{9A}$ is CN.

20. The compound of claim 1, or a pharmaceutically acceptable salt thereof, wherein $R^9$ is selected from H, cyanomethyl, and cyano.

21. The compound of claim 1, or a pharmaceutically acceptable salt thereof, wherein Z is $CR^{10}$.

22. The compound of claim 1, or a pharmaceutically acceptable salt thereof, wherein $R^{10}$ is selected from H, halo, $C_{1-6}$ alkyl, $C_{1-6}$ haloalkyl, $C_{2-6}$ alkenyl, and $C_{2-6}$ alkynyl.

23. The compound of claim 1, or a pharmaceutically acceptable salt thereof, wherein Z is CH.

24. The compound of claim 1, or a pharmaceutically acceptable salt thereof, wherein Z is N.

25. The compound of claim 1, or a pharmaceutically acceptable salt thereof, wherein n is 0 or 1.

26. The compound of claim 1, or a pharmaceutically acceptable salt thereof, wherein each $R^2$ is independently selected from halo, $C_{1-6}$ alkyl, $C_{1-6}$ haloalkyl, $C_{2-6}$ alkenyl, and $C_{2-6}$ alkynyl.

27. The compound of claim 1, or a pharmaceutically acceptable salt thereof, wherein each $R^2$ is independently selected from $C_{1-6}$ alkyl.

28. The compound of claim 1, or a pharmaceutically acceptable salt thereof, wherein each $R^2$ is methyl.

29. The compound of claim 1, or a pharmaceutically acceptable salt thereof, wherein $R^3$ is selected from H, halo, $C_{1-6}$ alkyl, $C_{1-6}$ haloalkyl, $C_{2-6}$ alkenyl, and $C_{2-6}$ alkynyl.

30. The compound of claim 1, or a pharmaceutically acceptable salt thereof, wherein $R^3$ is selected from H and $C_{1-6}$ alkyl.

31. The compound of claim 1, or a pharmaceutically acceptable salt thereof, wherein $R^3$ is methyl.

32. The compound of claim 1, or a pharmaceutically acceptable salt thereof, wherein each $R^4$ is independently selected from H, halo, $C_{1-6}$ alkyl, $C_{1-6}$ haloalkyl, $C_{2-6}$ alkenyl, and $C_{2-6}$ alkynyl.

33. The compound of claim 1, or a pharmaceutically acceptable salt thereof, wherein each $R^4$ is H.

34. The compound of claim 1, or a pharmaceutically acceptable salt thereof, wherein $L^1$ is $C_{1-3}$ alkyl.

35. The compound of claim 1, or a pharmaceutically acceptable salt thereof, wherein $L^1$ is CH.

36. The compound of claim 1, or a pharmaceutically acceptable salt thereof, wherein $Cy^1$ is phenyl or 5-6 membered heteroaryl, wherein the phenyl and 5-6 membered heteroaryl of $Cy^1$ are each optionally substituted with 1, 2, 3, or 4 independently selected $R^{11}$ substituents.

37. The compound of claim 1, or a pharmaceutically acceptable salt thereof, wherein $Cy^1$ is phenyl, which is optionally substituted with 1, 2, 3, or 4 independently selected $R^{11}$ substituents.

38. The compound of claim 1, or a pharmaceutically acceptable salt thereof, wherein each $R^{11}$ is independently selected from halo, $C_{1-6}$ alkyl, $C_{1-6}$ haloalkyl, $C_{2-6}$ alkenyl, and $C_{2-6}$ alkynyl.

39. The compound of claim 1, or a pharmaceutically acceptable salt thereof, wherein each $R^{11}$ is independently selected from halo.

40. The compound of claim 1, or a pharmaceutically acceptable salt thereof, wherein $Cy^1$ is fluorophenyl.

41. The compound of any claim 1, or a pharmaceutically acceptable salt thereof, wherein $R^{12}$ is phenyl or 5-6 membered heteroaryl, wherein the phenyl and 5-6 membered heteroaryl of $R^{12}$ are each optionally substituted with 1, 2, 3, or 4 independently selected $R^{12A}$ substituents.

42. The compound of claim 1, or a pharmaceutically acceptable salt thereof, wherein $R^{12}$ is phenyl, which is optionally substituted with 1, 2, 3, or 4 independently selected $R^{12A}$ substituents.

43. The compound of claim 1, or a pharmaceutically acceptable salt thereof, wherein each $R^{12A}$ is independently selected from halo, $C_{1-6}$ alkyl, $C_{1-6}$ haloalkyl, $C_{2-6}$ alkenyl, and $C_{2-6}$ alkynyl.

44. The compound of claim 1, or a pharmaceutically acceptable salt thereof, wherein each $R^{12A}$ is independently selected from halo.

45. The compound of claim 1, or a pharmaceutically acceptable salt thereof, wherein $R^{12}$ is fluorophenyl.

46. The compound of claim 1, or a pharmaceutically acceptable salt thereof, wherein $Cy^1$ and $R^{12}$ are each fluorophenyl.

47. The compound of claim 1, or a pharmaceutically acceptable salt thereof, wherein:

$\overset{---}{---}$ is a single or double bond;

U is O and V is C(O); or

U is C(O) and V is $NR^6$;

W is $CR^7$ or N;

X is $CR^8$;

Y is $CR^9$ or N;

Z is $CR^{10}$ or N;

each $R^2$ is independently selected from halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, CN, $NO_2$, $OR^{a2}$, $NHOR^{a2}$, $C(O)R^{b2}$, $C(O)NR^{c2}R^{d2}$, $C(O)NR^{c2}(OR^{a2})$, $C(O)OR^{a2}$, $OC(O)R^{b2}$, $OC(O)NR^{c2}R^{d2}$, $NR^{c2}R^{d2}$, $NR^{c2}NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NR^{e2})NR^{c2}R^{d2}$, $NR^{c9}C(=NR^{e2})NR^{c2}R^{d2}$, $NR^{c2}C(=NR^{e2})R^{b2}$, $NR^{c2}S(O)R^{b2}$, $NR^{c2}S(O)NR^{c2}R^{d2}$, $NR^{c2}S(O)_2R^{b2}$, $NR^{c2}S(O)(=NR^{e2})R^{b2}$, $NR^{c2}S(O)_2NR^{c2}R^{d2}$, $S(O)R^{b2}$, $S(O)NR^{c2}R^{d2}$, $S(O)_2R^{b2}$, $S(O)_2NR^{c2}R^{d2}$, $OS(O)(=NR^{e2})R^{b2}$, and $OS(O)_2R^{b2}$;

each $R^{a2}$, $R^{c2}$, and $R^{d2}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

or, any $R^{c2}$ and $R^{d2}$ attached to the same N atom, together with the N atom to which they are attached, form a 5-6 membered heteroaryl or a 4-7 membered heterocycloalkyl group;

each $R^{b2}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

each $R^{e2}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

$R^3$ is selected from H, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, and 4-7 membered heterocycloalkyl, wherein the $C_{1-6}$ alkyl, $C_{2-6}$ alkenyl, $C_{2-6}$ alkynyl, phenyl, $C_{3-7}$ cycloalkyl, 5-6 membered heteroaryl, and 4-7 membered heterocycloalkyl of $R^3$ are each optionally substituted with 1, 2, 3, or 4 independently selected $R^M$ substituents;

each $R^4$ is independently selected from H, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, wherein the $C_{1-6}$ alkyl, $C_{2-6}$ alkenyl, $C_{2-6}$ alkynyl, phenyl, $C_{3-7}$ cycloalkyl, 5-6 membered heteroaryl, and 4-7 membered heterocycloalkyl of $R^4$ are each optionally substituted with 1, 2, 3, or 4 independently selected $R^M$ substituents;

or, two $R^4$ groups attached to the same carbon atom, together with the carbon atom to which they are attached, form a $C_{3-6}$ cycloalkyl, which is optionally substituted with 1, 2, 3, or 4 independently selected $R^M$ substituents;

$R^6$ is selected from H, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, wherein the $C_{1-6}$ alkyl, $C_{2-6}$ alkenyl, $C_{2-6}$ alkynyl, phenyl, $C_{3-7}$ cycloalkyl, 5-6 membered heteroaryl, and 4-7 membered heterocycloalkyl of $R^6$ are each optionally substituted with 1, 2, 3, or 4 independently selected $R^M$ substituents;

$R^7$ is selected from H, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_1$-6 alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a7}$, $SR^{a7}$, $NHOR^{a7}$, $C(O)R^{b7}$, $C(O)NR^{c7}R^{d7}$, $C(O)NR^{c7}(OR^{a7})$, $C(O)OR^{a7}$, $OC(O)R^{b7}$, $OC(O)NR^{c7}R^{d7}$, $NR^{c7}R^{d7}$, $NR^{c7}NR^{c7}R^{d7}$, $NR^{c7}C(O)R^{b7}$, $NR^{c7}C(O)OR^{a7}$, $NR^{c7}C(O)NR^{c7}R^{d7}$, $C(=NR^{e7})R^{b7}$, $C(=NR^{e7})NR^{c7}R^{d7}$, $C(=NOR^{a7})R^{b7}$, $C(=NOR^{a7})OR^{a7}$, $NR^{c7}C(=NR^{e7})NR^{c7}R^{d7}$, $NR^{c7}C(=NR^{e7})R^{b7}$, $NR^{c7}S(O)R^{b7}$, $NR^{c7}S(O)NR^{c7}R^{d7}$, $NR^{c7}S(O)_2R^{b7}$, $NR^{c7}S(O)(=NR^{e7})R^{b7}$, $NR^{c7}S(O)_2NR^{c7}R^{d7}$, $S(O)R^{b7}$, $S(O)NR^{c7}R^{d7}$, $S(O)_2R^{b7}$, $S(O)_2NR^{c7}R^{d7}$, $OS(O)(=NR^{e7})R^{b7}$, and $OS(O)_2R^{b7}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^7$ are each optionally substituted with 1, 2, 3, or 4 independently selected $R^{7A}$ substituents;

each $R^{a7}$, $R^{c7}$, and $R^{d7}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a7}$, $R^{c7}$ and $R^{d7}$ are each optionally substituted with 1, 2, 3, or 4 independently selected $R^{7A}$ substituents;

or, any $R^{c7}$ and $R^{d7}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{7A}$ substituents;

each $R^{b7}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b7}$ are each optionally substituted with 1, 2, 3, or 4 independently selected $R^{7A}$ substituents;

each $R^{e7}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{7A}$ is independently selected from halo, oxo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a71}$, $SR^{a71}$, $NHOR^{a71}$, $C(O)R^{b71}$, $C(O)NR^{c71}R^{d71}$, $C(O)NR^{c71}(OR^{a71})$, $C(O)OR^{a71}$, $OC(O)R^{b71}$, $OC(O)NR^{c71}R^{d71}$, $NR^{b71}R^{d71}$, $NR^{c71}NR^{c71}R^{d71}$, $NR^{c71}C(O)R^{b71}$, $NR^{b71}C(O)OR^{a71}$, $NR^{c71}C(O)NR^{c71}R^{d71}$, $C(=NR^{e71})R^{b71}$, $C(=NR^{e71})NR^{c71}R^{d71}$, $C(=NOR^{a71})R^{b71}$, $C(=NOR^{a71})OR^{a71}$, $NR^{c71}C(=NR^{e71})NR^{c71}R^{d71}$, $NR^{c71}C(=NR^{e71})R^{b71}$, $NR^{c71}S(O)R^{b71}$, $NR^{c71}S(O)NR^{c71}R^{d71}$, $NR^{c71}S(O)_2R^{b71}$, $NR^{c71}S(O)(=NR^{e71})R^{b71}$, $NR^{c71}S(O)_2NR^{e71}R^{d71}$, $S(O)R^{b71}$, $S(O)NR^{c71}R^{d71}$, $S(O)_2R^{b71}$, $S(O)_2NR^{c71}R^{d71}$, $OS(O)(=NR^{e71})R^{b71}$, and $OS(O)_2R^{b71}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{7A}$ are each optionally substituted with 1, 2, 3, or 4 independently selected $R^M$ substituents;

each $R^{a71}$, $R^{c71}$, and $R^{d71}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a71}$, $R^{c71}$ and $R^{d71}$ are each optionally substituted with 1, 2, 3, or 4 independently selected $R^M$ substituents;

or, any $R^{c71}$ and $R^{d71}$ attached to the same N atom, together with the N atom to which they are attached, form a 5-6 membered heteroaryl or a 4-7 membered heterocycloalkyl group, wherein the 5-6 membered heteroaryl or 4-7 membered heterocycloalkyl group is optionally substituted with 1, 2, 3, or 4 independently selected $R^M$ substituents;

each $R^{b71}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{b71}$ are each optionally substituted with 1, 2, 3, or 4 independently selected $R^M$ substituents;

each $R^{e71}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

$R^8$ is selected from H, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_1$-6 alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a8}$, $SR^{a8}$, $NHOR^{a8}$, $C(O)R^{b8}$, $C(O)NR^{c8}R^{d8}$, $C(O)NR^{c8}(OR^{a8})$, $C(O)OR^{a8}$, $OC(O)R^{b8}$, $OC(O)NR^{c8}R^{d8}$, $NR^{c8}R^{d8}$, $NR^{c8}NR^{c8}R^{d8}$, $NR^{c8}C(O)R^{b8}$, $NR^{c8}C(O)OR^{a8}$, $NR^{c8}C(O)NR^{c8}R^{d8}$, $C(=NR^{e8})R^{b8}$, $C(=NR^{e8})NR^{c8}R^{d8}$, $C(=NOR^{a8})R^{b8}$, $C(=NOR^{a8})OR^{a8}$, $NR^{c8}C(=NR^{e8})NR^{c8}R^{d8}$, $NR^{c8}C(=NR^{e8})R^{b8}$, $NR^{c8}S(O)R^{b8}$, $NR^{c8}S(O)NR^{c8}R^{d8}$, $NR^{c8}S(O)_2R^{b8}$, $NR^{c8}S(O)(=NR^{e8})R^{b8}$, $NR^{c8}S(O)_2NR^{c8}R^{d8}$, $S(O)R^{b8}$, $S(O)NR^{c8}R^{d8}$, $S(O)_2R^{b8}$, $S(O)_2NR^{c8}R^{d8}$, $OS(O)(=NR^{e8})R^{b8}$, and $OS(O)_2R^{b8}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^8$ are each optionally substituted with 1, 2, 3, or 4 independently selected $R^{8A}$ substituents;

each $R^{a8}$, $R^{c8}$, and $R^{d8}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a8}$, $R^{c8}$ and $R^{d8}$ are each optionally substituted with 1, 2, 3, or 4 independently selected $R^{8A}$ substituents;

or, any $R^{c8}$ and $R^{d8}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{8A}$ substituents;

each $R^{b8}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b8}$ are each optionally substituted with 1, 2, 3, or 4 independently selected $R^{8A}$ substituents;

each $R^{e8}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{8A}$ is independently selected from halo, oxo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, CN, $NO_2$, $OR^{a81}$, $SR^{a81}$, $NHOR^{a81}$, $C(O)R^{b81}$, $C(O)NR^{c81}R^{d81}$, $C(O)NR^{c81}(OR^{a81})$, $C(O)OR^{a81}$, $OC(O)R^{b81}$, $OC(O)NR^{c81}R^{d81}$, $NR^{c81}R^{d81}$, $NR^{c81}NR^{c81}R^{d81}$, $NR^{c81}C(O)R^{b81}$, $NR^{c81}C(O)OR^{a81}$, $NR^{c81}C(O)NR^{c81}R^{d81}$, $C(=NR^{e81})R^{b81}$, $C(=NR^{e81})NR^{c81}R^{d81}$, $C(=NOR^{a81})R^{b81}$, $C(=NOR^{a81})OR^{a81}$, $NR^{c81}C(=NR^{e81})NR^{c81}R^{d81}$, $NR^{c81}C(=NR^{e81})R^{b81}$, $NR^{c81}S(O)R^{b81}$, $NR^{c81}S(O)NR^{c81}R^{d81}$, $NR^{c81}S(O)_2R^{b81}$, $NR^{c81}S(O)(=NR^{e81})R^{b81}$, $NR^{c81}S(O)_2NR^{c81}R^{d81}$, $S(O)R^{b81}$, $S(O)NR^{c81}R^{d81}$, $S(O)_2R^{b81}$, $S(O)_2NR^{c81}R^{d81}$, $OS(O)(=NR^{e81})R^{b81}$, and $OS(O)_2R^{b81}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{8A}$ are each optionally substituted with 1, 2, 3, or 4 independently selected $R^M$ substituents;

each $R^{a81}$, $R^{c81}$, and $R^{d81}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a81}$, $R^{c81}$ and $R^{d81}$ are each optionally substituted with 1, 2, 3, or 4 independently selected $R^{M}$ substituents;

or, any $R^{c81}$ and $R^{d81}$ attached to the same N atom, together with the N atom to which they are attached, form a 5-6 membered heteroaryl or a 4-7 membered heterocycloalkyl group, wherein the 5-6 membered heteroaryl or 4-7 membered heterocycloalkyl group is optionally substituted with 1, 2, 3, or 4 independently selected $R^{M}$ substituents;

each $R^{b81}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{b81}$ are each optionally substituted with 1, 2, 3, or 4 independently selected $R^{M}$ substituents;

each $R^{e81}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

$R^9$ is selected from H, halo, $C_{1-6}$ alkyl, $C_{1-6}$ haloalkyl, $C_{2-6}$ alkenyl, $C_{2-6}$ alkynyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a9}$, $SR^{a9}$, $NHOR^{a9}$, $C(O)R^{b9}$, $C(O)NR^{c9}R^{d9}$, $C(O)NR^{c9}(OR^{a9})$, $C(O)OR^{a9}$, $OC(O)R^{b9}$, $OC(O)NR^{c9}R^{d9}$, $NR^{c99}R^{d99}$, $NRCONR^{c9}R^{d9}$, $NR^{c9}C(O)R^{b9}$, $NR^{c9}C(O)OR^{a9}$, $NRCC(O)NR^{c9}R^{d9}$, $C(=NR^{e9})R^{b9}$, $C(=NR^{e9})NR^{c9}R^{d9}$, $C(=NOR^{a9})R^{b9}$, $C(=NOR^{a9})OR^{a9}$, $NR^{c2}C(=NR^{e9})NR^{c9}R^{d9}$, $NR^{c9}C(=NR^{e9})R^{b9}$, $NRCS(O)R^{b9}$, $NR^{c9}S(O)NR^{c9}R^{d9}$, $NR^{c9}S(O)_2R^{b9}$, $NR^{c9}S(O)(=NR^{e9})R^{b9}$, $NR^{c9}S(O)_2NR^{c9}R^{d9}$, $S(O)R^{b9}$, $S(O)NR^{c9}R^{d9}$, $S(O)_2R^{b9}$, $S(O)_2NR^{c9}R^{d9}$, $OS(O)(=NR^{e9})R^{b9}$, and $OS(O)_2R^{b9}$, wherein the $C_{1-6}$ alkyl, $C_{2-6}$ alkenyl, $C_{2-6}$ alkynyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^9$ are each optionally substituted with 1, 2, 3, or 4 independently selected $R^{9A}$ substituents;

each $R^{a9}$, $R^{c9}$, and $R^{d9}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a9}$, $R^{c9}$ and $R^{d9}$ are each optionally substituted with 1, 2, 3, or 4 independently selected $R^{9A}$ substituents;

or, any $R^{c9}$ and $R^{d9}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{9A}$ substituents;

each $R^{c99}$ and $R^{d99}$ is independently selected from H, $C_{1-6}$ alkyl, $C_{1-6}$ haloalkyl, $C_{2-6}$ alkenyl, $C_{2-6}$ alkynyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a9}$, $R^{c9}$ and $R^{d9}$ are each optionally substituted with 1, 2, 3, 4, 5, 6, 7, or 8 independently selected $R^{9A}$ substituents;

each $R^{b9}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b9}$ are each optionally substituted with 1, 2, 3, or 4 independently selected $R^{9A}$ substituents;

each $R^{e9}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{9A}$ is independently selected from halo, $C_{1-6}$ alkyl, $C_{1-6}$ haloalkyl, $C_{2-6}$ alkenyl, $C_{2-6}$ alkynyl, and CN;

$R^{10}$ is selected from H, halo, $C_{1-6}$ alkyl, $C_{1-6}$ haloalkyl, $C_{2-6}$ alkenyl, and $C_{2-6}$ alkynyl;

$L^1$ is $C_{1-3}$ alkyl;

$Cy^1$ is phenyl or 5-6 membered heteroaryl, wherein the phenyl or 5-6 membered heteroarylare each optionally substituted with 1, 2, 3, or 4 independently selected $R^{11}$ substituents;

each $R^{11}$ is independently selected from halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a11}$, $SR^{a11}$, $NHOR^{a11}$, $C(O)R^{b11}$, $C(O)NR^{c11}R^{d11}$, $C(O)NR^{c11}(OR^{a11})$, $C(O)OR^{a11}$, $OC(O)R^{b11}$, $OC(O)NR^{c11}R^{d11}$, $NR^{c11}R^{d11}$, $NR^{c11}NR^{c11}R^{d11}$ $NR^{c11}C(O)R^{b11}$, $NR^{c11}C(O)OR^{a11}$, $NR^{c11}C(O)NR^{c11}R^{d11}$, $C(=NR^{e11})R^{b11}$, $C(=NR^{e11})$ $NR^{c11}R^{d11}$, $NR^{c11}C({=}NR^{e11})$ $NR^{c11}R^{d11}$, $NR^{c11}C({=}NR^{e11})R^{b11}$, $NR^{c11}S(O)R^{b11}$, $NR^{c11}S(O)NR^{c11}R^{d11}$, $NR^{c11}S(O)_2R^{b11}$, $NR^{c11}S(O)({=}NR^{e11})R^{b11}$, $NR^{c11}S(O)_2NR^{c11}R^{d11}$, $S(O)R^{b11}$, $S(O)NR^{e11}R^{d11}$, $S(O)_2R^{b11}$, $S(O)_2NR^{e11}R^{d11}$, $OS(O)({=}NR^{e11})R^{b11}$, and $OS(O)_2R^{b11}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_1$-6 alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{11}$ are each optionally substituted with 1, 2, 3, or 4 independently selected $R^{11A}$ substituents;

each $R^{a11}$, $R^{c11}$, and $R^{d11}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a11}$, $R^{c11}$ and $R^{d11}$ are each optionally substituted with 1, 2, 3, or 4 independently selected $R^{11A}$ substituents;

or, any $R^{c11}$ and $R^{d11}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{11A}$ substituents;

each $R^{b11}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b11}$ are each optionally substituted with 1, 2, 3, or 4 independently selected $R^{11A}$ substituents;

each $R^{e11}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{11A}$ is independently selected from halo, $C_{1-6}$ alkyl, $C_{1-6}$ haloalkyl, $C_{2-6}$ alkenyl, $C_2$-6 alkynyl, phenyl, $C_{3-7}$ cycloalkyl, 5-6 membered heteroaryl, 4-7 membered heterocycloalkyl, CN, $NO_2$, $OR^{a11}1$, $C(O)NR^{c111}R^{d111}$, $C(O)OR^{a111}$, $NR^{c111}R^{d111}$, $S(O)NR^{c111}R^{d111}$, $S(O)_2R^{b111}$, $S(O)_2NR^{c111}R^{d111}$, and $OS(O)_2R^{b111}$, wherein the $C_{1-6}$ alkyl, $C_{2-6}$ alkenyl, $C_{2-6}$ alkynyl, phenyl, $C_3$-7 cycloalkyl, 5-6 membered heteroaryl, and 4-7 membered heterocycloalkyl of $R^{11A}$ are each optionally substituted with 1, 2, 3, or 4 independently selected $R^M$ substituents;

each $R^{a111}$, $R^{c111}$, and $R^{d111}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a111}$, $R^{c111}$ and $R^{d111}$ are each optionally substituted with 1, 2, 3, or 4 independently selected $R^M$ substituents;

or, any $R^{c111}$ and $R^{d111}$ attached to the same N atom, together with the N atom to which they are attached, form a 5-6 membered heteroaryl or a 4-7 membered heterocycloalkyl group, wherein the 5-6 membered heteroaryl or 4-7 membered heterocycloalkyl group is optionally substituted with 1, 2, 3, or 4 independently selected $R^M$ substituents;

each $R^{b111}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{b111}$ are each optionally substituted with 1, 2, 3, or 4 independently selected $R^M$ substituents;

$R^{12}$ is selected from H, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a12}$, $SR^{a12}$, $NHOR^{a12}$, $C(O)R^{b12}$, $C(O)NR^{c12}R^{d12}$ $C(O)NR^{c12}(OR^{a12})$, $C(O)OR^{a12}$, $OC(O)R^{b12}$, $OC(O)NR^{c12}R^{d12}$, $NR^{c12}R^{d12}$, $NR^{c12}NR^{c12}R^{d12}$, $NR^{c12}C(O)R^{b12}$, $NR^{c12}C(O)OR^{a12}$, $NR^{c12}C(O)NR^{c12}R^{d12}$, $C({=}NR^{e12})R^{b12}$, $C({=}NR^{e12})$ $NR^{c12}R^{d12}$, $NR^{c12}C({=}NR^{e12})$ $NR^{c12}R^{d12}$, $NR^{c12}C({=}NR^{e12})R^{b12}$, $NR^{c12}S(O)R^{b12}$, $NR^{c12}S(O)NR^{c12}R^{d12}$, $NR^{c12}S(O)_2R^{b12}$, $NR^{c12}S(O)({=}NR^{e12})R^{b12}$, $NR^{c12}S(O)_2NR^{c12}R^{d12}$, $S(O)R^{b12}$, $S(O)NR^{c12}R^{d12}$, $S(O)_2R^{b12}$, $S(O)_2NR^{c12}R^{d12}$, $OS(O)({=}NR^{e12})R^{b12}$, and $OS(O)_2R^{b12}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{12}$ are each optionally substituted with 1, 2, 3, or 4 independently selected $R^{12A}$ substituents;

each $R^{a12}$, $R^{c12}$, and $R^{d12}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a12}$, $R^{c12}$ and $R^{d12}$ are each optionally substituted with 1, 2, 3, or 4 independently selected $R^{12A}$ substituents;

or, any $R^{c12}$ and $R^{d12}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{12A}$ substituents;

each $R^{b12}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b12}$ are each optionally substituted with 1, 2, 3, or 4 independently selected $R^{12A}$ substituents;

each $R^{e12}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{12A}$ is independently selected from halo, $C_{1-6}$ alkyl, $C_{1-6}$ haloalkyl, $C_{2-6}$ alkenyl, $C_2$-6 alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a121}$, $SR^{a121}$, $NHOR^{a121}$, $C(O)R^{b121}$, $C(O)NR^{c121}R^{d121}$, $C(O)NR^{c121}(OR^{a121})$, $C(O)OR^{a121}$, $OC(O)R^{b121}$, $OC(O)NR^{c121}R^{d121}$, $NR^{c121}R^{d121}$, $NR^{c121}NR^{c121}R^{d121}$, $NR^{c121}C(O)R^{b121}$, $NR^{c121}C(O)OR^{a121}$, $NR^{c121}C(O)NR^{c121}R^{d121}$, $C(=NR^{e121})R^{b121}$, $C(=NR^{e121})NR^{c121}R^{d121}$, $NR^{c121}C(=NR^{e121})NR^{c121}R^{d121}$, $NR^{c121}C(=NR^{e121})R^{b121}$, $NR^{c121}S(O)R^{b121}$, $NR^{c121}S(O)NR^{c121}R^{d121}$, $NR^{c121}S(O)_2R^{b121}$, $NR^{c121}S(O)(=NR^{e121})R^{b121}$, $NR^{c121}S(O)_2NR^{c121}R^{d121}$, $S(O)R^{b121}$, $S(O)NR^{c121}R^{d121}$, $S(O)_2R^{b121}$, $S(O)_2NR^{c121}R^{d121}$ $OS(O)(=NR^{e121})R^{b121}$, and $OS(O)_2R^{b121}$;

each $R^{a121}$, $R^{c121}$, and $R^{d121}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

or, any $R^{c121}$ and $R^{d121}$ attached to the same N atom, together with the N atom to which they are attached, form a 5-10 membered heteroaryl or a 4-10 membered heterocycloalkyl group;

each $R^{b121}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{e121}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-; and each $R^M$ is independently selected from H, OH, halo, oxo, CN, C(O)OH, $NH_2$, $NO_2$, $SF_5$, $C_{1-6}$ alkyl, $C_{1-6}$ alkoxy, $C_{1-6}$ haloalkoxy, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-.

48. The compound of claim 1, or a pharmaceutically acceptable salt thereof, wherein:

$\equiv$ is a single or double bond;

U is O and V is C(O); or

U is C(O) and V is $NR^6$;

W is CH or N;

X is $CR^8$;

Y is $CR^9$;

Z is CH or N;

n is 0 or 1;

each $R^2$ is independently selected from halo, $C_{1-6}$ alkyl, $C_{1-6}$ haloalkyl, $C_{2-6}$ alkenyl, and $C_{2-6}$ alkynyl;

$R^3$ is selected from H, halo, $C_{1-6}$ alkyl, $C_{1-6}$ haloalkyl, $C_{2-6}$ alkenyl, and $C_{2-6}$ alkynyl;

each $R^4$ is independently selected from H, halo, $C_{1-6}$ alkyl, $C_{1-6}$ haloalkyl, $C_{2-6}$ alkenyl, and $C_{2-6}$ alkynyl;

$R^6$ is selected from H, halo, $C_{1-6}$ alkyl, $C_{1-6}$ haloalkyl, $C_{2-6}$ alkenyl, and $C_{2-6}$ alkynyl, wherein the $C_{1-6}$ alkyl, $C_{2-6}$ alkenyl, and $C_{2-6}$ alkynyl of $R^6$ are each optionally substituted with 1, 2, 3, or 4 independently selected $R^M$ substituents;

$R^8$ is selected from H, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, CN, and $OR^{a8}$, wherein $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, and 4-7 membered heterocycloalkyl of $R^8$ are each optionally substituted with 1, 2, 3, or 4 independently selected $R^{8A}$ substituents;

each $R^{8A}$ is independently selected from halo, $C_{1-6}$ alkyl, $C_{1-6}$ haloalkyl, $C_{2-6}$ alkenyl, $C_{2-6}$ alkynyl, and CN $R^9$ is selected from H, halo, $C_{1-6}$ alkyl, $C_{1-6}$ haloalkyl, $C_{2-6}$ alkenyl, $C_{2-6}$ alkynyl, and CN, wherein $C_{1-6}$ alkyl, $C_{2-6}$ alkenyl, and $C_{2-6}$ alkynyl of $R^9$ are each optionally substituted with 1, 2, 3, or 4 independently selected $R^{9A}$ substituents;

each $R^{9A}$ is independently selected from halo, $C_{1-6}$ alkyl, $C_{1-6}$ haloalkyl, $C_{2-6}$ alkenyl, $C_{2-6}$ alkynyl, and CN;

$L^1$ is $C_{1-3}$ alkyl;

$Cy^1$ is phenyl or 5-6 membered heteroaryl, wherein the phenyl or 5-6 membered heteroarylare each optionally substituted with 1, 2, 3, or 4 independently selected $R^{11}$ substituents;

each $R^{11}$ is independently selected from halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a11}$, $SR^{a11}$, $NHOR^{a11}$, $C(O)R^{b11}$, $C(O)NR^{c11}R^{d11}$, $C(O)NR^{c11}(OR^{a11})$, $C(O)OR^{a11}$, $OC(O)R^{b11}$, $OC(O)NR^{c11}R^{d11}$, $NR^{c11}R^{d11}$, $NR^{c11}NR^{c11}R^{d11}$, $NR^{c11}C(O)R^{b11}$, $NR^{c11}C(O)OR^{a11}$, $NR^{c11}C(O)NR^{c11}R^{d11}$, $C(=NR^{e11})R^{b11}$, $C(=NR^{e11})NR^{c11}R^{d11}$, $NR^{c11}C(=NR^{e11})NR^{c11}R^{d11}$, $NR^{c11}C(=NR^{e11})R^{b11}$, $NR^{c11}S(O)R^{b11}$, $NR^{c11}S(O)NR^{c11}R^{d11}$, $NR^{c11}S(O)_2R^{b11}$, $NR^{c11}S(O)(=NR^{e11})R^{b11}$, $NR^{c11}S(O)_2NR^{c11}R^{d11}$, $S(O)R^{b11}$, $S(O)NR^{c11}R^{d11}$, $S(O)_2R^{b11}$, $S(O)_2NR^{c11}R^{d11}$, $OS(O)(=NR^{e11})R^{b11}$, and $OS(O)_2R^{b11}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_1$-6 alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{11}$ are each optionally substituted with 1, 2, 3, or 4 independently selected $R^{11A}$ substituents;

each $R^{a11}$, $R^{c11}$, and $R^{c11}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a11}$, $R^{c11}$ and $R^{d11}$ are each optionally substituted with 1, 2, 3, or 4 independently selected $R^{11A}$ substituents;

or, any $R^{c11}$ and $R^{d11}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{11A}$ substituents;

each $R^{b11}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b11}$ are each optionally substituted with 1, 2, 3, or 4 independently selected $R^{11A}$ substituents;

each $R^{e11}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{11A}$ is independently selected from halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, CN, $NO_2$, $OR^{a111}$, $C(O)NR^{c111}R^{d111}$, $C(O)OR^{a111}$, $NR^{c111}R^{d111}$, $S(O)NR^{c111}R^{d111}$, $S(O)_2R^{b111}$, $S(O)_2NR^{c111}R^{d111}$, and $OS(O)_2R^{b111}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, and 4-7 membered heterocycloalkyl of $R^{11A}$ are each optionally substituted with 1, 2, 3, or 4 independently selected $R^M$ substituents;

each $R^{a111}$, $R^{c111}$, and $R^{d111}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a111}$, $R^{c111}$ and $R^{d111}$ are each optionally substituted with 1, 2, 3, or 4 independently selected $R^M$ substituents;

or, any $R^{c111}$ and $R^{d111}$ attached to the same N atom, together with the N atom to which they are attached, form a 5-6 membered heteroaryl or a 4-7 membered heterocycloalkyl group, wherein the 5-6 membered heteroaryl or 4-7 membered heterocycloalkyl group is optionally substituted with 1, 2, 3, or 4 independently selected $R^M$ substituents;

each $R^{b111}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{b111}$ are each optionally substituted with 1, 2, 3, or 4 independently selected $R^M$ substituents;

$R^{12}$ is selected from H, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_1$-6 alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a12}$, $SR^{a12}$, $NHOR^{a12}$, $C(O)R^{b12}$, $C(O)NR^{c12}R^{d12}$, $C(O)NR^{c12}(OR^{a12})$, $C(O)OR^{a12}$, $OC(O)R^{b12}$, $OC(O)NR^{c12}R^{d12}$, $NR^{c12}R^{d12}$, $NR^{c12}NR^{c12}R^{d12}$, $NR^{c12}C(O)R^{b12}$, $NR^{c12}C(O)OR^{a12}$, $NR^{c12}C(O)NR^{c12}R^{d12}$, $C(=NR^{e12})R^{b12}$, $C(=NR^{e12})NR^{c12}R^{d12}$, $NR^{c12}C(=NR^{e12})NR^{c12}R^{d12}$, $NR^{c12}C(=NR^{e12})R^{b12}$, $NR^{c12}S(O)R^{b12}$, $NR^{c12}S(O)NR^{c12}R^{d12}$, $NR^{c12}S(O)_2R^{b12}$, $NR^{c12}S(O)(=NR^{e12})R^{b12}$, $NR^{c12}S(O)_2NR^{c12}R^{d12}$, $S(O)R^{b12}$, $S(O)NR^{c12}R^{d12}$ $S(O)_2R^{b12}$, $S(O)_2NR^{c12}R^{d12}$, $OS(O)(=NR^{e12})R^{b12}$, and $OS(O)_2R^{b12}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{12}$ are each optionally substituted with 1, 2, 3, or 4 independently selected $R^{12A}$ substituents;

each $R^{a12}$, $R^{c12}$, and $R^{d12}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a12}$, $R^{c12}$ and $R^{d12}$ are each optionally substituted with 1, 2, 3, or 4 independently selected $R^{12A}$ substituents;

or, any $R^{c12}$ and $R^{d12}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{12A}$ substituents;

each $R^{b12}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b12}$ are each optionally substituted with 1, 2, 3, or 4 independently selected $R^{12A}$ substituents;

each $R^{e12}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{12A}$ is independently selected from halo, $C_{1-6}$ alkyl, $C_{1-6}$ haloalkyl, $C_{2-6}$ alkenyl, $C_2$-6 alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a121}$, $SR^{a121}$, $NHOR^{a121}$, $C(O)R^{b121}$, $C(O)NR^{c121}R^{d121}$, $C(O)NR^{c121}(OR^{a121})$, $C(O)OR^{a121}$, $OC(O)R^{b121}$, $OC(O)NR^{c121}R^{d121}$, $NR^{c121}R^{d121}$, $NR^{c121}NR^{c121}R^{d121}$, $NR^{c121}C(O)R^{b121}$, $NR^{c121}C(O)OR^{a121}$, $NR^{c121}C(O)NR^{c121}R^{d121}$ $C(=NR^{e121})R^{b121}$, $C(=NR^{e121})NR^{c121}R^{d121}$, $NR^{c121}C(=NR^{e121})NR^{c121}R^{d121}$, $NR^{c121}C(=NR^{e121})R^{b121}$, $NR^{c121}S(O)R^{b121}$, $NR^{c121}S(O)NR^{c121}R^{d121}$, $NR^{c121}S(O)_2R^{b121}$, $NR^{c121}S(O)(=NR^{e121})R^{b121}$, $NR^{c121}S(O)_2NR^{c121}R^{d121}$, $S(O)R^{b121}$, $S(O)NR^{c121}R^{d121}$, $S(O)_2R^{b121}$, $S(O)_2NR^{c121}R^{d121}$ $OS(O)(=NR^{e121})R^{b121}$, and $OS(O)_2R^{b121}$;

each $R^{a121}$, $R^{c121}$, and $R^{d121}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

or, any $R^{c121}$ and $R^{d121}$ attached to the same N atom, together with the N atom to which they are attached, form a 5-10 membered heteroaryl or a 4-10 membered heterocycloalkyl group;

each $R^{b121}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{e121}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-; and each $R^M$ is independently selected from H, OH, halo, oxo, CN, C(O)OH, $NH_2$, $NO_2$, $SF_5$, $C_{1-6}$ alkyl, $C_{1-6}$ alkoxy, $C_{1-6}$ haloalkoxy, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-.

49. The compound of claim 1, wherein the compound of Formula I is a compound of Formula II:

II

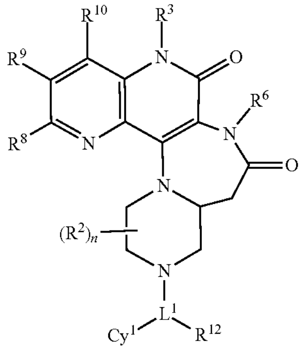

or a pharmaceutically acceptable salt thereof.

50. The compound of claim 1, wherein the compound of Formula I is a compound of Formula III:

III

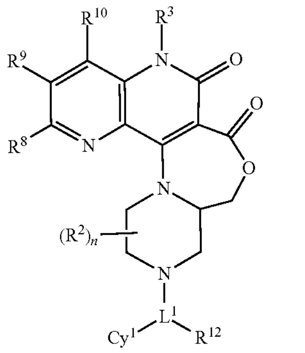

or a pharmaceutically acceptable salt thereof.

51. The compound of claim 1, wherein the compound of Formula I is a compound of Formula IV:

IV

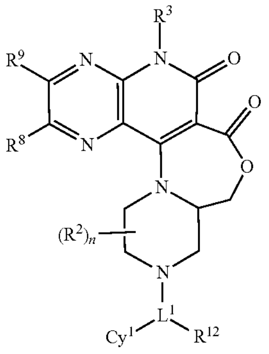

or a pharmaceutically acceptable salt thereof.

52. The compound of claim 1, wherein the compound of Formula I is a compound of Formula V:

V

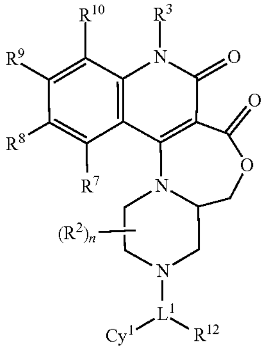

or a pharmaceutically acceptable salt thereof.

53. The compound of claim 1, wherein the compound of Formula I is a compound of Formula VI:

VI

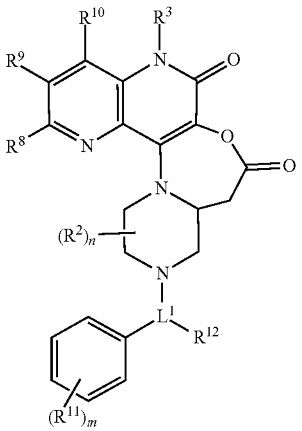

or a pharmaceutically acceptable salt thereof, wherein m is 0, 1, 2, 3, or 4.

54. The compound of claim 1, wherein the compound of Formula I is a compound of Formula VII:

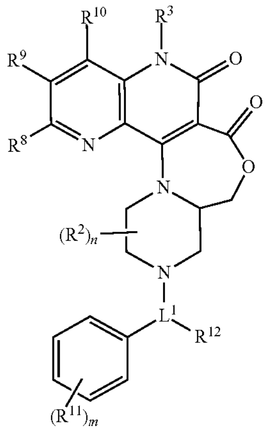

or a pharmaceutically acceptable salt thereof, wherein m is 0, 1, 2, 3, or 4.

55. The compound of claim 1, wherein the compound of Formula I is a compound of Formula VIII:

VIII

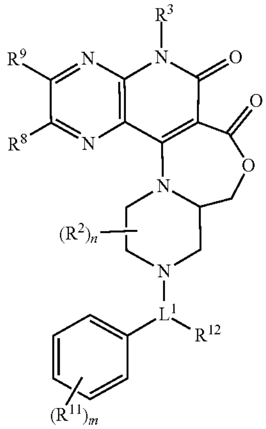

or a pharmaceutically acceptable salt thereof, wherein m is 0, 1, 2, 3, or 4.

56. The compound of claim 1, wherein the compound of Formula I is a compound of Formula IX:

IX

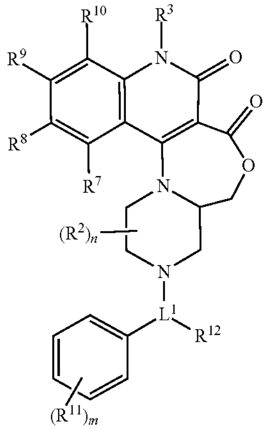

or a pharmaceutically acceptable salt thereof, wherein m is 0, 1, 2, 3, or 4.

57. The compound of claim 1, which is selected from:

11-(bis(4-fluorophenyl)methyl)-5,7-dimethyl-6,8-dioxo-5,6,7,8,9,9a,10,11,12,13-decahydropyrazino[1',2': 4,5][1,4]diazepino[2,3-c][1,5]naphthyridine-2-carbonitrile;

(R)-11-(bis(4-fluorophenyl)methyl)-5-methyl-6,7-dioxo-5,7,9,9a,10,11,12,13-octahydro-6H-pyrazino[2',1':3,4][1,4]oxazepino[6,5-c][1,5]naphthyridine-2-carbonitrile;

(R)-2-(11-(bis(4-fluorophenyl)methyl)-5-methyl-6,7-dioxo-5,7,9,9a,10,11,12, 13-octahydro-6H-pyrazino[2',1':3,4][1,4]oxazepino[6,5-c][1,5]naphthyridin-2-yl) acetonitrile;

(R)-2-(11-(bis(4-fluorophenyl)methyl)-5-methyl-6,7-dioxo-5,7,9,9a,10,11,12,13-octahydro-6H-pyrazino[2,1-c]pyrazino[2',3': 5,6]pyrido[4,3-e][1,4]oxazepin-2-yl) acetonitrile;

(S)-11-(bis(4-fluorophenyl)methyl)-5-methyl-6,7-dioxo-5,7,9,9a,10,11,12, 13-octahydro-6H-pyrazino[2',1':3,4][1,4]oxazepino[6,5-c][1,5]naphthyridine-2-carbonitrile;

(9aR, 12R)-11-(bis(4-fluorophenyl)methyl)-5,12-dimethyl-6,7-dioxo-5,7,9,9a,10,11,12, 13-octahydro-6H-pyrazino[2',1':3,4][1,4]oxazepino[6,5-c][1,5]naphthyridine-2-carbonitrile;

(R)-2-(3-(bis(4-fluorophenyl)methyl)-9-methyl-7,8-dioxo-1,2,3,4,4a,5,8,9-octahydro-7H-pyrazino[2',1':3,4][1,4]oxazepino[6,5-c]quinolin-12-yl) acetonitrile;

(R)-11-(bis(4-fluorophenyl)methyl)-5-methyl-6,7-dioxo-5,7,9,9a,10,11,12, 13-octahydro-6H-pyrazino[2',1':3,4][1,4]oxazepino[6,5-c][1,5]naphthyridine-3-carbonitrile; and (R)-2-(11-(bis(4-fluorophenyl)methyl)-5-methyl-6,7-dioxo-5,7,9,9a,10,11,12,13-octahydro-6H-pyrazino[2',1':3,4][1,4]oxazepino[6,5-c][1,5]naphthyridin-3-yl) acetonitrile;

or a pharmaceutically acceptable salt thereof.

58. The compound of claim 1, or a pharmaceutically acceptable salt thereof, wherein the compound is deuterated.

59. A pharmaceutical composition, comprising a compound of claim 1, or a pharmaceutically acceptable salt thereof, and a pharmaceutically acceptable carrier.

60. A method of inhibiting an activity of a diacylglycerol kinase, comprising contacting the kinase with a compound of claim 1, or a pharmaceutically acceptable salt thereof.

61. A method of treating cancer in a patient in need thereof, the method comprising administering to the patient a therapeutically effective amount of a compound of claim 1, or a pharmaceutically acceptable salt thereof.

62. The method of claim 61, wherein the cancer is non-small cell lung cancer, bladder urothelial carcinoma, esophageal carcinoma, stomach adenocarcinoma, mesothelioma, liver hepatocellular carcinoma, diffuse large B cell lymphoma, kidney renal clear cell carcinoma, head and neck squamous cell carcinoma, cholangiocarcinoma, cervical squamous cell carcinoma, endocervical adenocarcinoma, and melanoma.

63. The method of claim 62, wherein the melanoma is metastatic melanoma.

* * * * *